United States Patent
Meyer

(10) Patent No.: US 11,680,109 B2
(45) Date of Patent: Jun. 20, 2023

(54) COMPOSITIONS AND METHODS FOR DETECTION AND MEASUREMENT OF RNA MODIFICATIONS THROUGH TARGETED RNA EDITING

(71) Applicant: Duke University, Durham, NC (US)

(72) Inventor: Kathryn Meyer, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 357 days.

(21) Appl. No.: 16/886,037

(22) Filed: May 28, 2020

(65) Prior Publication Data
US 2020/0377617 A1 Dec. 3, 2020

Related U.S. Application Data

(60) Provisional application No. 62/853,768, filed on May 29, 2019.

(51) Int. Cl.
| | |
|---|---|
| C07K 16/44 | (2006.01) |
| C12N 9/78 | (2006.01) |
| C12Q 1/686 | (2018.01) |
| C12Q 1/6876 | (2018.01) |

(52) U.S. Cl.
CPC ............... *C07K 16/44* (2013.01); *C12N 9/78* (2013.01); *C12Q 1/686* (2013.01); *C12Q 1/6876* (2013.01); *C12Y 305/04004* (2013.01); *C12Y 305/04005* (2013.01); *C07K 2319/30* (2013.01); *C12Q 2600/154* (2013.01)

(58) Field of Classification Search
None
See application file for complete search history.

(56) References Cited

U.S. PATENT DOCUMENTS

| | | |
|---|---|---|
| 7,635,763 B2 | 12/2009 | Lollar |
| 2011/0104787 A1 | 5/2011 | Church et al. |
| 2011/0183320 A1 | 7/2011 | Flusberg et al. |
| 2016/0060622 A1 | 3/2016 | Jaffrey et al. |
| 2016/0264934 A1 | 9/2016 | Giallourakis et al. |
| 2018/0072793 A1 | 3/2018 | Baysal et al. |

FOREIGN PATENT DOCUMENTS

| | | |
|---|---|---|
| WO | 2007128982 | 11/2007 |
| WO | 2016097212 | 6/2016 |
| WO | 2017040477 | 3/2017 |

OTHER PUBLICATIONS

Stafforst, T. & Schneider M.F., "An RNA-Deaminase Conjugate Selectively Repairs Point Mutations", Angew. Chem. Int. Ed. 2012, 51, 11166-11169.*

Almeida-Porada et al., "Prenatal Transplantation of Placental Cells Engineered to Express FVIII Leads to Corrective Plasma Levels of FVIII after Birth", Blood, vol. 130, No. 1, Dec. 7, 2017, 4 pages.
Almeida-Porada et al., "Transplantation of Fetal Recipients with Placental Cells Engineered to Express FVIII Leads to Corrective Plasma Levels of FVIII after Birth", American Society of Gene & Cell Therapy, Apr. 2018, 3 pages.
Altschul et al., "Basic Local Alignment Search Tool", Journal of Molecular Biology, vol. 215, No. 3, Oct. 5, 1990, pp. 403-410.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Batzer et al., "Enhanced Evolutionary PCR Using Oligonucleotides with Inosine at the 3'-Terminus", Nucleic Acids Research, vol. 19, No. 18, Sep. 25, 1991, p. 5081.
Brown et al., "Bioengineered Coagulation Factor VIII Enables Long-Term Correction of Murine Hemophilia a Following Liver-Directed Adeno-Associated Viral Vector Delivery", Molecular Therapy—Methods and Clinical Development, vol. 1, No. 14036, Aug. 6, 2014, pp. 1-10.
Brown et al., "Target-Cell-Directed Bioengineering Approaches for Gene Therapy of Hemophilia A", Molecular Therapy Methods & Clinical Development, vol. 9, Jun. 2018, pp. 57-69.
Chen et al., "High-Resolution N6-Methyladenosine (m6A) Map Using Photo-Crosslinking-Assisted m6A Sequencing", Angewandte Chemie International Edition, vol. 54, No. 5, Jan. 26, 2015, pp. 1587-1590.
Chudakov et al., "Fluorescent Proteins and their Applications in Imaging Living Cells and Tissues", Physiological Reviews, vol. 90, No. 3, Jul. 1, 2010, pp. 1103-1163.
Doering et al., "Expression and Characterization of Recombinant Murine Factor VIII", Thromb Haemost, vol. 88, No. 3, Sep. 2002, pp. 450-458.
Doering et al., "Identification of Porcine Coagulation Factor VIII Domains Responsible for High Level Expression via Enhanced Secretion", The Journal of Biological Chemistry, vol. 279, No. 8, Feb. 20, 2004, pp. 6546-6552.
El-Akabawy et al., "Defining the Optimal FVIII Transgene for Placental Cell-Based Gene Therapy to Treat Hemophilia A", American Society of Gene & Cell Therapy, vol. 17, Jun. 12, 2020, 3 pages.
Healey et al., "The Comparative Immunogenicity of Human and Porcine Factor VIII in Hemophilia a Mice", Thrombosis and Haemostasis, vol. 102, No. 1, Jul. 2009, pp. 35-41.
Henikoff et al., "Amino Acid Substitution Matrices from Protein Blocks", Proceedings of the National Academy of Sciences of the United States of America, vol. 89, No. 22, Nov. 15, 1992, pp. 10915-10919.

(Continued)

*Primary Examiner* — Suzanne M Noakes
(74) *Attorney, Agent, or Firm* — Kilpatrick Townsend & Stockton LLP

(57) ABSTRACT

Provided herein are compositions and methods for detection of $N^6$-methyladenosine ($m^6A$) in ribonucleic acid (RNA). The provided compositions include fusion proteins that can be used to edit RNA and detect m6A residues. Also provided are nucleic acids, vectors, constructs, host cells, and transgenic animals that encode or express such fusions proteins.

36 Claims, 11 Drawing Sheets
Specification includes a Sequence Listing.

(56) References Cited

OTHER PUBLICATIONS

Karlin et al., "Applications and Statistics for Multiple High-Scoring Segments in Molecular Sequences", Proceedings of the National Academy of Sciences USA, vol. 90, No. 12, Jun. 15, 1993, pp. 5873-5877.

Kuo et al., "Amniotic Fluid Stem Cells for the Treatment of Hemophilia A", Molecular Therapy, vol. 21, No. 1, May 1, 2013, pp. S96-S97.

Lubin et al., "Analysis of the Human Factor VIII A2 Inhibitor Epitope by Alanine Scanning Mutagenesis", The Journal of Biological Chemistry, vol. 272, No. 48, Nov. 28, 1997, pp. 30191-30195.

Merkurjev et al., "Synaptic N6-Methyladenosine (m6A) Epitranscriptome Reveals Functional Partitioning of Localized Transcripts", Nature Neuroscience, vol. 21, Jun. 27, 2018, pp. 1004-1014.

Meyer, "DART-Seq: An Antibody-Free Method For Global m6A Detection", Supplementary Information, Nature Methods, vol. 16, No. 12, Sep. 23, 2019, 21 pages.

Meyer, "DART-Seq: An Antibody-Free Method For Global m6A Detection", Nature Methods, vol. 16, No. 12, Dec. 2019, pp. 1275-1280.

Morsi et al., "Overexpression of FVIII Production in Placental Cells (PLCs) Increases Endogenous vWF", American Society of Gene and Cell Therapy 21st Annual Meeting, Apr. 30, 2018, 3 pages.

Needleman et al., "A General Method Applicable to the Search for Similarities in the Amino Acid Sequence of Two Proteins", Journal of Molecular Biology, vol. 48, No. 3, Mar. 1970, pp. 443-453.

Ohtsuka et al., "An Alternative Approach to Deoxyoligonucleotides as Hybridization Probes by Insertion of Deoxyinosine at Ambiguous Codon Positions", Journal of Biological Chemistry, vol. 260, No. 5, Mar. 10, 1985, pp. 2605-2608.

Pearson et al., "Improved Tools for Biological Sequence Comparison", Proceedings of the National Academy of Sciences of the United States of America, vol. 85, No. 8, Apr. 1988, pp. 2444-2448.

Porada et al., "Hemophilia A: An Ideal Disease to Correct in Utero", Frontiers In Pharmacology, vol. 5, Article 276, Dec. 11, 2014, pp. 1-12.

Porada et al., "Phenotypic Correction of Hemophilia A in Sheep by Postnatal Intraperitoneal Transplantation of FVIII-Expressing MSC", Experimental Hematology, vol. 39, No. 12, Dec. 2011, pp. 1124-1135.

Porada et al., "Treatment of Hemophilia A in Utero and Postnatally Using Sheep as a Model for Cell and Gene Delivery", Journal of Genetic Syndromes & Gene Therapy, vol. S1, May 25, 2012, pp. 1-26.

Rossolini et al., "Use of Deoxyinosine-Containing Primers Vs Degenerate Primers for Polymerase Chain Reaction Based on Ambiguous Sequence Information", Molecular and Cellular Probes, vol. 8, No. 2, Apr. 1994, pp. 91-98.

Schibler et al., "Comparison of Methylated Sequences in Messenger RNA and Heterogeneous Nuclear RNA from Mouse L Cells", Journal of Molecular Biology, vol. 115, No. 4, Oct. 5, 1977, pp. 695-714.

Smith et al., "Comparison of Biosequences", Advances in Applied Mathematics, vol. 2, No. 4, Dec. 1981, pp. 482-489.

Specht et al., "A Critical and Comparative Review of Fluorescent Tools for Live-Cell Imaging", Annual Review of Physiology, vol. 79, Feb. 10, 2017, 28 pages.

Theler et al., "Solution Structure of the YTH Domain in Complex with N6-Methyladenosine RNA: A Reader of Methylated RNA", Nucleic Acids Research, vol. 42, No. 22, Nov. 2014, pp. 1-9.

Wei et al., "5'-Terminal and Internal Methylated Nucleotide Sequences in HeLa Cell mRNA", Biochemistry, vol. 15, No. 2, Jan. 27, 1976, pp. 397-401.

Wei et al., "Nucleotide Sequences at the N6-Methyladenosine Sites of Hela Cell Messenger Ribonucleic Acid", Biochemistry, vol. 16, No. 8, Apr. 19, 1977, pp. 1672-1676.

Yang et al., "COVID-19: Immunopathogenesis and Immunotherapeutics", Signal Transduction and Targeted Therapy, vol. 5, No. 1, Jul. 25, 2020, 8 pages.

Zakas et al., "Development and Characterization of Recombinant Ovine Coagulation Factor VIII", PLoS One, vol. 7, No. 11, Nov. 9, 2012, pp. 1-9.

Akichika, "Cap-Specific Terminal N6-Methylation of RNA by an RNA Polymerase II-Associated Methyltransferase", Science, vol. 363, No. 6423, Jan. 11, 2019, 9 pages.

Baker et al., "Robust RNA-Based In Situ Mutation Detection Delineates Colorectal Cancer Subclonal Evolution", Nature Communications, vol. 8, No. 1, Dec. 2017, pp. 1-8.

Boulias et al., "Identification of the M6Am Methyltransferase PCIFI Reveals the Location and Functions of M6Am in the Transcriptome", BioRxiv, 2018, 38 pages.

Chu et al., "RNA Sequencing: Platform Selection, Experimental Design, and Data Interpretation", Nucleic Acid Therapeutics, vol. 22, No. 4, Oct. 2012, pp. 271-274.

Chylinksi et al., "The tracrRNA and Cas9 Families of Type II CRISPR-Cas Immunity Systems", RNA Biology, vol. 10, No. 5, May 1, 2013, pp. 726-737.

Dominissini et al., "Topology of the Human and Mouse m6A RNA Methylomes Revealed by m6A-Seq", Nature, vol. 485, No. 7397, Apr. 29, 2012, pp. 201-206.

Edelman et al., "Outside and Downstream of the Homeobox*", Journal of Biological Chemistry, vol. 268, No. 28, Oct. 5, 1993, pp. 20683-20686.

Fernandez et al., "Fixation/Permeabilization: New Alternative Procedure for Immunofluorescence and mRNA In Situ Hybridization of Vertebrate and Invertebrate Embryos", Developmental Dynamics, vol. 242, No. 5, 2013, pp. 503-517.

Halloran et al., "Laser-Induced Gene Expression in Specific Cells of Transgenic Zebrafish", Development, vol. 127, No. 9, May 1, 2000, pp. 1953-1960.

Heinz et al., "Simple Combinations of Lineage-Determining Transcription Factors Prime cis-Regulatory Elements Required for Macrophage and B Cell Identities", Molecular Cell, vol. 38, No. 4, May 28, 2010, pp. 576-589.

Hou et al., "Potential Testing and Treatment Strategies for Eliminating HIV", Proceedings of the National Academy of Sciences U.S.A, vol. 110, No. 39, Sep. 24, 2013, pp. 15503-15504.

Jinek et al., "A Programmable Dual-RNA-Guided DNA Endonuclease in Adaptive Bacterial Immunity", Science, vol. 337, No. 6096, Aug. 17, 2012, pp. 816-821.

Ke et al., "A Majority of m6A Residues Are in the Last Exons, Allowing the Potential for 3' UTR Regulation", Genes & Development, vol. 29, No. 19, Oct. 1, 2015, pp. 2037-2053.

Komor et al., "Programmable Editing of a Target Base in Genomic DNA without Double-Stranded DNA Cleavage", Nature, vol. 533, No. 7603, Apr. 20, 2016, pp. 420-424.

Lee et al., "Highly Multiplexed Subcellular RNA Sequencing In Situ", Science, vol. 343, Issue 6177, Mar. 21, 2014, pp. 1360-1363.

Li et al., "Structure of the YTH Domain of Human YTHDF2 in Complex With an m(6)A Mononucleotide Reveals an Aromatic Cage for m(6)A Recognition", Cell Research, vol. 24, No. 12, Dec. 2014, pp. 1490-1492.

Lindenbaum, "JVarkit: Java-based Utilities for Bioinformatics", Institut du Thorax, Available Online at: http://dx.doi.org/10.6084/M9.FIGSHARE.1425030, May 26, 2015, 4 pages.

Linder et al., "Single-Nucleotide-Resolution Mapping of m6A and m6Am Throughout the Transcriptome", Nature Methods, vol. 12, No. 8, Aug. 2015, pp. 767-772.

Liu et al., "Probing N6-methyladenosine RNA Modification Status at Single Nucleotide Resolution in mRNA and Long Noncoding RNA", RNA, vol. 19, No. 12, Dec. 2013, pp. 1848-1856.

Love et al., "Moderated Estimation of Fold Change and Dispersion for RNA-Seq Data with DESeq2", Genome Biology, vol. 15, No. 550, Dec. 2014, 21 pages.

Luo et al., "Molecular Basis for the Recognition of Methylated Adenines in RNA by the Eukaryotic YTH Domain", Proceedings of the National Academy of Sciences of the United States of America, vol. 111, No. 38, Sep. 23, 2014, pp. 13834-13839.

(56) References Cited

OTHER PUBLICATIONS

Makarova et al., "Evolution and Classification of the CRISPR-Cas Systems", Nature Reviews Microbiology, vol. 9, No. 6, Jun. 1, 2011, pp. 467-477.

Martin et al., "Targeted RNA Sequencing Assay to Characterize Gene Expression and Genomic Alterations", Journal of Visualized Experiments, vol. 8, No. 114, Aug. 4, 2016, pp. 1-9.

Mauer et al., "Reversible Methylation of m6Am in the 5' Cap Controls mRNA Stability", Nature, vol. 541, No. 7637, Jan. 19, 2017, pp. 371-375.

Merkurjev et al., "Synaptic m6A Epitranscriptome Reveals Functional Partitioning of Localized Transcripts for Dynamic Tripartite Synapse Modulation", BioRxiv, 2017, 57 pages.

Meyer et al., "Comprehensive Analysis of mRNA Methylation Reveals Enrichment in 3' UTRs and Near Stop Codons", Cell, vol. 149, No. 7, Jun. 22, 2012, pp. 1635-1646.

Meyer, "DART-Seq: A Highly Sensitive, Antibody-Free Method for Global m6A Detection", Department of Biochemistry, Duke University School of Medicine, 2019, 43 pages.

Meyer et al., "Rethinking m6A Readers, Writers, and Erasers", Annual Review of Cell and Developmental Biology, vol. 33, Oct. 6, 2017, pp. 319-342.

Molinie et al., "m(6)A-LAIC-Seq Reveals the Census and Complexity of the m(6)A Epitranscriptome", Nature Methods, vol. 13, No. 8, Aug. 2016, pp. 692-698.

Navaratnam et al., "The p27 Catalytic Subunit of the Apolipoprotein B mRNA Editing Enzyme Is a Cytidine Deaminase", Journal of Biological Chemistry, vol. 268, No. 28, Oct. 5, 1993, pp. 20709-20712.

Olarerin-George et al., "MetaPlotR: a Perl/R Pipeline for Plotting Metagenes of Nucleotide Modifications and other Transcriptomic Sites", Bioinformatics, vol. 33, No. 10, May 15, 2017, pp. 1563-1564.

Patil et al., "Reading m(6)A in the Transcriptome: m(6)ABinding Proteins", Trends in Cell Biology, vol. 28, No. 2, Feb. 2018, pp. 113-127.

Quinlan et al., "BEDTools: A Flexible Suite of Utilities for Comparing Genomic Features", Bioinformatics, vol. 26, No. 6, Mar. 15, 2010, pp. 841-842.

Ricciardelli et al., "Development and Characterization of Primary Cultures of Smooth Muscle Cells From the Fibromuscular Stroma of the Guinea Pig Prostate", In Vitro Cellular and Developmental Biology, vol. 25, 1989, pp. 1016-1024.

Rossi et al., "Recent Advances In Inducible Gene Expression Systems", Current Opinion in Biotechnology, vol. 9, No. 5, Oct. 1998, pp. 451-456.

Sampson et al., "A Crispr/Cas System Mediates Bacterial Innate Immune Evasion and Virulence", Nature, vol. 497, No. 7448, May 9, 2013, pp. 254-257.

Schwartz et al., "Perturbation of m6A Writers Reveals Two Distinct Classes of mRNA Methylation at Internal and 5' Sites", Cell Reports, vol. 8, No. 1, Jul. 10, 2014, pp. 284-296.

Shah et al., "CLIP Tool Kit (CTK): A Flexible and Robust Pipeline to Analyze CLIP Sequencing Data", Bioinformatics, vol. 33, No. 4, Feb. 15, 2017, pp. 566-567.

Slaymaker et al., "Rationally Engineered Cas9 Nucleases With Improved Specificity", Science, vol. 351, No. 6268, 2016, pp. 84-88.

Slobodin et al., "Transcription Impacts the Efficiency of mRNA Translation via Co-transcriptional N6-adenosine Methylation", Cell, vol. 169, No. 2, Apr. 6, 2017, pp. 326-337.

Volobueva et al., "An Update on the Tools for Creating Transgenic Animal Models of Human Diseases-Focus on Atherosclerosis", Brazilian Journal of Medical and Biological Research, vol. 52, No. 5, 2019, pp. 1-7.

Wang et al., "N6-Methyladenosine-Dependent Regulation of Messenger RNA Stability", Nature, vol. 505, 2014, pp. 117-120.

Weng et al., "Epitranscriptomic m6A Regulation of Axon Regeneration in the Adult Mammalian Nervous System", Neuron, vol. 97, No. 2, Jan. 17, 2018, pp. 313-325.

Wu et al., "GMAP: A Genomic Mapping and Alignment Program for mRNA and EST Sequences", Bioinformatics, vol. 21, No. 9, May 1, 2005, pp. 1859-1875.

Xu et al., "Structural Basis for Selective Binding of m6A RNA by the YTHDC1 YTH Domain", Nature Chemical Biology, vol. 10, No. 11, Nov. 2014, pp. 927-929.

Zeng et al., "Refined RIP-Seq Protocol for Epitranscriptome Analysis With Low Input Materials", PLOS Biology, vol. 16, No. 9, Sep. 13, 2018, pp. 1-20.

Zetsche et al., "Cpf1 Is a Single RNA-Guided Endonuclease of a Class 2 CRISPR-Cas System", Cell, vol. 163, No. 3, Oct. 22, 2015, pp. 759-771.

Zhao et al., "Post-Transcriptional Gene Regulation by mRNA Modifications", Nature Reviews Molecular Cell Biology, vol. 18, No. 1, Jan. 2017, pp. 31-42.

\* cited by examiner

SEQUENCE LISTING

<160> NUMBER OF SEQ ID NOS: 64

<210> SEQ ID NO 1
<211> LENGTH: 195
<212> TYPE: PRT
<213> ORGANISM: Artificial Sequence
<220> FEATURE:
<223> OTHER INFORMATION: Synthetic construct

<400> SEQUENCE: 1

```
Pro His Pro Val Leu Glu Lys Leu Arg Ser Ile Asn Asn Tyr Asn Pro
1               5                   10                  15

Lys Asp Phe Asp Trp Asn Leu Lys His Gly Arg Val Phe Ile Ile Lys
            20                  25                  30

Ser Tyr Ser Glu Asp Asp Ile His Arg Ser Ile Lys Tyr Asn Ile Trp
        35                  40                  45

Cys Ser Thr Glu His Gly Asn Lys Arg Leu Asp Ala Ala Tyr Arg Ser
    50                  55                  60

Met Asn Gly Lys Gly Pro Val Tyr Leu Leu Phe Ser Val Asn Gly Ser
65                  70                  75                  80

Gly His Phe Cys Gly Val Ala Glu Met Lys Ser Ala Val Asp Tyr Asn
                85                  90                  95

Thr Cys Ala Gly Val Trp Ser Gln Asp Lys Trp Lys Gly Arg Phe Asp
            100                 105                 110

Val Arg Trp Ile Phe Val Lys Asp Val Pro Asn Ser Gln Leu Arg His
        115                 120                 125

Ile Arg Leu Glu Asn Asn Glu Asn Lys Pro Val Thr Asn Ser Arg Asp
    130                 135                 140

Thr Gln Glu Val Pro Leu Glu Lys Ala Lys Gln Val Leu Lys Ile Ile
145                 150                 155                 160

Ala Ser Tyr Lys His Thr Thr Ser Ile Phe Asp Asp Phe Ser His Tyr
                165                 170                 175

Glu Lys Arg Gln Glu Glu Glu Ser Val Lys Lys Glu Arg Gln Gly
            180                 185                 190

Arg Gly Lys
        195
```

<210> SEQ ID NO 2
<211> LENGTH: 195
<212> TYPE: PRT
<213> ORGANISM: Artificial Sequence
<220> FEATURE:
<223> OTHER INFORMATION: Synthetic construct

<400> SEQUENCE: 2

```
Pro His Pro Val Leu Glu Lys Leu Arg Ser Ile Asn Asn Tyr Asn Pro
1               5                   10                  15

Lys Asp Phe Asp Trp Asn Leu Lys His Gly Arg Val Phe Ile Ile Lys
```

```
                      20                  25                  30
Ser Tyr Ser Glu Asp Ile His Arg Ser Ile Lys Tyr Asn Ile Ala
        35                  40                  45

Cys Ser Thr Glu His Gly Asn Lys Arg Leu Asp Ala Ala Tyr Arg Ser
 50                  55                  60

Met Asn Gly Lys Gly Pro Val Tyr Leu Leu Phe Ser Val Asn Gly Ser
 65                  70                  75                  80

Gly His Phe Cys Gly Val Ala Glu Met Lys Ser Ala Val Asp Tyr Asn
                85                  90                  95

Thr Cys Ala Gly Val Ala Ser Gln Asp Lys Trp Lys Gly Arg Phe Asp
            100                 105                 110

Val Arg Trp Ile Phe Val Lys Asp Val Pro Asn Ser Gln Leu Arg His
            115                 120                 125

Ile Arg Leu Glu Asn Asn Glu Asn Lys Pro Val Thr Asn Ser Arg Asp
            130                 135                 140

Thr Gln Glu Val Pro Leu Glu Lys Ala Lys Gln Val Leu Lys Ile Ile
145                 150                 155                 160

Ala Ser Tyr Lys His Thr Thr Ser Ile Phe Asp Asp Phe Ser His Tyr
                165                 170                 175

Glu Lys Arg Gln Glu Glu Glu Ser Val Lys Lys Glu Arg Gln Gly
            180                 185                 190

Arg Gly Lys
        195

<210> SEQ ID NO 3
<211> LENGTH: 170
<212> TYPE: PRT
<213> ORGANISM: Artificial Sequence
<220> FEATURE:
<223> OTHER INFORMATION: Synthetic construct

<400> SEQUENCE: 3

Gly Arg Val Phe Ile Ile Lys Ser Tyr Ser Glu Asp Ile His Arg
 1               5                  10                  15

Ser Ile Lys Tyr Asn Ile Trp Cys Ser Thr Glu His Gly Asn Lys Arg
                20                  25                  30

Leu Asp Ala Ala Tyr Arg Ser Met Asn Gly Lys Gly Pro Val Tyr Leu
            35                  40                  45

Leu Phe Ser Val Asn Gly Ser Gly His Phe Cys Gly Val Ala Glu Met
         50                  55                  60

Lys Ser Ala Val Asp Tyr Asn Thr Cys Ala Gly Val Trp Ser Gln Asp
 65                  70                  75                  80

Lys Trp Lys Gly Arg Phe Asp Val Arg Trp Ile Phe Val Lys Asp Val
                85                  90                  95

Pro Asn Ser Gln Leu Arg His Ile Arg Leu Glu Asn Asn Glu Asn Lys
            100                 105                 110

Pro Val Thr Asn Ser Arg Asp Thr Gln Glu Val Pro Leu Glu Lys Ala
            115                 120                 125

Lys Gln Val Leu Lys Ile Ile Ala Ser Tyr Lys His Thr Thr Ser Ile
            130                 135                 140

Phe Asp Asp Phe Ser His Tyr Glu Lys Arg Gln Glu Glu Glu Glu Ser
145                 150                 155                 160

Val Lys Lys Glu Arg Gln Gly Arg Gly Lys
                165                 170
```

```
<210> SEQ ID NO 4
<211> LENGTH: 170
<212> TYPE: PRT
<213> ORGANISM: Artificial Sequence
<220> FEATURE:
<223> OTHER INFORMATION: Synthetic construct

<400> SEQUENCE: 4

Gly Arg Val Phe Ile Ile Lys Ser Tyr Ser Glu Asp Ile His Arg
1               5                   10                  15

Ser Ile Lys Tyr Asn Ile Ala Cys Ser Thr Glu His Gly Asn Lys Arg
                20                  25                  30

Leu Asp Ala Ala Tyr Arg Ser Met Asn Gly Lys Gly Pro Val Tyr Leu
            35                  40                  45

Leu Phe Ser Val Asn Gly Ser Gly His Phe Cys Gly Val Ala Glu Met
        50                  55                  60

Lys Ser Ala Val Asp Tyr Asn Thr Cys Ala Gly Val Ala Ser Gln Asp
65                  70                  75                  80

Lys Trp Lys Gly Arg Phe Asp Val Arg Trp Ile Phe Val Lys Asp Val
                85                  90                  95

Pro Asn Ser Gln Leu Arg His Ile Arg Leu Glu Asn Asn Glu Asn Lys
            100                 105                 110

Pro Val Thr Asn Ser Arg Asp Thr Gln Glu Val Pro Leu Glu Lys Ala
        115                 120                 125

Lys Gln Val Leu Lys Ile Ile Ala Ser Tyr Lys His Thr Thr Ser Ile
130                 135                 140

Phe Asp Asp Phe Ser His Tyr Glu Lys Arg Gln Glu Glu Glu Glu Ser
145                 150                 155                 160

Val Lys Lys Glu Arg Gln Gly Arg Gly Lys
                165                 170

<210> SEQ ID NO 5
<211> LENGTH: 195
<212> TYPE: PRT
<213> ORGANISM: Artificial Sequence
<220> FEATURE:
<223> OTHER INFORMATION: Synthetic construct

<400> SEQUENCE: 5

Pro His Pro Val Leu Glu Lys Leu Arg Ser Ile Asn Asn Tyr Asn Pro
1               5                   10                  15

Lys Asp Phe Asp Trp Asn Leu Lys His Gly Arg Val Phe Ile Ile Lys
                20                  25                  30

Ser Tyr Ser Glu Asn Asp Ile His Arg Ser Ile Lys Tyr Asn Ile Trp
            35                  40                  45

Cys Ser Thr Glu His Gly Asn Lys Arg Leu Asp Ala Ala Tyr Arg Ser
        50                  55                  60

Met Asn Gly Lys Gly Pro Val Tyr Leu Leu Phe Ser Val Asn Gly Ser
65                  70                  75                  80

Gly His Phe Cys Gly Val Ala Glu Met Lys Ser Ala Val Asp Tyr Asn
                85                  90                  95

Thr Cys Ala Gly Val Trp Ser Gln Asp Lys Trp Lys Gly Arg Phe Asp
            100                 105                 110

Val Arg Trp Ile Phe Val Lys Asp Val Pro Asn Ser Gln Leu Arg His
        115                 120                 125

Ile Arg Leu Glu Asn Asn Glu Asn Lys Pro Val Thr Asn Ser Arg Asp
130                 135                 140
```

```
Thr Gln Glu Val Pro Leu Glu Lys Ala Lys Gln Val Leu Lys Ile Ile
145                 150                 155                 160

Ala Ser Tyr Lys His Thr Thr Ser Ile Phe Asp Asp Phe Ser His Tyr
                165                 170                 175

Glu Lys Arg Gln Glu Glu Glu Ser Val Lys Lys Glu Arg Gln Gly
            180                 185                 190

Arg Gly Lys
        195

<210> SEQ ID NO 6
<211> LENGTH: 195
<212> TYPE: PRT
<213> ORGANISM: Artificial Sequence
<220> FEATURE:
<223> OTHER INFORMATION: Synthetic construct

<400> SEQUENCE: 6

His Pro Val Leu Glu Lys Leu Lys Ala Ala His Ser Tyr Asn Pro Lys
1               5                   10                  15

Glu Phe Glu Trp Asn Leu Lys Ser Gly Arg Val Phe Ile Ile Lys Ser
            20                  25                  30

Tyr Ser Glu Asp Ile His Arg Ser Ile Lys Tyr Ser Ile Trp Cys
        35                  40                  45

Ser Thr Glu His Gly Asn Lys Arg Leu Asp Ser Ala Phe Arg Cys Met
50                  55                  60

Ser Ser Lys Gly Pro Val Tyr Leu Leu Phe Ser Val Asn Gly Ser Gly
65                  70                  75                  80

His Phe Cys Gly Val Ala Glu Met Lys Ser Pro Val Asp Tyr Gly Thr
                85                  90                  95

Ser Ala Gly Val Trp Ser Gln Asp Lys Trp Lys Gly Lys Phe Asp Val
            100                 105                 110

Gln Trp Ile Phe Val Lys Asp Val Pro Asn Asn Gln Leu Arg His Ile
        115                 120                 125

Arg Leu Glu Asn Asn Asp Asn Lys Pro Val Thr Asn Ser Arg Asp Thr
130                 135                 140

Gln Glu Val Pro Leu Glu Lys Ala Lys Gln Val Leu Lys Ile Ile Ser
145                 150                 155                 160

Ser Tyr Lys His Thr Thr Ser Ile Phe Asp Asp Phe Ala His Tyr Glu
                165                 170                 175

Lys Arg Gln Glu Glu Glu Val Val Arg Lys Glu Arg Gln Ser Arg
            180                 185                 190

Asn Lys Gln
        195

<210> SEQ ID NO 7
<211> LENGTH: 171
<212> TYPE: PRT
<213> ORGANISM: Artificial Sequence
<220> FEATURE:
<223> OTHER INFORMATION: Synthetic construct

<400> SEQUENCE: 7

Gly Arg Val Phe Ile Ile Lys Ser Tyr Ser Glu Asp Asp Ile His Arg
1               5                   10                  15

Ser Ile Lys Tyr Ser Ile Trp Cys Ser Thr Glu His Gly Asn Lys Arg
            20                  25                  30

Leu Asp Ser Ala Phe Arg Cys Met Ser Ser Lys Gly Pro Val Tyr Leu
        35                  40                  45
```

Leu Phe Ser Val Asn Gly Ser Gly His Phe Cys Gly Val Ala Glu Met
    50                  55                  60

Lys Ser Pro Val Asp Tyr Gly Thr Ser Ala Gly Val Trp Ser Gln Asp
65                  70                  75                  80

Lys Trp Lys Gly Lys Phe Asp Val Gln Trp Ile Phe Val Lys Asp Val
                85                  90                  95

Pro Asn Asn Gln Leu Arg His Ile Arg Leu Glu Asn Asn Asp Asn Lys
            100                 105                 110

Pro Val Thr Asn Ser Arg Asp Thr Gln Glu Val Pro Leu Glu Lys Ala
        115                 120                 125

Lys Gln Val Leu Lys Ile Ile Ser Ser Tyr Lys His Thr Thr Ser Ile
    130                 135                 140

Phe Asp Asp Phe Ala His Tyr Glu Lys Arg Gln Glu Glu Glu Glu Val
145                 150                 155                 160

Val Arg Lys Glu Arg Gln Ser Arg Asn Lys Gln
                165                 170

<210> SEQ ID NO 8
<211> LENGTH: 195
<212> TYPE: PRT
<213> ORGANISM: Artificial Sequence
<220> FEATURE:
<223> OTHER INFORMATION: Synthetic construct

<400> SEQUENCE: 8

His Pro Val Leu Glu Lys Leu Lys Ala Ala His Ser Tyr Asn Pro Lys
1               5                   10                  15

Glu Phe Glu Trp Asn Leu Lys Ser Gly Arg Val Phe Ile Ile Lys Ser
            20                  25                  30

Tyr Ser Glu Asp Asn Ile His Arg Ser Ile Lys Tyr Ser Ile Trp Cys
        35                  40                  45

Ser Thr Glu His Gly Asn Lys Arg Leu Asp Ser Ala Phe Arg Cys Met
    50                  55                  60

Ser Ser Lys Gly Pro Val Tyr Leu Leu Phe Ser Val Asn Gly Ser Gly
65                  70                  75                  80

His Phe Cys Gly Val Ala Glu Met Lys Ser Pro Val Asp Tyr Gly Thr
                85                  90                  95

Ser Ala Gly Val Trp Ser Gln Asp Lys Trp Lys Gly Lys Phe Asp Val
            100                 105                 110

Gln Trp Ile Phe Val Lys Asp Val Pro Asn Asn Gln Leu Arg His Ile
        115                 120                 125

Arg Leu Glu Asn Asn Asp Asn Lys Pro Val Thr Asn Ser Arg Asp Thr
    130                 135                 140

Gln Glu Val Pro Leu Glu Lys Ala Lys Gln Val Leu Lys Ile Ile Ser
145                 150                 155                 160

Ser Tyr Lys His Thr Thr Ser Ile Phe Asp Asp Phe Ala His Tyr Glu
                165                 170                 175

Lys Arg Gln Glu Glu Glu Glu Val Val Arg Lys Glu Arg Gln Ser Arg
            180                 185                 190

Asn Lys Gln
        195

<210> SEQ ID NO 9
<211> LENGTH: 195
<212> TYPE: PRT
<213> ORGANISM: Artificial Sequence
<220> FEATURE:
<223> OTHER INFORMATION: Synthetic construct

<400> SEQUENCE: 9

```
Val His Pro Val Leu Glu Lys Leu Lys Ala Ile Asn Asn Tyr Asn Pro
1               5                   10                  15

Lys Asp Phe Asp Trp Asn Leu Lys Asn Gly Arg Val Phe Ile Ile Lys
            20                  25                  30

Ser Tyr Ser Glu Asp Asp Ile His Arg Ser Ile Lys Tyr Ser Ile Trp
        35                  40                  45

Cys Ser Thr Glu His Gly Asn Lys Arg Leu Asp Ala Ala Tyr Arg Ser
    50                  55                  60

Leu Asn Gly Lys Gly Pro Leu Tyr Leu Leu Phe Ser Val Asn Gly Ser
65                  70                  75                  80

Gly His Phe Cys Gly Val Ala Glu Met Lys Ser Val Val Asp Tyr Asn
                85                  90                  95

Ala Tyr Ala Gly Val Trp Ser Gln Asp Lys Trp Lys Gly Lys Phe Glu
            100                 105                 110

Val Lys Trp Ile Phe Val Lys Asp Val Pro Asn Asn Gln Leu Arg His
        115                 120                 125

Ile Arg Leu Glu Asn Asn Asp Asn Lys Pro Val Thr Asn Ser Arg Asp
    130                 135                 140

Thr Gln Glu Val Pro Leu Glu Lys Ala Lys Gln Val Leu Lys Ile Ile
145                 150                 155                 160

Ala Thr Phe Lys His Thr Thr Ser Ile Phe Asp Asp Phe Ala His Tyr
                165                 170                 175

Glu Lys Arg Gln Glu Glu Glu Ala Met Arg Arg Glu Arg Asn Arg
            180                 185                 190

Asn Lys Gln
        195
```

<210> SEQ ID NO 10
<211> LENGTH: 165
<212> TYPE: PRT
<213> ORGANISM: Artificial Sequence
<220> FEATURE:
<223> OTHER INFORMATION: Synthetic construct

<400> SEQUENCE: 10

```
Ser Lys Leu Lys Tyr Val Leu Gln Asp Ala Arg Phe Phe Leu Ile Lys
1               5                   10                  15

Ser Asn Asn His Glu Asn Val Ser Leu Ala Lys Ala Lys Gly Val Trp
            20                  25                  30

Ser Thr Leu Pro Val Asn Glu Lys Lys Leu Asn Leu Ala Phe Arg Ser
        35                  40                  45

Ala Arg Ser Val Ile Leu Ile Phe Ser Val Arg Glu Ser Gly Lys Phe
    50                  55                  60

Gln Gly Phe Ala Arg Leu Ser Ser Glu Ser His His Gly Gly Ser Pro
65                  70                  75                  80

Ile His Trp Val Leu Pro Ala Gly Met Ser Ala Lys Met Leu Gly Gly
                85                  90                  95

Val Phe Lys Ile Asp Trp Ile Cys Arg Arg Glu Leu Pro Phe Thr Lys
            100                 105                 110

Ser Ala His Leu Thr Asn Pro Trp Asn Glu His Lys Pro Val Lys Ile
        115                 120                 125

Gly Arg Asp Gly Gln Glu Ile Glu Leu Glu Cys Gly Thr Gln Leu Cys
```

```
                130                 135                 140
Leu Leu Phe Pro Pro Asp Glu Ser Ile Asp Leu Tyr Gln Val Ile His
145                 150                 155                 160

Lys Met Arg His Lys
            165

<210> SEQ ID NO 11
<211> LENGTH: 144
<212> TYPE: PRT
<213> ORGANISM: Artificial Sequence
<220> FEATURE:
<223> OTHER INFORMATION: Synthetic construct

<400> SEQUENCE: 11

Pro Val Arg Tyr Phe Ile Met Lys Ser Ser Asn Leu Arg Asn Leu Glu
1               5                   10                  15

Ile Ser Gln Gln Lys Gly Ile Trp Ser Thr Thr Pro Ser Asn Glu Arg
                20                  25                  30

Lys Leu Asn Arg Ala Phe Trp Glu Ser Ser Ile Val Tyr Leu Val Phe
            35                  40                  45

Ser Val Gln Gly Ser Gly His Phe Gln Gly Phe Ser Arg Met Ser Ser
50                  55                  60

Glu Ile Gly Arg Glu Lys Ser Gln Asp Trp Gly Ser Ala Gly Leu Gly
65                  70                  75                  80

Gly Val Phe Lys Val Glu Trp Ile Arg Lys Glu Ser Leu Pro Phe Gln
                85                  90                  95

Phe Ala His His Leu Leu Asn Pro Trp Asn Asp Asn Lys Lys Val Gln
            100                 105                 110

Ile Ser Arg Asp Gly Gln Glu Leu Glu Pro Leu Val Gly Glu Gln Leu
        115                 120                 125

Leu Gln Leu Trp Glu Arg Leu Pro Leu Gly Glu Lys Asn Thr Thr Asp
    130                 135                 140

<210> SEQ ID NO 12
<211> LENGTH: 229
<212> TYPE: PRT
<213> ORGANISM: Artificial Sequence
<220> FEATURE:
<223> OTHER INFORMATION: Synthetic construct

<400> SEQUENCE: 12

Met Ser Ser Glu Thr Gly Pro Val Ala Val Asp Pro Thr Leu Arg Arg
1               5                   10                  15

Arg Ile Glu Pro His Glu Phe Glu Val Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Lys His Val Glu Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125
```

```
Gln Gly Leu Arg Asp Leu Ile Ser Ser Gly Val Thr Ile Gln Ile Met
            130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
                195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 13
<211> LENGTH: 198
<212> TYPE: PRT
<213> ORGANISM: Artificial Sequence
<220> FEATURE:
<223> OTHER INFORMATION: Synthetic construct

<400> SEQUENCE: 13

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 14
<211> LENGTH: 199
<212> TYPE: PRT
<213> ORGANISM: Artificial Sequence
<220> FEATURE:
<223> OTHER INFORMATION: Synthetic construct

<400> SEQUENCE: 14
```

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 15
<211> LENGTH: 385
<212> TYPE: PRT
<213> ORGANISM: Artificial Sequence
<220> FEATURE:
<223> OTHER INFORMATION: Synthetic construct

<400> SEQUENCE: 15

Gln Leu His Leu Pro Gln Val Leu Ala Asp Ala Val Ser Arg Leu Val
1               5                   10                  15

Leu Gly Lys Phe Gly Asp Leu Thr Asp Asn Phe Ser Ser Pro His Ala
            20                  25                  30

Arg Arg Lys Val Leu Ala Gly Val Val Met Thr Thr Gly Thr Asp Val
            35                  40                  45

Lys Asp Ala Lys Val Ile Ser Val Ser Thr Gly Thr Lys Cys Ile Asn
    50                  55                  60

Gly Glu Tyr Met Ser Asp Arg Gly Leu Ala Leu Asn Asp Cys His Ala
65                  70                  75                  80

Glu Ile Ile Ser Arg Arg Ser Leu Leu Arg Phe Leu Tyr Thr Gln Leu
                85                  90                  95

Glu Leu Tyr Leu Asn Asn Lys Asp Asp Gln Lys Arg Ser Ile Phe Gln
            100                 105                 110

Lys Ser Glu Arg Gly Gly Phe Arg Leu Lys Glu Asn Val Gln Phe His
            115                 120                 125

Leu Tyr Ile Ser Thr Ser Pro Cys Gly Asp Ala Arg Ile Phe Ser Pro
130                 135                 140

His Glu Pro Ile Leu Glu Glu Pro Ala Asp Arg His Pro Asn Arg Lys
145                 150                 155                 160
```

Ala Arg Gly Gln Leu Arg Thr Lys Ile Glu Ser Gly Gln Gly Thr Ile
            165                 170                 175

Pro Val Arg Ser Asn Ala Ser Ile Gln Thr Trp Asp Gly Val Leu Gln
        180                 185                 190

Gly Glu Arg Leu Leu Thr Met Ser Cys Ser Asp Lys Ile Ala Arg Trp
    195                 200                 205

Asn Val Val Gly Ile Gln Gly Ser Leu Leu Ser Ile Phe Val Glu Pro
210                 215                 220

Ile Tyr Phe Ser Ser Ile Ile Leu Gly Ser Leu Tyr His Gly Asp His
225                 230                 235                 240

Leu Ser Arg Ala Met Tyr Gln Arg Ile Ser Asn Ile Glu Asp Leu Pro
            245                 250                 255

Pro Leu Tyr Thr Leu Asn Lys Pro Leu Leu Ser Gly Ile Ser Asn Ala
        260                 265                 270

Glu Ala Arg Gln Pro Gly Lys Ala Pro Asn Phe Ser Val Asn Trp Thr
    275                 280                 285

Val Gly Asp Ser Ala Ile Glu Val Ile Asn Ala Thr Thr Gly Lys Asp
290                 295                 300

Glu Leu Gly Arg Ala Ser Arg Leu Cys Lys His Ala Leu Tyr Cys Arg
305                 310                 315                 320

Trp Met Arg Val His Gly Lys Val Pro Ser His Leu Leu Arg Ser Lys
            325                 330                 335

Ile Thr Lys Pro Asn Val Tyr His Glu Ser Lys Leu Ala Ala Lys Glu
        340                 345                 350

Tyr Gln Ala Ala Lys Ala Arg Leu Phe Thr Ala Phe Ile Lys Ala Gly
    355                 360                 365

Leu Gly Ala Trp Val Glu Lys Pro Thr Glu Gln Asp Gln Phe Ser Leu
370                 375                 380

Thr
385

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Ser Gly Ser Glu Thr Pro Gly Thr Ser Glu Ser Ala Thr Pro Glu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Ser Gly Ser Glu Thr Pro Gly Thr Ser Glu Ser Ala Thr Pro Glu Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 50
<212> TYPE: PRT
<213> ORGANISM: Artificial Sequence
<220> FEATURE:
<223> OTHER INFORMATION: Synthetic construct

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 20
<211> LENGTH: 100
<212> TYPE: PRT
<213> ORGANISM: Artificial Sequence
<220> FEATURE:
<223> OTHER INFORMATION: Synthetic construct

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 21
<211> LENGTH: 17
<212> TYPE: PRT
<213> ORGANISM: Artificial Sequence
<220> FEATURE:
<223> OTHER INFORMATION: Synthetic construct

<400> SEQUENCE: 21

Ala Glu Ala Ala Ala Lys Glu Ala Ala Ala Lys Glu Ala Ala Ala Lys
1               5                   10                  15

Ala

<210> SEQ ID NO 22
<211> LENGTH: 52
<212> TYPE: PRT
<213> ORGANISM: Artificial Sequence
<220> FEATURE:
<223> OTHER INFORMATION: Synthetic construct

<400> SEQUENCE: 22

Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Glu Ala Ala Ala Lys Glu
            20                  25                  30
Ala Ala Ala Lys Glu Ala Ala Ala Lys Glu Ala Ala Ala Lys Glu Ala
        35                  40                  45
Ala Ala Lys Ala
    50

<210> SEQ ID NO 23
<211> LENGTH: 102
<212> TYPE: PRT
<213> ORGANISM: Artificial Sequence
<220> FEATURE:
<223> OTHER INFORMATION: Synthetic construct

<400> SEQUENCE: 23

Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Glu Ala Ala Ala Lys Glu
            20                  25                  30
Ala Ala Ala Lys Glu Ala Ala Ala Lys Glu Ala Ala Ala Lys Glu Ala
        35                  40                  45
Ala Ala Lys Glu Ala Ala Ala Lys Glu Ala Ala Ala Lys Glu Ala Ala
    50                  55                  60
Ala Lys Glu Ala Ala Ala Lys Glu Ala Ala Ala Lys Glu Ala Ala Ala
65                  70                  75                  80
Lys Glu Ala Ala Ala Lys Glu Ala Ala Ala Lys Glu Ala Ala Ala Lys
                85                  90                  95
Glu Ala Ala Ala Lys Ala
            100

<210> SEQ ID NO 24
<211> LENGTH: 7
<212> TYPE: PRT
<213> ORGANISM: Artificial Sequence
<220> FEATURE:
<223> OTHER INFORMATION: Synthetic construct

<400> SEQUENCE: 24

Pro Lys Lys Lys Arg Lys Val
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic construct

<400> SEQUENCE: 25

Leu Pro Pro Leu Glu Arg Leu Thr
1               5

<210> SEQ ID NO 26
<211> LENGTH: 27
<212> TYPE: PRT
<213> ORGANISM: Artificial Sequence
<220> FEATURE:
<223> OTHER INFORMATION: Synthetic construct

<400> SEQUENCE: 26

Met Asp Pro Val Val Val Leu Gly Leu Cys Leu Ser Cys Leu Leu Leu
1               5                   10                  15

Leu Ser Leu Trp Lys Gln Ser Tyr Gly Gly Gly
            20                  25

<210> SEQ ID NO 27
<211> LENGTH: 10
<212> TYPE: PRT
<213> ORGANISM: Artificial Sequence
<220> FEATURE:
<223> OTHER INFORMATION: Synthetic construct

<400> SEQUENCE: 27

Glu Gln Lys Leu Ile Ser Glu Glu Asp Leu
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic construct

<400> SEQUENCE: 28

Gly Lys Pro Ile Pro Asn Pro Leu Leu Gly Leu Asp Ser Thr
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic construct

<400> SEQUENCE: 29

Ile Pro Asn Pro Leu Leu Gly Leu Asp
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct

<400> SEQUENCE: 30

Asp Tyr Lys Asp Asp Asp Asp Lys
1               5

<210> SEQ ID NO 31
<211> LENGTH: 22
<212> TYPE: PRT
<213> ORGANISM: Artificial Sequence
<220> FEATURE:
<223> OTHER INFORMATION: Synthetic construct

<400> SEQUENCE: 31

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 32
<211> LENGTH: 158
<212> TYPE: PRT
<213> ORGANISM: Artificial Sequence
<220> FEATURE:
<223> OTHER INFORMATION: Synthetic construct

<400> SEQUENCE: 32

```
Ile Ser Leu Ile Ala Ala Leu Ala Val Asp His Val Ile Gly Met Glu
1               5                   10                  15

Thr Val Met Pro Trp Asn Leu Pro Ala Asp Leu Ala Trp Phe Lys Arg
            20                  25                  30

Asn Thr Leu Asn Lys Pro Val Ile Met Gly Arg His Thr Trp Glu Ser
                35                  40                  45

Ile Gly Arg Pro Leu Pro Gly Arg Lys Asn Ile Ile Leu Ser Ser Gln
        50                  55                  60

Pro Ser Thr Asp Asp Arg Val Thr Trp Val Lys Ser Val Asp Glu Ala
65                  70                  75                  80

Ile Ala Ala Cys Gly Asp Val Pro Glu Ile Met Val Ile Gly Gly Gly
                85                  90                  95

Arg Val Tyr Glu Gln Phe Leu Pro Lys Ala Gln Lys Leu Tyr Leu Thr
            100                 105                 110

His Ile Asp Ala Glu Val Glu Gly Asp Thr His Phe Pro Asp Tyr Glu
        115                 120                 125

Pro Asp Asp Trp Glu Ser Val Phe Ser Glu Phe His Asp Ala Asp Ala
130                 135                 140

Gln Asn Ser His Ser Tyr Cys Phe Glu Ile Leu Glu Arg Arg
145                 150                 155
```

<210> SEQ ID NO 33
<211> LENGTH: 9
<212> TYPE: PRT
<213> ORGANISM: Artificial Sequence
<220> FEATURE:
<223> OTHER INFORMATION: Synthetic construct

<400> SEQUENCE: 33

```
Tyr Pro Tyr Asp Val Pro Asp Tyr Ala
1               5
```

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
ggagttgatt gaggtaaagc g                                            21

<210> SEQ ID NO 35
<211> LENGTH: 18
<212> TYPE: RNA
<213> ORGANISM: Artificial Sequence
<220> FEATURE:
<223> OTHER INFORMATION: Synthetic construct

<400> SEQUENCE: 35
guucuucugu ggacugug                                                18

<210> SEQ ID NO 36

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
agactcccgg gacctcagag                                                 20

<210> SEQ ID NO 37
<211> LENGTH: 54
<212> TYPE: DNA
<213> ORGANISM: Artificial Sequence
<220> FEATURE:
<223> OTHER INFORMATION: Synthetic construct

<400> SEQUENCE: 37
actcccggga cctcagagtc cgccacacca gaaggccggg ttttcatcat taag           54

<210> SEQ ID NO 38
<211> LENGTH: 23
<212> TYPE: DNA
<213> ORGANISM: Artificial Sequence
<220> FEATURE:
<223> OTHER INFORMATION: Synthetic construct

<400> SEQUENCE: 38
cgggtttaaa ctcaggcgta gtc                                             23

<210> SEQ ID NO 39
<211> LENGTH: 25
<212> TYPE: DNA
<213> ORGANISM: Artificial Sequence
<220> FEATURE:
<223> OTHER INFORMATION: Synthetic construct

<400> SEQUENCE: 39 gtggggcga tctttattgt ggcgg                                            25

<210> SEQ ID NO 40
<211> LENGTH: 24
<212> TYPE: DNA
<213> ORGANISM: Artificial Sequence
<220> FEATURE:
<223> OTHER INFORMATION: Synthetic construct

<400> SEQUENCE: 40
tgtgcaatca aagtcctcgg ccac                                            24

<210> SEQ ID NO 41
<211> LENGTH: 22
<212> TYPE: DNA
<213> ORGANISM: Artificial Sequence
<220> FEATURE:
<223> OTHER INFORMATION: Synthetic construct

<400> SEQUENCE: 41
gccaatgctg tctggttgcg cc                                              22

<210> SEQ ID NO 42
<211> LENGTH: 22
<212> TYPE: DNA
<213> ORGANISM: Artificial Sequence
<220> FEATURE:
<223> OTHER INFORMATION: Synthetic construct

<400> SEQUENCE: 42
```
ggaggcttct gcggttctgg ag                                            22

<210> SEQ ID NO 43
<211> LENGTH: 24
<212> TYPE: DNA
<213> ORGANISM: Artificial Sequence
<220> FEATURE:
<223> OTHER INFORMATION: Synthetic construct

<400> SEQUENCE: 43
cagcaagcag gagtatgacg agtc                                          24

<210> SEQ ID NO 44
<211> LENGTH: 18
<212> TYPE: DNA
<213> ORGANISM: Artificial Sequence
<220> FEATURE:
<223> OTHER INFORMATION: Synthetic construct

<400> SEQUENCE: 44
catgccaatc tcatcttg                                                 18

<210> SEQ ID NO 45
<211> LENGTH: 21
<212> TYPE: DNA
<213> ORGANISM: Artificial Sequence
<220> FEATURE:
<223> OTHER INFORMATION: Synthetic construct

<400> SEQUENCE: 45
catgtacgtt gctatccagg c                                             21

<210> SEQ ID NO 46
<211> LENGTH: 21
<212> TYPE: DNA
<213> ORGANISM: Artificial Sequence
<220> FEATURE:
<223> OTHER INFORMATION: Synthetic construct

<400> SEQUENCE: 46
ctccttaatg tcacgcacga t                                             21

<210> SEQ ID NO 47
<211> LENGTH: 26
<212> TYPE: DNA
<213> ORGANISM: Artificial Sequence
<220> FEATURE:
<223> OTHER INFORMATION: Synthetic construct

<400> SEQUENCE: 47
cgaagatccc cacgtgtaaa gactac                                        26

<210> SEQ ID NO 48
<211> LENGTH: 22
<212> TYPE: DNA
<213> ORGANISM: Artificial Sequence
<220> FEATURE:
<223> OTHER INFORMATION: Synthetic construct

<400> SEQUENCE: 48
catcctgctc acctctttga gg                                            22

<210> SEQ ID NO 49
<211> LENGTH: 26
<212> TYPE: DNA

<213> ORGANISM: Artificial Sequence
<220> FEATURE:
<223> OTHER INFORMATION: Synthetic construct

<400> SEQUENCE: 49
gtgttagatg atgtctccat tcggag         26

<210> SEQ ID NO 50
<211> LENGTH: 22
<212> TYPE: DNA
<213> ORGANISM: Artificial Sequence
<220> FEATURE:
<223> OTHER INFORMATION: Synthetic construct

<400> SEQUENCE: 50
cactttcctc ctgtatgagc gg             22

<210> SEQ ID NO 51
<211> LENGTH: 21
<212> TYPE: DNA
<213> ORGANISM: Artificial Sequence
<220> FEATURE:
<223> OTHER INFORMATION: Synthetic construct

<400> SEQUENCE: 51
gccaagaggc aacacaccaa c              21

<210> SEQ ID NO 52
<211> LENGTH: 23
<212> TYPE: DNA
<213> ORGANISM: Artificial Sequence
<220> FEATURE:
<223> OTHER INFORMATION: Synthetic construct

<400> SEQUENCE: 52
cggtttctct cggtctgttt tcc            23

<210> SEQ ID NO 53
<211> LENGTH: 25
<212> TYPE: DNA
<213> ORGANISM: Artificial Sequence
<220> FEATURE:
<223> OTHER INFORMATION: Synthetic construct

<400> SEQUENCE: 53
cagaaggcga caacacagca acacc          25

<210> SEQ ID NO 54
<211> LENGTH: 18
<212> TYPE: DNA
<213> ORGANISM: Artificial Sequence
<220> FEATURE:
<223> OTHER INFORMATION: Synthetic construct

<400> SEQUENCE: 54
tacttccaat ccaatgca                  18

<210> SEQ ID NO 55
<211> LENGTH: 22
<212> TYPE: DNA
<213> ORGANISM: Artificial Sequence
<220> FEATURE:
<223> OTHER INFORMATION: Synthetic construct

<400> SEQUENCE: 55
ttatccactt ccaatgttat ta             22

<210> SEQ ID NO 56
<211> LENGTH: 17
<212> TYPE: DNA
<213> ORGANISM: Artificial Sequence
<220> FEATURE:
<223> OTHER INFORMATION: Synthetic construct

<400> SEQUENCE: 56
tactaggacg caccotta                                                17

<210> SEQ ID NO 57
<211> LENGTH: 17
<212> TYPE: DNA
<213> ORGANISM: Artificial Sequence
<220> FEATURE:
<223> OTHER INFORMATION: Synthetic construct

<400> SEQUENCE: 57
tactaggatg caccotta                                                17

<210> SEQ ID NO 58
<211> LENGTH: 1368
<212> TYPE: DNA
<213> ORGANISM: Artificial Sequence
<220> FEATURE:
<223> OTHER INFORMATION: Synthetic construct

<400> SEQUENCE: 58

```
atgagcagcg aaaccggtcc ggtggcggtt gacccgaccc tgcgtcgtcg tattgagccg      60
cacgagttcg aagtgttctt tgatccgcgt gagctgcgta aggaaacctg cctgctgtac     120
gaaattaact ggggtggccg tcacagcatc tggcgtcaca ccagccagaa caccaacaag     180
cacgttgagg tgaacttcat cgaaaaattt accaccgagc gttacttctg cccgaacacc     240
cgttgcagca ttacctggtt tctgagctgg agcccgtgcg tgaatgcag ccgtgcgatc      300
accgagttcc tgagccgtta ccgcacgtt accctgttta tctacattgc gcgtctgtat     360
caccacgcgg acccgcgtaa ccgtcaaggt ctgcgtgatc tgatcagcag cggcgtgacc     420
atccagatta tgaccgagca agaaagcggt tactgctggc gtaacttcgt taactatagc     480
ccgagcaacg aagcgcattg gccgcgttac ccgcacctgt gggtgcgtct gtacgttctg     540
gagctgtatt gcatcattct gggcctgccg ccgtgcctga acattctgcg tcgtaagcag     600
ccgcaactga ccttctttac catcgcgctg cagagctgcc actaccaacg tctgccgccg     660
cacattctgt gggcgaccgg tctgaagagc ggcagcgaaa ccccgggtac cagcgaaagc     720
gcgaccccgg agccgcaccc ggtgctggag aaactgcgta gcatcaacaa ctataacccg     780
aaggacttcg attggaacct gaaacaccgt cgtgttttta tcattaagag ctacagcgaa     840
gacgatatcc accgtagcat taaatataac atctggtgca gcaccgagca cggcaacaag     900
cgtctggacg cggcgtaccg tagcatgaac ggtaaaggcc ggtgtatct gctgttcagc      960
gttaacggta gcggccactt tgcggtgtg gcggaaatga aagcgcggt tgattacaac      1020
acctgcgcgg gtgtgtggag ccaggacaag tggaaaggcc gtttcgatgt tcgttggatt    1080
tttgtgaagg acgttccgaa cagccaactg cgtcacatcc gtctggagaa caacgaaaac    1140
aaaccggtga ccaacagccc tgataccccag gaagtgccgc tggaaaaggc gaaacaagtt    1200
ctgaagatca ttgcgagcta caaacacacc accagcatct tcgacgattt tagccactat    1260
gagaagcgtc aggaagagga agagagcgtg aagaaggagc gtcaaggtcg tggcaaactg    1320
```
gagtacccgt atgacgttcc ggattatgcg taaattggaa gtggataa        1368

<210> SEQ ID NO 59
<211> LENGTH: 1293
<212> TYPE: DNA
<213> ORGANISM: Artificial Sequence
<220> FEATURE:
<223> OTHER INFORMATION: Synthetic construct

<400> SEQUENCE: 59

```
atgagcagcg aaaccggtcc ggtggcggtt gacccgaccc tgcgtcgtcg tattgagccg      60
cacgagttcg aagtgttctt tgatccgcgt gagctgcgta aggaaacctg cctgctgtac     120
gaaattaact ggggtggccg tcacagcatc tggcgtcaca ccagccagaa caccaacaag     180
cacgttgagg tgaacttcat cgaaaaattt accaccgagc gttacttctg cccgaacacc     240
cgttgcagca ttacctggtt tctgagctgg agcccgtgcg gtgaatgcag ccgtgcgatc     300
accgagttcc tgagccgtta tccgcacgtt accctgttta tctacattgc gcgtctgtat     360
caccacgcgg acccgcgtaa ccgtcaaggt ctgcgtgatc tgatcagcag cggcgtgacc     420
atccagatta tgaccgagca agaaagcggt tactgctggc gtaacttcgt taactatagc     480
ccgagcaacg aagcgcattg gccgcgttac ccgcacctgt gggtgcgtct gtacgttctg     540
gagctgtatt gcatcattct gggcctgccg ccgtgcctga acattctgcg tcgtaagcag     600
ccgcaactga ccttctttac catcgcgctg cagagctgcc actaccaacg tctgccgccg     660
cacattctgt gggcgaccgg tctgaagagc ggcagcgaaa ccccgggtac cagcgaaagc     720
gcgaccccgg agggtcgtgt ttttatcatt aagagctaca gcgaagacga tatccaccgt     780
agcattaaat ataacatctg gtgcagcacc gagcacggca acaagcgtct ggacgcggcg     840
taccgtagca tgaacggtaa aggcccggtg tatctgctgt tcagcgttaa cggtagcggc     900
cacttttgcg gtgtggcgga atgaaaagc gcggttgatt acaacacctg cgcgggtgtg     960
tggagccagg acaagtggaa aggccgtttc gatgttcgtt ggattttgt gaaggacgtt    1020
ccgaacagcc aactgcgtca catccgtctg gagaacaacg aaaacaaacc ggtgaccaac    1080
agccgtgata cccaggaagt gccgctggaa aaggcgaaac aagttctgaa gatcattgcg    1140
agctacaaac acaccaccag catcttcgac gattttagcc actatgagaa cgtcaggaa    1200
gaggaagaga gcgtgaagaa ggagcgtcaa ggtcgtggca aactggagta cccgtatgac    1260
gttccggatt atgcgtaaat tggaagtgga taa                                1293
```

<210> SEQ ID NO 60
<211> LENGTH: 21
<212> TYPE: PRT
<213> ORGANISM: Artificial Sequence
<220> FEATURE:
<223> OTHER INFORMATION: Synthetic construct

<400> SEQUENCE: 60

Met Glu Thr Asp Thr Leu Leu Leu Trp Val Leu Leu Leu Trp Val Pro
1               5                   10                  15

Gly Ser Thr Gly Asp
            20

<210> SEQ ID NO 61
<211> LENGTH: 215
<212> TYPE: PRT
<213> ORGANISM: Artificial Sequence
<220> FEATURE:
<223> OTHER INFORMATION: Synthetic construct

<400> SEQUENCE: 61

```
Arg Arg Arg Ile Glu Pro His Glu Phe Glu Val Phe Asp Pro Arg
1               5                   10                  15

Glu Leu Arg Lys Glu Thr Cys Leu Leu Tyr Glu Ile Asn Trp Gly Gly
            20                  25                  30

Arg His Ser Ile Trp Arg His Thr Ser Gln Asn Thr Asn Lys His Val
            35                  40                  45

Glu Val Asn Phe Ile Glu Lys Phe Thr Thr Glu Arg Tyr Phe Cys Pro
    50                  55                  60

Asn Thr Arg Cys Ser Ile Thr Trp Phe Leu Ser Trp Ser Pro Cys Gly
65                  70                  75                  80

Glu Cys Ser Arg Ala Ile Thr Glu Phe Leu Ser Arg Tyr Pro His Val
                85                  90                  95

Thr Leu Phe Ile Tyr Ile Ala Arg Leu Tyr His His Ala Asp Pro Arg
                100                 105                 110

Asn Arg Gln Gly Leu Arg Asp Leu Ile Ser Ser Gly Val Thr Ile Gln
            115                 120                 125

Ile Met Thr Glu Gln Glu Ser Gly Tyr Cys Trp Arg Asn Phe Val Asn
130                 135                 140

Tyr Ser Pro Ser Asn Glu Ala His Trp Pro Arg Tyr Pro His Leu Trp
145                 150                 155                 160

Val Arg Leu Tyr Val Leu Glu Leu Tyr Cys Ile Ile Leu Gly Leu Pro
                165                 170                 175

Pro Cys Leu Asn Ile Leu Arg Arg Lys Gln Pro Gln Leu Thr Phe Phe
            180                 185                 190

Thr Ile Ala Leu Gln Ser Cys His Tyr Gln Arg Leu Pro Pro His Ile
            195                 200                 205

Leu Trp Ala Thr Gly Leu Lys
            210                 215
```

<210> SEQ ID NO 62
<211> LENGTH: 179
<212> TYPE: PRT
<213> ORGANISM: Artificial Sequence
<220> FEATURE:
<223> OTHER INFORMATION: Synthetic construct

<400> SEQUENCE: 62

```
Leu Met Asn Arg Arg Lys Phe Leu Tyr Gln Phe Lys Asn Val Arg Trp
1               5                   10                  15

Ala Lys Gly Arg Arg Glu Thr Tyr Leu Cys Tyr Val Val Lys Arg Arg
            20                  25                  30

Asp Ser Ala Thr Ser Phe Ser Leu Asp Phe Gly Tyr Leu Arg Asn Lys
        35                  40                  45

Asn Gly Cys His Val Glu Leu Leu Phe Leu Arg Tyr Ile Ser Asp Trp
    50                  55                  60

Asp Leu Asp Pro Gly Arg Cys Tyr Arg Val Thr Trp Phe Thr Ser Trp
65                  70                  75                  80

Ser Pro Cys Tyr Asp Cys Ala Arg His Val Ala Asp Phe Leu Arg Gly
                85                  90                  95

Asn Pro Asn Leu Ser Leu Arg Ile Phe Thr Ala Arg Leu Tyr Phe Cys
            100                 105                 110

Glu Asp Arg Lys Ala Glu Pro Glu Gly Leu Arg Arg Leu His Arg Ala
            115                 120                 125
```

Gly Val Gln Ile Ala Ile Met Thr Phe Lys Asp Tyr Phe Tyr Cys Trp
130                 135                 140

Asn Thr Phe Val Glu Asn His Glu Arg Thr Phe Lys Ala Trp Glu Gly
145                 150                 155                 160

Leu His Glu Asn Ser Val Arg Leu Ser Arg Gln Leu Arg Arg Ile Leu
                165                 170                 175

Leu Pro Leu

<210> SEQ ID NO 63
<211> LENGTH: 173
<212> TYPE: PRT
<213> ORGANISM: Artificial Sequence
<220> FEATURE:
<223> OTHER INFORMATION: Synthetic construct

<400> SEQUENCE: 63

Thr Ser Asn Phe Asn Asn Gly Ile Gly Arg His Lys Thr Tyr Leu Cys
1               5                   10                  15

Tyr Glu Val Glu Arg Leu Asp Asn Gly Thr Ser Val Lys Met Asp Gln
                20                  25                  30

His Arg Gly Phe Leu His Asn Gln Ala Lys Asn Leu Leu Cys Gly Phe
            35                  40                  45

Tyr Gly Arg His Ala Glu Leu Arg Phe Leu Asp Leu Val Pro Ser Leu
50                  55                  60

Gln Leu Asp Pro Ala Gln Ile Tyr Arg Val Thr Trp Phe Ile Ser Trp
65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110

Asp Tyr Asp Pro Leu Tyr Lys Glu Ala Leu Gln Met Leu Arg Asp Ala
        115                 120                 125

Gly Ala Gln Val Ser Ile Met Thr Tyr Asp Glu Phe Lys His Cys Trp
    130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg
                165                 170

<210> SEQ ID NO 64
<211> LENGTH: 181
<212> TYPE: PRT
<213> ORGANISM: Artificial Sequence
<220> FEATURE:
<223> OTHER INFORMATION: Synthetic construct

<400> SEQUENCE: 64

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

-continued

```
Phe Ile Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Ala Gly Arg Arg Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145             150                 155                 160

Ala Trp Glu Gly Leu His Glu Asn Ser Val Arg Leu Ser Arg Gln Leu
            165                 170                 175

Arg Arg Ile Leu Leu
            180
```

COMPOSITIONS AND METHODS FOR DETECTION AND MEASUREMENT OF RNA MODIFICATIONS THROUGH TARGETED RNA EDITING

PRIOR RELATED APPLICATION

This application claims the benefit of and priority to U.S. Provisional Application No. 62/853,768 filed on May 29,2019, which is hereby incorporated by reference in its entirety

STATEMENT REGARDING FEDERALLY FUNDED RESEARCH

This invention was made with government support under Grant Nos. 1DP1DA046584-01 and 1R01MH118366-01 awarded by the National Institutes of Health/National Institute on Drug Abuse and National Institutes of Health/National Institute of Mental Health, respectively. The government has certain rights in the invention.

FIELD

This disclosure describes compositions and methods for detecting RNA modifications in cells and tissues.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1185352_seqlist.txt, created on May 27, 2020, and having a size of 49.4 KB and is filed concurrently with the specification. The sequence listing contained in this ASCII formatted document is part of the specification and is herein incorporated by reference in its entirety.

BACKGROUND $N^6$-methyladenosine ($m^6A$) is the most abundant internal ribonucleic acid (RNA) modification and has been implicated in nearly every aspect of the RNA life cycle. Moreover, proteins involved in the formation, removal, and recognition of $m^6A$ have emerged as critical regulators of a variety of physiological processes, ranging from stem cell proliferation to learning and memory. To date, methods for the detection of $m^6A$ have relied on immunoprecipitation of methylated RNAs using $m^6A$-recognizing antibodies. However, these methods suffer from several limitations. For example, $m^6A$ antibodies also recognize the structurally similar cap modification, $m^6Am$, so immunoprecipitation of methylated RNAs does not exclusively enrich for $m^6A$ containing RNA. Also, a large amount of input RNA is required for immunoprecipitation and library preparation, which makes global $m^6A$ detection prohibitive for limited quantity samples. Finally, antibody-based approaches are costly and the associated library preparation steps are time-consuming, which can be a limiting factor for many experiments.

SUMMARY

Provided herein are fusion proteins that can be used to edit RNA and detect $m^6A$ residues. The fusion proteins comprise an $N^6$-methyladenosine ($m^6A$) binding domain of a YT521-B homology (YTH) domain-containing protein fused to a catalytic domain of a cytidine deaminase or a catalytic domain of an adenosine deaminase. In some embodiments, the $m^6A$ binding domain is fused to the catalytic domain via a peptide linker.

In some embodiments, the $m^6A$ binding domain comprises a polypeptide having at least 95% identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

In some embodiments, the catalytic domain comprises a polypeptide having at least 95% identity to SEQ ID NO 12 or a catalytic fragment thereof, SEQ ID NO: 13 or a catalytic fragment thereof; SEQ ID NO: 14 or a catalytic fragment thereof; or SEQ ID NO: 15.

In some embodiments, the fusion protein further comprises a localization element. In some embodiments, the localization element is fused to the N-terminus or the C-terminus of the fusion protein.

Also provided is a recombinant nucleic acid encoding any of the fusion proteins described herein. Further provided is a DNA construct comprising a promoter operably linked to the recombinant nucleic acid. In some embodiments, the promoter is an inducible promoter. Also provided is a vector comprising a recombinant nucleic acid or DNA construct described. A host cell comprising a recombinant nucleic acid, DNA construct or vector described herein is also provided. In some embodiments, the host cell is a mammalian cell. Also provided is a non-human transgenic animal comprising a host cell described herein.

Also provided is a method for detecting $m^6A$ residues in the RNA produced by one or more cells comprising: (a) isolating RNA from one or more cells that expresses a fusion protein described herein; (b) amplifying one or more target sequences in the isolated RNA; and (c) sequencing the one or more target sequences to identify cytidine to uridine deamination at sites adjacent to $m^6A$ residues, thus detecting the $m^6A$ residues in the RNA of the one of more cells. In some embodiments, the recombinant nucleic acid encoding the fusion protein is introduced into the one or more cells prior to isolating RNA from the cell. In some embodiments, the fusion protein is stably or transiently expressed in the cell.

Also provided is a method for detecting $m^6A$ residues in the RNA produced by one or more cells comprising: (a) fixing a cell or tissue that expresses a fusion protein described herein; and (b) detecting cytidine to uridine deamination in the RNA, wherein cytidine to uridine deamination is detected via mutation-sensitive in situ hybridization.

Further provided is a method for detecting $m^6A$ residues in a biological sample comprising:(a) isolating RNA from a biological sample; (b) contacting the RNA with a fusion protein described herein; (c) amplifying one or more target sequences in the RNA; and (d) identifying cytidine to uridine deamination at sites adjacent to $m^6A$ residues in the one or more target sequences, thus detecting the $m^6A$ residues in the one or more target sequences.

Also provided is method for diagnosing a disease in a subject comprising: (a) isolating RNA from a biological sample; (b) contacting the RNA with a fusion protein described herein; (c) amplifying one or more target sequences in the RNA; and (d) identifying cytidine to uridine deamination at sites adjacent to $m^6A$ residues in the one or more target sequences to identify a pattern of $m^6A$ residues, a difference in the pattern of $m^6A$ residues as compared to a reference pattern of $m^6A$ residues from a reference population(s), indicating the subject has or is at risk for developing the disease.

Further provided is a method for determining the efficacy of a selected treatment for a disease in a subject comprising: (a) isolating RNA from a biological sample from the subject before the selected treatment; (b) contacting the RNA with the fusion protein as described above, (c) amplifying one or more target sequences in the RNA; (d) identifying cytidine to uridine deamination at sites adjacent to $m^6A$ residues to identify a pattern of $m^6A$ residues in the one or more target sequences; (e) treating the subject with the selected treatment, (f) isolating RNA from a biological sample from the subject at one or more times after administration of the selected treatment; (g) amplifying one or more target sequences in the RNA of step f); (h) identifying cytidine to uridine deamination at sites adjacent to $m^6A$ residues to identify a pattern of $m^6A$ residues in the one or more target sequences of step g); and (i) comparing the pattern of $m^6A$ residues identified in step (d) and (h) to determine whether the pattern of $m^6A$ residues is the same or whether the $m^6A$ residues detected in step (d) or (h) is more similar to a reference pattern, a pattern of $m^6A$ residues in step (h) more similar to the reference pattern indicating the selected treatment is effective for treating the disease in the subject.

In some embodiments, the disease is selected from the group consisting of cancer, an autoimmune disorder, a neurodegenerative disorder and a viral infection. In some embodiments, the biological sample is a biopsy. In some embodiments, the one or more target sequences are amplified by reverse transcriptase polymerase chain reaction (RT-PCR). In some embodiments, cytidine to uridine deamination is identified by sequencing the one or more target sequences. In some embodiments, the RNA comprises one or more RNAs selected from the group consisting of messenger RNA (mRNA), transfer RNA (tRNA), small nuclear RNA (snRNA), a regulatory RNA, a transfer-messenger RNA (tmRNA), ribosomal RNA (rRNA), microRNA (miRNA), long noncoding RNA (lncRNA) or circular RNA (circRNA).

Also provided is a kit comprising: (a) one or more fusion proteins described herein; and (b) one or more primers for amplification of one or more target RNA sequences.

DETAILED DESCRIPTION

Figure 1:
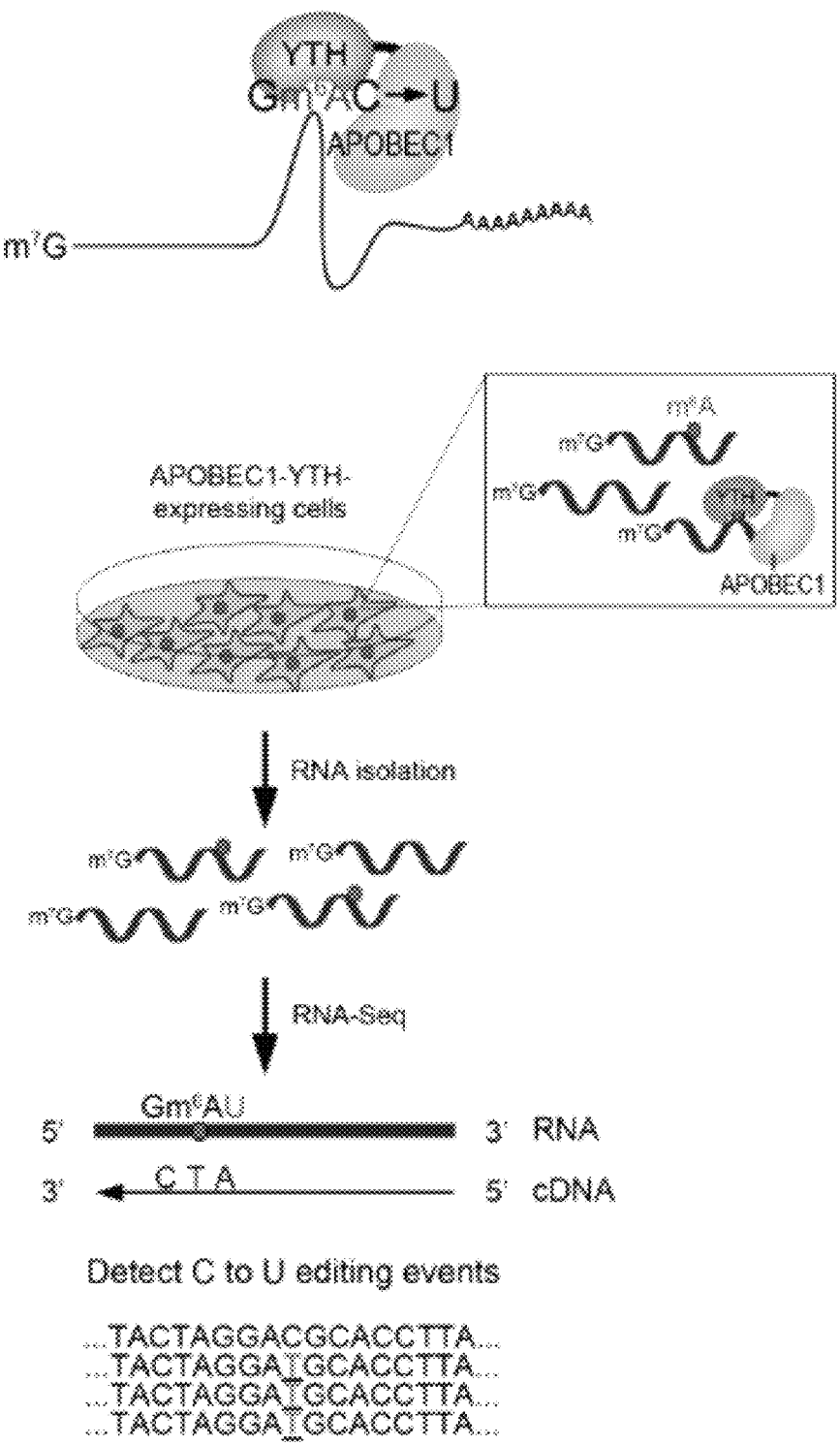
FIG. 1 shows a schematic of the DART-Seq (deamination adjacent to RNA modification targets) approach for $m^6A$ detection. APOBEC1 is fused to the YTH domain to guide Cytidine (C) to uridine (U) editing at cytidine residues adjacent to $m^6A$ sites. APOBEC1-YTH is expressed in cells and total RNA is isolated and subjected to RNA-Seq. C to U mutations are then detected to identify sites of $m^6A$. An unedited sequence is shown (TACTAGGACGCACCTTA) (SEQ ID NO: 56). Edited sequences are shown as (TACTAGGATGCACCTTA) (SEQ ID NO: 57).

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

I. Polynucleotides and Polypeptides

Provided in this disclosure are fusion proteins in which an $N^6$-methyladenosine ($m^6A$) binding domain of a YT521-B homology (YTH) domain-containing protein is fused to a catalytic domain of a cytidine deaminase or a catalytic domain of an adenosine deaminase. The fusion proteins bind to $m^6A$-containing RNA and exhibit nucleotide deaminase activity, for example cytidine deaminase activity or adenosine deaminase activity. The fusion protein converts cytidine or uridine, or adenosine to inosine, in RNA molecules, thereby allowing detection of $m^6A$ residues in RNA molecules.

Provided herein is a fusion protein comprising an $N^6$-methyladenosine ($m^6A$) binding domain of a YT521-B homology (YTH) domain-containing protein fused to a catalytic domain of a cytidine deaminase or a catalytic domain of an adenosine deaminase.

As used throughout, a "fusion protein" is a protein comprising two different polypeptide sequences, i.e. a binding domain and a catalytic domain, that are joined or linked to form a single polypeptide. The two amino acid sequences are encoded by separate nucleic acid sequences that have been joined so that they are transcribed and translated to produce a single polypeptide. In some embodiments, the fusion protein comprises, in the following order, an m⁶A binding domain, and a catalytic domain of a cytidine deaminase or an adenosine deaminase.

As used throughout, "m⁶A" refers to posttranscriptional methylation of an adenosine residue in the RNA of prokaryotes and eukaryotes (e.g., mammals, insects, plants and yeast).

As used throughout, an m⁶A binding domain of a YT521-B homology (YTH) domain-containing protein is a polypeptide fragment of a YTH domain-containing protein that binds to m⁶A-containing RNA. The m⁶A binding domain derived from a YT521-B homology (YTH) domain-containing protein can be of any size as long as it retains binding activity and is not the full-length YTH domain-containing protein. In some embodiments, the binding domain retains at least about 75%, 80%, 90%, 95%, or 99% of the binding activity of the wildtype YTH domain-containing protein from which the binding domain is derived.

In some embodiments, the the m⁶A binding domain comprises a polypeptide having at least 95% identity, for example, at least about 95%, 96%, 97%, 98% or 99% identity, to SEQ ID NO: 1 (amino acid sequence of YTHDF2-YTH, an m⁶A binding domain of YTHDF2), SEQ ID NO: 2 (amino acid sequence of YTHDF2-YTH_W432A_W486A, a mutated m⁶A binding domain of YTHDF2), SEQ ID NO: 3 (amino acid sequence of YTHDF2-YTHmut, an amino acid sequence that includes theYTH domain of YTHDF2, and does not include the m⁶A-binding domain), SEQ ID NO: 4 (amino acid sequence of YTHDF2-YTHmut, an amino acid sequence comprising SEQ ID NO: 3, with a W432A mutation and a W486a mutation), SEQ ID NO: 5 (amino acid sequence of YTHDF2-YTH D422N, a mutated m⁶A binding domain of YTHDF2), SEQ ID NO: 6 (amino acid sequence of an m⁶A binding domain of YTHDF1), SEQ ID NO: 7 (amino acid sequence of YTHDF lmut, an amino acid sequence that includes theYTH domain of YTHDF2, and does not include the m⁶A-binding domain), SEQ ID NO: 8 (amino acid sequence of YTHDF1 D401N, a mutated m⁶A binding domain of YTHDF1), SEQ ID NO: 9 (amino acid sequence of an m⁶A binding domain of YTHDF3); SEQ ID NO: 10 (amino acid sequence of an m⁶A binding domain of YTHDC1) or SEQ ID NO: 11 (amino acid sequence of an m⁶A binding domain of YTHDC2).

As used throughout, a catalytic domain of a cytidine deaminase is a polypeptide comprising a cytidine deaminase, for example, Apolipoprotein B MRNA Editing Enzyme Catalytic Subunit (APOBEC1), activation induced cytidine deaminase (AICDA) or Apolipoprotein B mRNA editing enzyme, catalytic polypeptide-like 3A (APOBEC3A), or a catalytic fragment thereof, that catalyzes deamination of cytidine ("C") to uridine ("U") in RNA molecules. As used throughout, a catalytic domain of an adenosine deaminase, is a polypeptide comprising an adenosine deaminase, for example, double-stranded RNA-specific adenosine deaminase (ADAR1), or a catalytic fragment thereof, that catalyzes deamination of adenosine ("A") to inosine ("I") in RNA molecules. In some embodiments, the catalytic domain retains at least about 75%, 80%, 90%, 95%, or 99% of the enzymatic activity of the wildtype deaminase from which the domain is derived.

In some embodiments, the catalytic domain comprises a polypeptide having at least 95% identity, for example, at least about 95%, 96%, 97%, 98% or 99% identity, to SEQ ID NO: 12 (amino acid sequence of rAPOBEC1) or its catalytic domain SEQ ID NO: 61, SEQ ID NO: 13 (amino acid sequence of hAICDA) or its catalytic domain (SEQ ID NO: 62); SEQ ID NO: 14 (amino acid sequence of hAPOBEC3A) or its catalytic domain (SEQ ID NO: 63); or SEQ ID NO: 15 (amino acid sequence of catalytic domain of ADAR1).

The catalytic domain can also comprise a polypeptide having at least 95% identity to SEQ ID NO: 64 (amino acid sequence of catalytic domain of AID-C12), as set forth in U.S. Patent Application Publication No. 20190010478.

In some embodiments, the m⁶A binding domain is fused to the catalytic domain via a peptide linker. The peptide linker can be about 2 to about 150 amino acids in length. For example, the linker can be a linker of from about 5 to about 20 amino acids in length, from about 5 to about 25 amino acids in length, from about 10 to about 30 amino acids in length, 5 to about 35 amino acids in length, from about 5 to about 40 amino acids in length, from about 5 to about 45 amino acids in length, from about 5 to about 50 amino acids in length, from about 5 to about 55 amino acids in length, from about 5 to about 60 amino acids in length, from about 5 to about 65 amino acids in length, from about 5 to about 70 amino acids in length, from about 5 to about 75 amino acids in length, from about 5 to about 80 amino acids in length, from about 5 to about 85 amino acids in length, from about 5 to about 90 amino acids in length, from about 5 to about 95 amino acids in length, from about 5 to about 100 amino acids in length, from about 5 to about 105 amino acids in length, from about 5 to about 110 amino acids in length, from about 5 to about 115 amino acids in length, from about 5 to about 120 amino acids in length, from about 5 to about 125 amino acids in length, from about 5 to about 130 amino acids in length, from about 5 to about 135 amino acids in length, from about 5 to about 140 amino acids in length, from about 5 to about 145 amino acids in length, or from about 5 to about 150 amino acids in length.

Exemplary peptide linkers include, but are not limited to, peptide linkers comprising SEQ ID NO: 16 (SGSETPGTS-ESATPE), SEQ ID NO: 17 (SGSETPGTSESATPES), SEQ ID NO: 18 ((GGGGS)₃), SEQ ID NO: 19 ((GGGGS)₁₀), SEQ ID NO: 20 ((GGGGS)₂₀), SEQ ID NO: 21 (A(EAAAK)₃A), SEQ ID NO: 22 (A(EAAAK)₁₀A), or SEQ ID NO: 23 (A(EAAAK)₂₀A).

In some embodiments, the fusion protein further comprises a localization element. In some embodiments, the localization element is fused to the N-terminus or the C-terminus of the fusion protein. As used herein, a localization element targets or localizes the fusion protein to one or more subcellular compartments. Subcellular compartments include but are not limited to, the nucleus, the endoplasmic reticulum, the mitochondria, chromatin, the cellular membrane, and RNA granules (for example, P-bodies, stress granules and transport granules). In some embodiments, the fusion protein can be targeted to the nuclear lamina, nuclear speckles nuclear paraspeckles in the nucleus of a cell. In some embodiments, the protein can be targeted to the outer mitochondrial membrane or the inner mitochondrial membrane.

Exemplary localization elements include, but are not limited to, a peptide comprising a nuclear localization signal, for example, SEQ ID NO: 24 (PKKKRKV), a peptide comprising a nuclear export signal, for example, SEQ ID NO: 25 (LPPLERLTL), a peptide comprising an endoplasmic reticulum targeting sequence, for example, SEQ ID NO: 26 (MDPVVVLGLCLSCLLLLSLWKQSYGGG), or SEQ ID NO: 60 (METDTLLLWVLLLWVPGSTGD), a peptide comprising a Myc tag, for example, SEQ ID NO: 27 (EQKLISEEDL), a peptide comprising a V5 tag, for example, SEQ ID NO: 28 (GKPIPNPLLGLDST) or SEQ ID NO: 29 (IPNPLLGLD), a peptide comprising a FLAG tag, for example, SEQ ID NO: 30 (DYKDDDDK), a peptide comprising a 3 X FLAG tag, for example, SEQ ID NO: 31 (DYKDHDGDYKDHDIDYKDDDDK) and a peptide comprising a DHFR destabilization domain, for example, SEQ ID NO: 32 (ISLIAALAVDHVIGMETVMPWNLPAD-LAWFKRNTLNKPVIMGRHTWESIGR-PLPGRKNIILSSQPSTDDRVTWVKSVDEAIAACGDV-PEIMVIGGGRVYEQFLPKAQKLYLTHIDAEVE GDTHFPDYEPDDWESVF SEFHDADAQNSHSYCFEIL-ERR).

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

Modifications to any of the polypeptides or proteins provided herein are made by known methods. By way of example, modifications are made by site specific mutagenesis of nucleotides in a nucleic acid encoding the polypeptide, thereby producing a DNA encoding the modification, and thereafter expressing the DNA in recombinant cell culture to produce the encoded polypeptide. Techniques for making substitution mutations at predetermined sites in DNA having a known sequence are well known. For example, M13 primer mutagenesis and PCR-based mutagenesis methods can be used to make one or more substitution mutations. Any of the nucleic acid sequences provided herein can be codon-optimized to alter, for example, maximize expression, in a host cell or organism. SEQ ID NOs: 58 and 59 are exemplary codon-optimized nucleic acids for expression and purification of APOBEC1-YTH and APOBEC1-YTHmut, respectively.

The amino acids in the polypeptides described herein can be any of the 20 naturally occurring amino acids, D-stereoisomers of the naturally occurring amino acids, unnatural amino acids and chemically modified amino acids. Unnatural amino acids (that is, those that are not naturally found in proteins) are also known in the art, as set forth in, for example, Zhang et al. "Protein engineering with unnatural amino acids," *Curr. Opin. Struct. Biol.* 23(4): 581-587 (2013); Xie et al. "Adding amino acids to the genetic repertoire," 9(6): 548-54 (2005)); and all references cited therein. B and γ amino acids are known in the art and are also contemplated herein as unnatural amino acids.

As used herein, a chemically modified amino acid refers to an amino acid whose side chain has been chemically modified. For example, a side chain can be modified to comprise a signaling moiety, such as a fluorophore or a radiolabel. A side chain can also be modified to comprise a new functional group, such as a thiol, carboxylic acid, or amino group. Post-translationally modified amino acids are also included in the definition of chemically modified amino acids.

Also contemplated are conservative amino acid substitutions. By way of example, conservative amino acid substitutions can be made in one or more of the amino acid residues, for example, in one or more lysine residues of any of the polypeptides provided herein. One of skill in the art would know that a conservative substitution is the replacement of one amino acid residue with another that is biologically and/or chemically similar. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

By way of example, when an arginine to serine is mentioned, also contemplated is a conservative substitution for the serine (e.g., threonine). Nonconservative substitutions, for example, substituting a lysine with an asparagine, are also contemplated.

Any of the polypeptides described herein can further comprise a detectable moiety, for example, a fluorescent protein or fragment thereof. Examples of fluorescent proteins include, but are not limited to, yellow fluorescent protein (YFP, for example, Venus), green fluorescent protein (GFP), and red fluorescent protein (RFP) as well as derivatives, for example, mutant derivatives, of these proteins. See, for example, Chudakov et al. "Fluorescent Proteins and Their Applications in Imaging Living Cells and Tissues," *Physiological Reviews* 90(3): 1103-1163 (2010); and Specht et al., "A Critical and Comparative Review of Fluorescent Tools for Live-Cell Imaging," *Annual Review of Physiology* 79: 93-117 (2017))

Any of the polypeptides described herein can further comprise an affinity tag, for example a polyhistidine tag ((His)$_6$), albumin-binding protein, alkaline phosphatase, an AU1 epitope, an AU5 epitope, a biotin-carboxy carrier protein (BCCP) or a FLAG epitope, to name a few. See, Kimple et al. "Overview of Affinity Tags for Protein Purification, *Curr. Protoc. Protein Sci.* 73: Unit-9.9 (2013).

Recombinant nucleic acids encoding any of the polypeptides described herein are also provided. For example, a recombinant nucleic acid encoding a polypeptide that has at least 95%, for example, at least about 95%, 96%, 97%, 98% or 99%, identity to any one of SEQ ID NOs 1-32 is also provided.

As used throughout, the term "nucleic acid" or "nucleotide" refers to deoxyribonucleic acids (DNA) or ribonucleic acids (RNA) and polymers thereof in either single- or double-stranded form. It is understood that when an RNA is described, its corresponding cDNA is also described, wherein uridine is represented as thymidine. Unless specifically limited, the term encompasses nucleic acids containing known analogues of natural nucleotides that have similar properties as the reference nucleic acid and are metabolized in a manner similar to naturally occurring nucleotides. A nucleic acid sequence can comprise combinations of deoxyribonucleic acids and ribonucleic acids. Such deoxyribonucleic acids and ribonucleic acids include both naturally occurring molecules and synthetic analogues. The polynucleotides of the invention also encompass all forms of sequences including, but not limited to, single-stranded forms, double-stranded forms, hairpins, stem-and-loop structures, and the like.

As used throughout, RNA can be messenger RNA (mRNA), transfer RNA (tRNA), small nuclear RNA (snRNA), a regulatory RNA, a transfer-messenger RNA (tmRNA), ribosomal RNA (rRNA), microRNA (miRNA), long noncoding RNA (lncRNA) or circular RNA (circRNA).

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The term "identity" or "substantial identity," as used in the context of a polynucleotide or polypeptide sequence described herein, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

II. Constructs and Vectors

Also provided is a DNA construct comprising a promoter operably linked to a recombinant nucleic acid described herein. A nucleic acid is "operably linked" when it is placed into a functional relationship with another nucleic acid sequence. Numerous promoters can be used in the constructs described herein. A promoter is a region or a sequence located upstream and/or downstream from the start of transcription that is involved in recognition and binding of RNA polymerase and other proteins to initiate transcription. The promoter can be a eukaryotic or a prokaryotic promoter. In some embodiments the promoter is an inducible promoter. In some embodiments, the promoter is a constitutive promoter.

The recombinant nucleic acids provided herein can be included in expression cassettes for expression in a host cell or an organism of interest. The cassette will include 5' and 3' regulatory sequences operably linked to a recombinant nucleic acid provided herein that allows for expression of the modified polypeptide. The cassette may additionally contain at least one additional gene or genetic element to be cotransformed into the organism. Where additional genes or elements are included, the components are operably linked. Alternatively, the additional gene(s) or element(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain a selectable marker gene. The expression cassette will include in the 5' to 3' direction of transcription: a transcriptional and translational initiation region (i.e., a promoter), a polynucleotide of the invention, and a transcriptional and translational termination region (i.e., termination region) functional in the cell or organism of interest. The promoters of the invention are capable of directing or driving expression of a coding sequence in a host cell. The regulatory regions (i.e., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention.

Additional regulatory signals include, but are not limited to, transcriptional initiation start sites, operators, activators, enhancers, other regulatory elements, ribosomal binding sites, an initiation codon, termination signals, and the like. See Sambrook et al. (1992) Molecular Cloning: A Laboratory Manual, ed. Maniatis et al. (Cold Spring Harbor Laboratory Press, Cold Spring Harbor, N.Y.) (hereinafter "Sambrook 11"); Davis et al., eds. (1980) Advanced Bacterial Genetics (Cold Spring Harbor Laboratory Press), Cold Spring Harbor, N.Y., and the references cited therein.

The expression cassette can also comprise a selectable marker gene for the selection of transformed cells. Marker genes include genes conferring antibiotic resistance, such as those conferring hygromycin resistance, ampicillin resistance, gentamicin resistance, neomycin resistance, to name a few. Additional selectable markers are known and any can be used.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be used.

Further provided is a vector comprising a nucleic acid or expression cassette set forth herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene (See generally, Sambrook et al. Molecular Cloning: A Laboratory Manual, 4$^{th}$ ed., Cold Spring Harbor Laboratory Press, Cold Spring Harbor, 2012). The vector, for example, can be a plasmid.

There are numerous *E. coli* expression vectors known to one of ordinary skill in the art, which are useful for the expression of a nucleic acid. Other microbial hosts suitable for use include bacilli, such as *Bacillus subtilis*, and other enterobacteriaceae, such as *Salmonella, Senatia*, and various *Pseudomonas species*. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. Additionally, yeast expression can be used. Provided herein is a nucleic acid encoding a polypeptide of the present invention, wherein the nucleic acid can be expressed by a yeast cell. More specifically, the nucleic acid can be expressed by *Pichia pastoris* or *S. cerevisiae*.

Mammalian cells also permit the expression of proteins in an environment that favors important post-translational modifications such as folding and cysteine pairing, addition of complex carbohydrate structures, and secretion of active protein. Vectors useful for the expression of active proteins in mammalian cells are known in the art and can contain genes conferring hygromycin resistance, genticin or G418 resistance, or other genes or phenotypes suitable for use as selectable markers, or methotrexate resistance for gene amplification. A number of suitable host cell lines capable of secreting intact human proteins have been developed in the art, and include CHO cells, HeLa cells, COS-7 cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc.

The expression vectors described herein can also include the nucleic acids as described herein under the control of an inducible promoter such as the tetracycline inducible promoter or a glucocorticoid inducible promoter. The nucleic acids of the present invention can also be under the control of a tissue-specific promoter to promote expression of the nucleic acid in specific cells, tissues or organs. Any regulatable promoter, such as a metallothionein promoter, a heat-shock promoter, and other regulatable promoters, of which many examples are well known in the art are also contemplated. Furthermore, a Cre-loxP inducible system can also be used, as well as a Flp recombinase inducible promoter system, both of which are known in the art.

Insect cells also permit the expression of the polypeptides. Recombinant proteins produced in insect cells with baculovirus vectors undergo post-translational modifications similar to that of wild-type mammalian proteins.

III. Cells and Transgenic Animals

As such, aspects of this disclosure include host cells and transgenic animals comprising the nucleic acid sequences described herein as well as methods of making such cells and transgenic animals.

A host cell comprising a nucleic acid or a vector described herein is provided. The host cell can be an in vitro, ex vivo, or in vivo host cell. Populations of any of the host cells described herein are also provided. A cell culture comprising one or more host cells described herein is also provided. Methods for the culture and production of many cells, including cells of bacterial (for example *E. coli* and other bacterial strains), animal (especially mammalian), and archebacterial origin are available in the art. See e.g., Sambrook, Ausubel, and Berger (all supra), as well as Freshney (1994) *Culture of Animal Cells, a Manual of Basic Technique*, 3$^{rd}$ Ed., Wiley-Liss, New York and the references cited therein; Doyle and Griffiths (1997) *Mammalian Cell Culture: Essential Techniques* John Wiley and Sons, NY; Humason (1979) *Animal Tissue Techniques*, 4$^{th}$ Ed. W.H. Freeman and Company; and Ricciardelli, et al., (1989) In vitro *Cell Dev. Biol.* 25:1016-1024.

The host cell can be a prokaryotic cell, including, for example, a bacterial cell. Alternatively, the cell can be a eukaryotic cell, for example, a mammalian cell. In some embodiments, the cell can be an HEK293T cell, a Chinese hamster ovary (CHO) cell, a COS-7 cell, a HELA cell, an avian cell, a myeloma cell, a *Pichia* cell, an insect cell or a plant cell. A number of other suitable host cell lines have been developed and include myeloma cell lines, fibroblast cell lines, and a variety of tumor cell lines such as melanoma cell lines. The vectors containing the nucleic acid segments of interest can be transferred or introduced into the host cell by well-known methods, which vary depending on the type of cellular host.

As used herein, the phrase "introducing" in the context of introducing a nucleic acid into a cell refers to the translocation of the nucleic acid sequence from outside a cell to inside the cell. In some cases, introducing refers to translocation of the nucleic acid from outside the cell to inside the nucleus of the cell. Various methods of such translocation are contemplated, including but not limited to, electroporation, nanoparticle delivery, viral delivery, contact with nanowires or nanotubes, receptor mediated internalization, translocation via cell penetrating peptides, liposome mediated translocation, DEAE dextran, lipofectamine, calcium phosphate or any method now known or identified in the future for introduction of nucleic acids into prokaryotic or eukaryotic cellular hosts. A targeted nuclease system (e.g., an RNA-guided nuclease, a transcription activator-like effector nuclease (TALEN), a zinc finger nuclease (ZFN), or a megaTAL (MT) (Li et al. *Signal Transduction and Targeted Therapy* 5, Article No. 1 (2020)) can also be used to introduce a nucleic acid, for example, a nucleic acid encoding a fusion protein described herein, into a host cell The CRISPR/Cas9 system, an RNA-guided nuclease system that employs a Cas9 endonuclease, can be used to edit the genome of a host cell or organism. The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, for example, Cas9, in complex with guide and activating RNA to recognize and cleave foreign nucleic acid. Guide RNAs having the activity of both a guide RNA and an activating RNA are also known in the art. In some cases, such dual activity guide RNAs are referred to as a single guide RNA (sgRNA).

As used herein, the term "Cas9" refers to an RNA-mediated nuclease (e.g., of bacterial or archeal orgin, or derived therefrom). Exemplary RNA-mediated nucleases include the foregoing Cas9 proteins and homologs thereof. Other RNA-mediated nucleases include Cpf1 (See, e.g., Zetsche et al., Cell, Volume 163, Issue 3, p759-771, 22 Oct. 2015) and homologs thereof Cas9 homologs are found in a wide variety of eubacteria, including, but not limited to bacteria of the following taxonomic groups: *Actinobacteria, Aquificae, Bacteroidetes-Chlorobi, Chlamydiae-Verrucomicrobia, Chlroflexi, Cyanobacteria, Firmicutes, Proteobacteria, Spirochaetes,* and *Thermotogae*. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci U.S.A. 2013 Sep. 24; 110(39):15644-9; Sampson et al., Nature. 2013 May 9; 497(7448):254-7; and Jinek, et al., Science. 2012 Aug. 17; 337(6096):816-21. Variants of any of the Cas9 nucleases provided herein can be optimized for efficient activity or enhanced stability in the host cell. Thus, engineered Cas9 nucleases are also contemplated. See, for example, "Slaymaker et al., "Rationally engineered Cas9 nucleases with improved specificity," Science 351 (6268): 84-88 (2016)).

Any of the fusion proteins described herein can be purified or isolated from a host cell or population of host cells. For example, a recombinant nucleic acid encoding any of the fusion proteins described herein can be introduced into a host cell under conditions that allow expression of the fusion protein. In some embodiments, the recombinant nucleic acid is codon-optimized for expression. After expression in the host cell, the fusion protein can be isolated or purified, for example, as described in the Examples, or using other purification methods known in the art. As used herein, the term "isolated" or "purified" means that the protein is substantially free of other components found in the cell.

Also provided is a non-human transgenic animal comprising a mammalian host cell that comprises a nucleic acid or a vector described herein described. Methods for making transgenic animals, include, but are not limited to, oocyte pronuclear DNA microinjection, intracytoplasmic sperm injection, embryonic stem cell manipulation, somatic nuclear transfer, recombinase systems (for example, Cre-LoxP systems, Flp-FRT systems and others), zinc finger nucleases (ZNFs), transcriptional activator-like effector nucleases (TALENs) and clustered regularly interspaced short palindromic repeat/CRISPR-associated protein 9 (CRISPR/Cas9). See, for example, Volobueva et al. *Braz. J. Med. Biol. Res.* 52(5): e8108 (2019)).

The term "transgenic animal" as used herein means an animal into which a genetic modification has been introduced by a genetic engineering procedure and in particular an animal into which has been introduced an exogenous nucleic add. That is the animal comprises a nucleic acid sequence encoding a fusion protein described herein, which is not normally present in the animal. Included are both progenitor and progeny animals. Progeny animals include animals which are descended from the progenitor as a result of sexual reproduction or cloning and which have inherited genetic material from the progenitor. Thus, the progeny animals comprise the genetic modification introduced into the parent. A transgenic animal may be developed, for example, from embryonic cells into which the genetic modification (e.g. exogenous nucleic acid sequence) has been directly introduced or from the progeny of such cells. The exogenous nucleic acid is introduced artificially into the animal (e.g. into a founder animal). Animals that are produced by transfer of an exogenous nucleic acid through breeding of the animal comprising the nucleic acid (into whom the nucleic acid was artificially introduced), which are progeny animals, are also included. Representative examples of non-human mammals include, but are not limited to non-human primates, mice, rats, rabbits, pigs, goats, sheep, horses, zebrafish and cows. A cell or a population of cells from any of the non-human transgenic animals provided herein is also provided.

The exogenous nucleic acid may be integrated into the genome of the animal or it may be present in an non-integrated form, e.g. as an autonomously-replicating unit, for example an artificial chromosome which does not integrate into the genome, but which is maintained and inherited substantially stably in the animal. the expression of a reporter protein is tissue-specific is contemplated for this invention. In some embodiments, the exogenous nucleic acid is under the control of a cell-specific or tissue-specific promoter. For example, transgenic animals that express a a fusion protein in specific cells or tissues can be produced by introducing a nucleic acid into fertilized eggs, embryonic stem cells or the germline of the animal, wherein the nucleic acid is under the control of a specific promoter which allows expression of the nucleic acid in specific types of cells or tissues. As used herein, a protein is expressed predominantly in a given tissue, cell type, cell lineage or cell, when 90% or greater of the observed expression occurs in the given tissue cell type, cell lineage or cell.

In some embodiments, the exogenous nucleic acid is under the control of an inducible promoter. Inducible promoter systems that can be used include the heat shock promoter (Halloran et al., *Development* 127 (9): 1953-60 (2000)), the tetracycline inducible system, the RU486/mifepristone inducible system and the ecdysone inducible system (Rossi and Blau, *Curr. Opin. Biotech.* 9: 451-456 0998)), to name a few. Inducible systems can also be used to allow expression of the fusion protein at designated times during development, expanding the temporal specificity of fusion protein expression in the transgenic animal.

IV. Methods

This disclosure also provides methods for detecting $m^6A$ residues in cellular RNA by using DART-Seq (deamination adjacent to RNA modification targets). The methods according to the present disclosure substantially improve the time and cost associated with global $m^6A$ detection and enables transcriptome-wide mapping of $m^6A$ in limited RNA samples, without the need for the use of $m^6A$ antibodies.

Provided herein is a method for detecting $m^6A$ residues in the RNA produced by one or more cells comprising: (a) isolating RNA from one or more cells that express a fusion protein described herein; (b) amplifying one or more target sequences in the isolated RNA; and (c) sequencing the one or more target sequences to identify cytidine to uridine deamination at sites adjacent to $m^6A$ residues, thus detecting the $m^6A$ residues in the RNA of the one or more cells. In some embodiments, the recombinant nucleic acid encoding the fusion protein is introduced into the one or more cells prior to isolating RNA from the cell. In some embodiments, the fusion protein is stably or transiently expressed in the cell, as described above.

In any of the methods provided herein, the RNA isolated from the one or more cells can be one or more RNAs selected from the group consisting of messenger RNA (mRNA), transfer RNA (tRNA), small nuclear RNA (snRNA), a regulatory RNA, a transfer-messenger RNA (tmRNA), ribosomal RNA (rRNA), microRNA (miRNA), long noncoding RNA (lncRNA) or circular RNA (circRNA). In some embodiments, the methods further comprise enriching the isolated RNA for one or more RNAs of interest. For example, and not to be limiting, the isolated RNA be enriched for mRNA by removing rRNA from the isolated RNA.

As used herein, the term "adjacent" refers to a site of C to U conversion, or A to I conversion, that is immediately next to an $m^6A$ residue, as well as a site that is near an $m^6A$ residue, for example, from about 1 to about 20 nucleotides upstream or downstream of an $m^6A$ residue. For example, about 1, 2, 3, 4, 5, 6, 7, 8, 9, 10, 11, 12, 13, 14, 15, 16, 17, 18, 19 or 20 nucleotides upstreatm or downstream of an $m^6A$ residue. Since C to U, or A to I conversions occur adjacent to $m^6A$ residues, the number and location of $m^6A$ residues in one or more RNA molecules of interest can be identified.

In some embodiments, $m^6A$ residues are detected in the transcriptome of one or more cells. As used herein, the term "transcriptome" refers to the set of all RNA transcripts, including coding and non-coding transcripts in a single cell or a population of cells. In some embodiments, the transcriptome of one or more cells can be analyzed under different conditions, for example, exposure of the one or more cells to a drug or a chemical.

It is understood that in any of the methods provided herein, a fusion protein that catalyzes cytidine to uridine deamination can be replaced with a fusion protein that catalyzes adenosine to inosine deamination to detect $m^6A$ residues in the RNA of the one of more cells.

In some embodiments, the RNA is isolated from a population of cells. In some embodiments, a population of cells is separated into individual compartments, for example, tissue culture wells, prior to isolation of RNA from single cells. In some embodiments the amount of isolated RNA used in the method is less than about 200 ng, 175 ng, 150 ng, 125 ng, 100 ng, 75 ng, 50 ng, 25 ng, 15 ng, 10 ng, 5 ng, 0.5 ng, 0.1 ng or 0.01 ng.

In any of the methods provided herein, the one or more cells can be prokaryotic or eukaryotic cells. In some embodiments, the eukaryotic cell is a mammalian cell, a plant cell or a yeast cell. In some embodiments, the cell is a primary cell. As used herein, the term "primary" in the context of a primary cell, or example, a primary stem cell refers to a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized directly without culturing or sub-culturing. In some cases, the primary cells are stimulated, activated, or differentiated. In some embodiments, the primary cells are neurons, brain cells or hematopoietic cells. In any of the methods described herein, the cell can be an in vitro, an ex vivo, or an in vivo cell.

In any of the methods described herein, the one or more target sequences can be amplified, for example, using reverse-transcriptase PCT (RT-PCR or RT-qPCR), to generate a cDNA that can be sequenced. In some embodiments, RNA-Seq is used for amplification and sequencing. In some embodiments, RNA-Seq is used for single cell sequencing or in situ sequencing of fixed tissue. See, Chu et al. "RNA sequencing: platform selection, experimental design, and data interpretation". *Nucleic Acid Therapeutics.* 22 (4): 271-4 (2012); and Lee et al. "Highly multiplexed subcellular RNA sequencing in situ". *Science.* 343 (6177): 1360-3 (2014). In some embodiments, targeted RNA-Seq is used for selecting and sequencing specific RNAs of interest. See, for example, Martin et al. "Targeted RNA Sequencing Assay to Characterize Gene Expression and Genomic Alterations," *J. Vis. Exp.* 114: 54090 (2016).

Other sequencing methods that can be used to identify cytidine to uridine (thymidine in cDNA), or adenosine to inosine conversions include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, Calif.), ion semiconductor sequencing, ligation sequencing, sequencing by synthesis (Illumina, San Diego, Calif.), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, tunneling currents DNA sequencing, and any other DNA sequencing method identified in the future. One or more of the sequencing methods described herein can be used in high throughput sequencing methods. As used herein, the term "high throughput sequencing" refers to all methods related to sequencing nucleic acids where more than one nucleic acid sequence is sequenced at a given time.

Also provided is a method for detecting $m^6A$ residues in the RNA produced by one or more cells comprising: (a) fixing a cell or tissue that expresses a fusion protein described herein; and (b) detecting cytidine to uridine deamination in the RNA, wherein cytidine to uridine deamination is detected via mutation-sensitive in situ hybridization. See, for example, Baker et al. "Robust RNA-based in situ mutation detection delineates colorectal cancer subclonal evolution," *Nature Communications* 8, Article number 1998 (2017). In some embodiments, the fusion protein is introduced into the cell under conditions that allow expression of the fusion protein prior to fixing the cell. In some embodiments, the cell or tissue is from an organism, for example, a transgenic animal described herein. In some embodiments, the cell or tissue is from a frozen sample, a formalin fixed sample or a paraffin-embedded specimen. In some embodiments, the cell or tissue is fixed and permeabilized. Methods for fixing and permeabilizing cells and tissues are known in the art. See, for example, Fernandez and Fuentes, "Fixation/Permeabilization: New Alternative Procedure for Immunofluorescence and mRNA In Situ Hybridization of Vertebrate and Invertebrate Embryos," *Developmental Dynamics* 242: 503-517 (2013).

Further provided is a method for detecting $m^6A$ residues in a biological sample comprising:(a) isolating RNA from a biological sample; (b) contacting the RNA with a fusion protein described herein; (c) amplifying one or more target sequences in the RNA; and (d) identifying cytidine to uridine deamination at sites adjacent to $m^6A$ residues in the one or more target sequences, thus detecting the $m^6A$ residues in the one or more target sequences.

As used herein, a biological sample is a sample derived from a subject and includes, but is not limited to, any cell, tissue, or biological fluid. The sample can be, but is not limited to, blood, plasma, serum, sputum, hair, cheek tissue, urine, saliva, bronchoalveolar lavage fluids, biopsy (e.g. tissue or cells isolated from organ tissue, for example, from lung, liver, kidney, skin etc.), vaginal secretion, nasal secretion, skin, gastric secretion, or bone marrow specimens.

As used throughout, by subject is meant an individual. The subject can be an adult subject or a pediatric subject. Pediatric subjects include subjects ranging in age from birth to eighteen years of age. Preferably, the subject is an animal, for example, a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Also provided is method for diagnosing a disease in a subject comprising: (a) isolating RNA from a biological sample; (b) contacting the RNA with a fusion protein described herein; (c) amplifying one or more target sequences in the RNA; and (d) identifying cytidine to uridine deamination at sites adjacent to $m^6A$ residues in the one or more target sequences to identify a pattern of $m^6A$ residues, a difference in the pattern of $m^6A$ residues as compared to a reference pattern of $m^6A$ residues from a reference population(s), indicating the subject has or is at risk for developing the disease. As used throughout, a reference pattern, i.e., a control pattern, provides the number and/or location of $m^6A$ residues in one or more target sequences that can be used for comparison of the pattern obtained from a biological sample. In some embodiments, the reference pattern of $m^6A$ residues in the one or more target sequences is from a subject or population(s) that does not have the disease. In some embodiments, the reference pattern of $m^6A$ residues in the one or more target sequences is from subject or a reference population that has been successfully treated for the disease. In some embodiments, the reference pattern of $m^6A$ residues in the one or more target sequences is from subject or a reference population that has a particular stage of the disease. In the methods set forth herein, the difference in the pattern of $m^6A$ residues can be an increase or a decrease in $m^6A$ residues. The difference in the pattern of $m^6A$ residues can also be a change in the presence or absence of $m^6A$ residues at different locations in the RNA. For example, methylation may occur at one or more adenosine residues in the one or more target sequences at different locations as compared to the reference pattern. In another example, methylation may not occur at one or more adenosine residues in the one or more target sequences as compared to the reference pattern.

Further provided is a method for determining the efficacy of a selected treatment for a disease in a subject comprising: (a) isolating RNA from a biological sample from the subject before the selected treatment; (b) contacting the RNA with the fusion protein described herein, (c) amplifying one or more target sequences in the RNA; (d) identifying cytidine to uridine deamination at sites adjacent to $m^6A$ residues to identify a pattern of $m^6A$ residues in the one or more target sequences; (e) treating the subject with the selected treatment, (f) isolating RNA from a biological sample from the subject at one or more times after administration of the selected treatment; (g) amplifying one or more target sequences in the RNA of step f); (h) identifying cytidine to uridine deamination at sites adjacent to $m^6A$ residues to identify a pattern of $m^6A$ residues in the one or more target sequences of step g); and (i) comparing the pattern of $m^6A$ residues identified in step (d) and (h) to determine whether the pattern of $m^6A$ residues is the same or whether the $m^6A$ residues detected in step (d) or (h) is more similar to a reference pattern, a pattern of $m^6A$ residues in step (h) more similar to the reference pattern indicating the selected treatment is effective for treating the disease in the subject.

In some embodiments, the reference pattern of $m^6A$ residues in the one or more target sequences is from a subject or population(s) that does not have the disease. In some embodiments, the reference pattern of m⁶A residues in the one or more target sequences is from subject or a reference population that has been successfully treated for the disease. In some embodiments, the reference pattern of m⁶A residues in the one or more target sequences is from subject or a reference population that has a particular stage of the disease that is indicative of improvement.

In the methods set forth herein, the similarity in the pattern of m⁶A residues can be a similarity in the number of m⁶A residues in the one or more target sequences as compared to a reference pattern. The similarity in the pattern of m⁶A residues can also be a similarity in the presence or absence of m⁶A residues at different locations in the RNA. For example, methylation may occur at one or more adenosine residues in the one or more target sequences, at the same location(s), as compared to the reference pattern. In another example, methylation may not occur at one or more adenosine residues in one or more target sequences, at the same location(s), as compared to the reference pattern.

In some embodiments, treatment comprises one or more therapies selected from the group consisting of surgery, radiation, drug(s), chemotherapy, hormone therapy, immunotherapy, targeted therapy, antiviral therapy, and a stem cell transplant.

In some embodiments, RNA is isolated about 8 hours, 12 hours, 24 hours, 48 hours, one week, two weeks, three weeks, four weeks, two months, three months, four months, five months, six months, one year, or two years after treatment. By monitoring the subject after treatment, an improvement as well as a relapse or flare of the disease can be detected. For example, if two years after successful treatment, the pattern of m⁶A residues from the subject is more similar to a reference pattern indicating disease or worsening of disease, this is indicative of a relapse.

In some embodiments, the disease is selected from the group consisting of cancer, an autoimmune disorder, a neurodegenerative disorder and a viral infection.

As used herein, cancer is a disease characterized by the rapid and uncontrolled growth of aberrant cells. Cancer cells can spread locally or through the bloodstream and lymphatic system to other parts of the body. In some embodiments, the cancer is a solid tumor. In some embodiments, the cancer is a blood or hematological cancer. Exemplary cancers include, but are not limited to, breast cancer, prostate cancer, ovarian cancer, glioblastoma, cervical cancer, skin cancer, pancreatic cancer, colorectal cancer, bladder cancer, endometrial cancer, renal cancer, liver cancer, brain cancer, lymphoma, leukemia (for example, acute myeloid leukemia), myeloma, lung cancer, and the like.

As used herein, an autoimmune disease is a disease where the immune system cannot differentiate between a subject's own cells and foreign cells, thus causing the immune system to mistakenly attack healthy cells in the body. Examples of autoimmune disorders include, but are not limited to, inflammatory bowel disease, multiple sclerosis, psoriasis, rheumatoid arthritis, systemic lupus erythematosus, Graves' disease, type 1 diabetes, Sjogren's syndrome, autoimmune thyroid disease, and celiac disease.

As used herein, a neurodegenerative disease is a disease characterized by progressive dying and loss of neurons in the central nervous system. Examples of neurodegenerative diseases include, but are not limited to, Alzheimer's disease, vascular dementia, Lewy body dementia, amyotrophic lateral sclerosis, Parkinson's disease, prion disease, motor neuron diseases, Huntington's disease, spinocerebellar ataxia, and spinal muscular dystrophy.

Examples of viral infections include, but are not limited to, infections caused by DNA and RNA viruses. Examples include, but are not limited to, human immunodeficiency virus I (HIV 1), influenza A, herpes virus, hepatitis B, hepatitis C, human papillomavirus, Zika virus, Simian Virus 40, Epstein-Barr virus, Rous sarcoma virus, adenovirus, severe acute respiratory syndrome (for example, SARS-CoV-2, the causative agent of COVID-19), and Middle East respiratory syndrome (MERS).

V. Kits

Also provided is a kit for the detection of RNA modifications in a cell or tissue. The kit comprises: (a) one or more fusion proteins described herein; and (b) one or more primers for amplification of one or more target RNA sequences. Instructions for use of the kit can also be included. In some embodiments, the components of the kit, for example, the one or more fusion proteins and/or the primers, can be in a composition.

Compositions comprising a fusion protein or primers for amplification of one or more target sequences are also provided. The compositions may further comprise a diluent, solubilizer and/or an emulsifier, to be used with the methods disclosed herein. Once the composition has been formulated, it can be stored in a container, for example, a sealed vial, as a solution, suspension, gel, emulsion, solid, or as a dehydrated or lyophilized powder. In certain embodiments, such formulations can be stored either in a ready-to-use form or in a form (e.g., lyophilized) that is reconstituted prior to use.

In some embodiments, the kit further comprises any reagents required for performing one-step or two-step RT-PCR, including but not limited to amplification buffers, nucleases, and dNTPs, including deoxyadenosine dATP, dCTP, dGTP, and dTTP.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1. APOBEC1-YTH Constructs for m⁶A detection

A. Materials and Methods

It was reasoned that a strategy which alters the sequence near methylation sites would enable m⁶A detection by RNA-seq and thus overcome the major limitations of current methods. The preferred consensus sequence for m⁶A contains an invariable cytidine residue immediately following the m⁶A site (Rm⁶ACH, where R=A or G; H=A, C, or U). APOBEC1 is a cytidine deaminase which targets DNA and RNA to induce cytidine to uridine (C to U) editing (Navaratnam, et al. The p27 catalytic subunit of the apolipoprotein B mRNA editing enzyme is a cytidine deaminase. *J Biol Chem* 268, 20709-20712 (1993)). Thus, it was reasoned that recruitment of APOBEC1 to m⁶A sites would enable deamination of the cytidine immediately following m⁶A residues. A novel approach was used to edit m⁶A-adjacent cytidines in RNAs by fusing APOBEC1 to the m⁶A-binding YTH domain and detecting subsequent editing events with RNA-Seq.

The following examples present the DART-Seq (deamination adjacent to RNA modification targets) approach for detecting m⁶A sites. The utility of this approach is demonstrated for detecting m⁶A sites in cellular RNAs using transcriptome-wide mapping with as little as 10 nanograms of total RNA as input. This strategy provides new insights into clustering of m⁶A residues within individual transcript isoforms. This approach substantially improves the time and cost associated with global m⁶A detection and will enable transcriptome-wide mapping in limited RNA samples.

APOBEC1-YTH Constructs. APOBEC1-YTH Constructs were generated by fusing APOBEC1 to the m⁶A-binding YTH domain of YTHDF2 (Wang et al. N6-methyladenosine-dependent regulation of messenger RNA stability. *Nature* 505, 117-120 (2014); and Schwartz et al. Perturbation of m6A Writers Reveals Two Distinct Classes of mRNA Methylation at Internal and 5' Sites. *Cell Rep* 8, 284-296 (2014)). (FIG. 1). YTH-HA was synthesized as a gene fragment (IDT), and YTH-HA or YTH$^{mut}$-HA were subsequently amplified using the YTH Fwd/YTH-HA Rev or YTH$^{mut}$ Fwd/YTH-HA Rev primers (below). The YTH-HA sequence comprised amino acids 385-579 of human YTHDF2 fused at its C-terminal end to the HA tag (YPYDVPDYA)(SEQ ID NO: 33). The YTH$^{mut}$-HA fusion lacked amino acids 385-409 comprising the m⁶A-binding region. These YTH-HA fusions were then inserted downstream of the rat APOBEC1 editing domain (APOBEC1) in the pCMV-APOBEC1 plasmid (Addgene plasmid #73019, Watertown, Mass.) using the XmaI and PmeI restriction sites. A 15 amino acid linker was present between the APOBEC1 domain and the YTH domain.

Antibodies. The following antibodies and concentrations were used: rabbit anti-HA (Cell Signaling (Danvers, Mass.); 3724S; 1:1000), rabbit anti-m⁶A (Abcam (Cambridge, UK); ab151230; 1:1000), HRP-conjugated goat anti-rabbit (Abcam; ab6721; 1:2500), HRP-conjugated sheep anti-mouse (GE Healthcare (Chicago, Ill.); 95017-554; 1:2500), mouse anti-β-actin (Genscript (Piscataway, N.J.); A00702; 1:5000), rabbit anti-METTL3 (Abcam; ab195352; 1:1000), rabbit anti-cleaved caspase 3 (Proteintech (Rosemont, Ill.); 25546-1-AP, 1:1000), AlexaFluor 488-conjugated goat anti-rabbit (Thermo-Fisher (Waltham, Mass.); A-21206; 1:1000).

Cells. HEK293T cells from the American Type Culture Collection (ATCC) were cultured at 37° C. using DMEM supplemented with 10% FBS. METTL3-depleted cell lines were generated by cloning a METTL3-targeting sgRNA sequence (5'-GGAGTTGATTGAGGTAAAGCG-3')(SEQ ID NO: 34) into the pSpCas9(BB)-2A-Puro (PX459) V2.0 plasmid (Addgene plasmid #62988). Plasmids were then transfected into HEK293T cells and stable cells were selected with puromycin. Validation of METTL3 depletion was performed with Western blot, RNA-Seq, and m⁶A immunoblotting. Camptothecin treatment was carried out for 5 hours at 37° C. using 6 μM final concentration of camptothecin (Sigma (St. Louis, Mo.)) from a 3 mM stock prepared in DMSO. Control cells were treated with the same volume of DMSO.

Cell viability measurements. HEK293T cells were transfected with APOBEC1-YTH and incubated for 24 hours at 37° C. Viability was assessed by trypan blue staining and manual counting of the proportion of viable cells compared to untransfected cells.

Differential gene expression analysis. Gene expression analysis was carried out using the deseq2 package (Love et al. *Genome Biol.* 15, 550 (2014)). mRNAs identified as being at least 2-fold increased/decreased in APOBEC1-YTH expressing cells relative to untransfected cells with a corrected p value <0.05 were reported.

Immunofluorescence. HEK293T cells were transfected with APOBEC1-YTH and fixed 24 h later using 4% paraformaldehyde. Cells were then permeabilized in 0.1% Triton X-100 in PBS and blocked in 1% BSA/PBS for 15 min at 25° C. Rabbit anti-HA antibody was added overnight at 4° C. After 3×5 min washes in 1×PBS, secondary antibody (AlexaFluor488-conjugated goat anti-rabbit (Thermo Fisher), 1:1000) was then added for 1 h at 25° C. Cells were washed again in 1×PBS and incubated in DAPI solution (1:10000 in PBS) for 2 min. Images were acquired on a Leica DMi8 inverted fluorescence microscope.

m⁶A immunoblotting. Equal amounts of total RNA were separated by agarose gel electrophoresis for 1 h at 70V. RNA was then transferred to a Hybond nylon membrane for 2 h using downward transfer with Ambion NorthernMax/Gly transfer buffer. Membranes were then crosslinked using a handheld UV lamp for 1 min with 254 nm light. Membranes were blocked for ≥30 min with 5% nonfat dry milk in 0.1% PBST and probed with anti-m⁶A antibody overnight at 4° C. Secondary antibody (HRP-goat anti-rabbit; 1:2500) was added for 1 h in blocking buffer and blots were developed with ECL (Amersham ECL Prime (Little Chalfont, UK)) and imaged using the BioRad Chemidoc imaging system.

m⁶A immunoprecipitation (MeRIP). 30 μg of total RNA was fragmented using Ambion 10× fragmentation reagent at 70° C. for 7 min. 1.5 ul of the fragmentation reaction was saved as input. The remainder was subjected to m⁶A immunoprecipitation by first coupling 12 μl of m⁶A antibody to 50 μl of Protein A/G magnetic beads (Pierce (Dallas, Tex.)) in 300 μl of IP buffer (10 mM Sodium Phosphate, 0.05% Triton-X 100, 140 mM NaCl) for 2 h at 4° C., rotating. Beads were then washed three times in IP buffer, and RNA was denatured for 5 min at 75° C. followed by 2-3 minute incubation on ice. RNA was then coupled with antibody-bound beads in 300 μl IP buffer for 2 h at 4° C., rotating. Beads were washed five times in 500 μl IP buffer and eluted in 300 μl elution buffer (5 mM Tris-HCl, pH 7.5, 1 mM EDTA, pH 8.0, 0.05% SDS, 4.2 μl Proteinase K (20 mg/ml; Thermo)) for 1.5 h at 50° C. while mixing. RNA was then collected with phenol:chloroform extraction and ethanol precipitation.

RT-qPCR. RNA was reverse transcribed using Superscript III with random hexamers according to the manufacturer's instructions (Thermo). cDNA was then used for quantitative PCR using the indicated primers and iQ SYBR Green Super Mix (Bio-Rad) in an Eppendorf RealPlex thermocycler. RNA levels were determined using the ΔΔCt method and were normalized to GAPDH levels (MeRIP-RT-qPCR) or ACTB levels (mRNA abundance).

Western blotting. Protein was loaded in a NuPAGE 4-12% Bis-Tris precast gel (Thermo) and separated at 180V. Transfers were carried out at 105V for 90 min to a Hybond PVDF membrane. Blocking was carried out for ≥30 min in 5% nonfat dry milk/0.1% PBST and antibodies were added overnight in 0.1% PBST at 4° C. Secondary antibodies were incubated on membranes in blocking buffer for 1 h at room temperature. ECL reagent (Amersham ECL Prime) was mixed 1:1 and added to the membranes, which were imaged using the BioRad Chemidoc imaging system.

RNA pulldown assays. RNA pulldowns were performed as previously described[4]. Briefly, 5 μg of bait RNA which contained a single A or m$^6$A residue (5'-biotin-GUUC-UUCUGUGGACUGUG-3')(SEQ ID NO: 35) was bound to pre-washed streptavidin agarose beads (Sigma-Aldrich (St. Louis, MO)) in 200 μl binding buffer (10 mM Tris-HCl, pH 7.5, 1.5 mM MgCl$_2$, 150 mM KCl, 0.5 mM DTT, 0.05% (v/v) NP-40) at 4° C. for 1 h on a rotator. Beads were then washed twice with 0.5 mL binding buffer. Protein lysates were isolated from HEK293T cells transfected with APOBEC1-YTH or APOBEC1-YTH$^{mut}$ for 24 h by adding lysis buffer (10 mM NaCl, 2 mM EDTA, 0.5% Triton X-100, 0.5 mM DTT, 10 mM Tris-HCl, pH 7.5, complete mammalian protease inhibitor cocktail (Sigma) and phosphatase inhibitor cocktail 2 (Sigma)). Cells were lysed by 30 strokes of dounce homogenization and then centrifuged at 10,000×g at 4° C. for 15 min. Supernatants were collected and pre-cleared by mixing with streptavidin agarose beads at 4° C. for 1 hour on a rotator. Beads were pelleted at 6,500 rpm for 1 min and supernatants were then mixed with binding buffer. Approximately 1 mg of lysate was mixed with 10 μl of RNasin (Promega) and then added to RNA-bound beads for 30 minutes at room temperature, followed by a 2 h incubation at 4° C. on a rotator. Beads were washed five times (6,500 rpm, 4° C.) in binding buffer and proteins were eluted (60° C., 850 rpm for 30 minutes in a thermomixer) using elution buffer (50 mM Tris-HCl, pH 8.0, 200 mM NaCl, 2% SDS, 1 mM biotin). Samples were spun down at 6,500 rpm for 1min at room temperature, and eluates were collected and mixed 1:1 with 2×NuPAGE sample buffer containing 2.5% μ-mercaptoethanol and analyzed via western blot.

In vitro transcription. RNA was synthesized using the HiScribe T7 in vitro transcription kit (New England Biolabs). 1 μg of purified PCR product was used for each reaction. Transcription was carried out overnight at 42° C. using either ATP or N$^6$-meATP (Trilink (San Diego, Calif.). For experiments using varying amounts of m$^6$A within an RNA, transcripts synthesized using all ATP or all N$^6$-meATP were mixed in the indicated proportions.

In vitro deaminase assays. APOBEC1-YTH-HA and APOBEC1-YTHmut-HA proteins were in vitro transcribed/translated using the Promega TNT T7 Quick Coupled In Vitro Transcription/Translation kit. Briefly, 1 μg of plasmid DNA was used in a 50 μl reaction and incubated for one hour at 30° C. 5 μl of each reaction was then mixed with 30 ng of a 1500 nt-long RNA with a single internal A or m$^6$A site, 0.5 μl RNasin (Promega (Madison, Wis.)), in 1×deaminase buffer (10 mM Tris-HCl pH7.5, 50 mM KCl, 0.1 uM ZnCl$_2$). Reactions were incubated for 4 h at 37° C. RNA was isolated with the Qiagen RNeasy Plus Mini kit and treated with DNase I (New England Biolabs) for 15 min at 37° C. For assays using cellular RNA, in vitro deamination was carried out for 6 h at 37° C. using 50 ng of total RNA from HEK293T cells. Sequencing libraries were then prepared using the NebNext Ultra II Directional RNA Library Prep Kit for Illumina (New England Biolabs (Ipswich, Mass.)).

cDNA synthesis and Sanger sequencing. 1 μg purified RNA from in vitro deamination assays or from cells expressing APOBEC1-YTH or APOBEC1 alone was used for cDNA synthesis using either a 1:1 mix of oligo(dT) and random hexamers or gene specific primers (below). cDNA synthesis was carried out using the SuperScript III reverse transcriptase kit according to manufacturer's instructions (Thermo). PCR was then performed using Phusion High-Fidelity PCR Mastermix (New England Biolabs) and primers flanking m$^6$A target regions. Purified PCR products were then either directly sequenced using Sanger sequencing or cloned into the pCR Blunt II TOPO vector (Thermo). For direct Sanger sequencing, measurements of C to U conversion were quantified from Sanger sequencing traces by calculating the height of T sequence peaks relative to C sequence peaks at individual mixed (C/T) sites. For TOPO cloning, a minimum of three individual clones were selected for each condition, and a representative Sanger sequencing trace for each is shown. Sequencing primers were used as indicated and comprised the sequences listed below.

Primers (5'-3'). The primers used in these studies are listed in the table below.

| | |
|---|---|
| YTH Fwd | AGACTCCCGGGACCTCAGAG (SEQ ID NO: 36) |
| YTH$^{mut}$ Fwd | ACTCCCGGGACCTCAGAGTCCGCCACACCAGAAGGCCGGGTTTTCATCATTAAG (SEQ ID NO: 37) |
| YTH-HA Rev | CGGGTTTAAACTCAGGCGTAGTC (SEQ ID NO: 38) |
| BSG RT primer | GTGGGGGCGATCTTTATTGTGGCGG (SEQ ID NO: 39) |
| ACTB RT primer | TGTGCAATCAAAGTCCTCGGCCAC (SEQ ID NO: 40) |
| BSG Fwd/Sanger | GCCAATGCTGTCTGGTTGCGCC (SEQ ID NO: 41) |
| BSG Rev | GGAGGCTTCTGCGGTTCTGGAG (SEQ ID NO: 42) |
| ACTB Fwd/Sanger | CAGCAAGCAGGAGTATGACGAGTC (SEQ ID NO: 43) |
| ACTB Rev | CATGCCAATCTCATCTTG (SEQ ID NO: 44) |
| ACTB MeRIP Fwd | CATGTACGTTGCTATCCAGGC (SEQ ID NO: 45) |

| | |
|---|---|
| ACTB MeRIP Rev | CTCCTTAATGTCACGCACGAT (SEQ ID NO: 46) |
| ATRX MeRIP Fwd | CGAAGATCCCCACGTGTAAAGACTAC (SEQ ID NO: 47) |
| ATRX MeRIP Rev | CATCCTGCTCACCTCTTTGAGG (SEQ ID NO: 48) |
| BPTF MeRIP Fwd | GTGTTAGATGATGTCTCCATTCGGAG (SEQ ID NO: 49) |
| BPTF MeRIP Rev | CACTTTCCTCCTGTATGAGCGG (SEQ ID NO: 50) |
| Single A 1500 nt RNA RT primer | GCCAAGAGGCAACACACCAAC (SEQ ID NO: 51) |
| Single A 1500 nt RNA Fwd | CGGTTTCTCTCGGTCTGTTTTCC (SEQ ID NO: 52) |
| Single A 1500 nt RNA Rev | CAGAAGGCGACAACACAGCAACACC (SEQ ID NO: 53 |

Next-generation sequencing. All sequencing was performed by the Duke University Sequencing and Genomic Technologies Core facility. HEK293T cells were transfected with APOBEC1-YTH, APOBEC1-YTH$^{mut}$, or APOBEC1 alone using FuGENE HD according to the manufacturer's instructions (Promega). After 24 h, total RNA was isolated with TRIzol (Thermo) and subjected to DNase I treatment using RNase-free DNaseI (Sigma) for 20 min at 37° C. 1 μg of total RNA was then used for sequencing library preparation using the NebNext Ultra II Directional RNA Library Prep Kit for Illumina (New England Biolabs). For low-input samples, the Single Cell/Low Input RNA Library Prep Kit (New England Biolabs) was used with either 10 ng or 100 ng of total RNA as input as indicated. It was not necessary to remove rRNA prior to sequencing library preparation, although doing so may potentially be used to further increase the efficiency of C to U mutation detection. Prior to sequencing, samples were barcoded using NEBNext Multiplex Oligos for Illumina (New England Biolabs). Libraries were then sequenced on the Illumina Hi Seq 4000. For PacBio sequencing, 1 μg of RNA was used for library preparation using the Iso-Seq system. Two samples were sequenced on one SMRT cell of the PacBio Sequel instrument (Menlo Park, Calif.) and processed using the Iso-Seq analysis pipeline.

C to U editing site analysis. Sequencing reads were demultiplexed, adapters were removed, and strand-specific reads were reverse-complemented and aligned to the human genome (hg19) using Novoalign. PCR duplicates were collapsed, and individual C to U mutations were identified using CIMS (Shah et al. CLIP Tool Kit (CTK): a flexible and robust pipeline to analyze CLIP sequencing data. *Bioinformatics* 33, 566-567 (2017)) C to U sites identified with the p<1 threshold were further filtered, and only those sites that had a minimum of 2 mutations, at least 10 reads per replicate, and a mutation/read (m/k) threshold of 10-60% (for high-stringency lists) were kept. It was found that adjusting the number of mutations, reads per replicate, and m/k threshold is a good way to increase/decrease stringency of m$^6$A site calls to a desired level. If desired, sites can be further filtered to include only C to U editing events which are immediately preceded by an A; however, this could potentially exclude some m$^6$A sites for which editing occurs at a nearby C instead of the immediately adjacent C. In addition to these filtering steps, known mutations in the human genome (dbSNP 150), as well as endogenous C to U editing sites identified by sequencing of wild type HEK293T cells, were also removed. For APOBEC1-YTH or APOBEC1-YTH$^{mut}$ expressing cells, the list of C to U editing sites was further processed by removing sites detected in cells expressing APOBEC1 alone. For determining enrichment of C to U editing between samples, a filter of m/k was used to find sites that were of the indicated fold-enrichment greater than the reference sample. PacBio datasets were aligned to the human genome (hg19) using GSNAP (Wu et al. GMAP: a genomic mapping and alignment program for mRNA and EST sequences. *Bioinformatics* 21, 1859-1875 (2005)).and subjected to the same pipeline as above to identify C to U sites. In vitro DART-Seq datasets were also subjected to the same C to U mutation analysis using a m/k filtering threshold of 5-60%.

Exon length measurements. Exon length was determined using the RefSeq hg19 annotation. Sequencing reads spanning individual exons were processed by removing first and last exons, according to the consensus RefSeq annotation. In cases where reads overlapped with multiple isoforms and therefore different exons, the consensus Refseq sequence was used.

Metagene and motif analyses. Metagene analysis was performed using hg19 annotations according to previously published methods (Olarerin-George et al. MetaPlotR: a Perl/R pipeline for plotting metagenes of nucleotide modifications and other transcriptomic sites. *Bioinformatics* 33, 1563-1564 (2017)). Discovery of enriched motifs was performed using HOMER (Heinz et al. Simple combinations of lineage-determining transcription factors prime cis-regulatory elements required for macrophage and B cell identities. *Mol Cell* 38, 576-589 (2010)) using sequences spanning a region 4 nucleotides up- and downstream of C to U editing sites as input.

Replicates analysis. Independent biological replicates of global DART-Seq experiments were compared by computing the Pearson correlation coefficient between the number of C to U mutations per gene between any two replicate experiments.

Calculating C to U editing events in individual reads. To determine the number of reads with one or more C to U editing events out of all reads that spanned at least two called C to U editing events, Sam2Tsv (Lindenbaum jVarkit:java-based utilities for Bioinformatics (2015)) for was used to identify individual reads containing C to U mutations. The first and last position of each read was then used in conjunction with bedtools intersect (Quinlan and Hall, I.M. BEDTools: a flexible suite of utilities for comparing genomic features. *Bioinformatics* 26, 841-842 (2010)) to find reads that overlap more than one C to U editing site from our final list of high-confidence sites. The number of editing events within these reads was then counted and summed.

Dataset comparisons. DART-Seq and $m^6A$ immunoprecipitation (MeRIP-Seq, miCLIP) datasets were analyzed using the closest and intersect features of the bedtools suite. For comparison of methylated mRNAs, bed file coordinates were annotated using the annotation feature of the metagene analysis pipeline (above) to give individual mRNAs, which were then compared between datasets.

Statistics. Statistical analysis of cell viability and western blot data were performed using a two-tailed t-test. Analysis of C to U editing enrichment in various transcript regions following CPT treatment, as well as analysis of the proportion of C to U sites following each nucleotide, was performed using a chi-squared test.

B. Results

1. APOBEC1-YTH Converts $m^6A$ Adjacent Cytidine to Uridine

The APOBEC1-YTH fusion protein was incubated with a synthetic RNA containing a single internal adenosine. Reverse transcription and Sanger sequencing indicated frequent editing of the cytidine immediately following $m^6A$ in methylated RNA, but not in unmethylated RNA. APOBEC1-YTH$^{mut}$, which lacks the $m^6A$-binding portion of the YTH domain, failed to convert C to U in $m^6A$-containing RNA.

Figure 2:
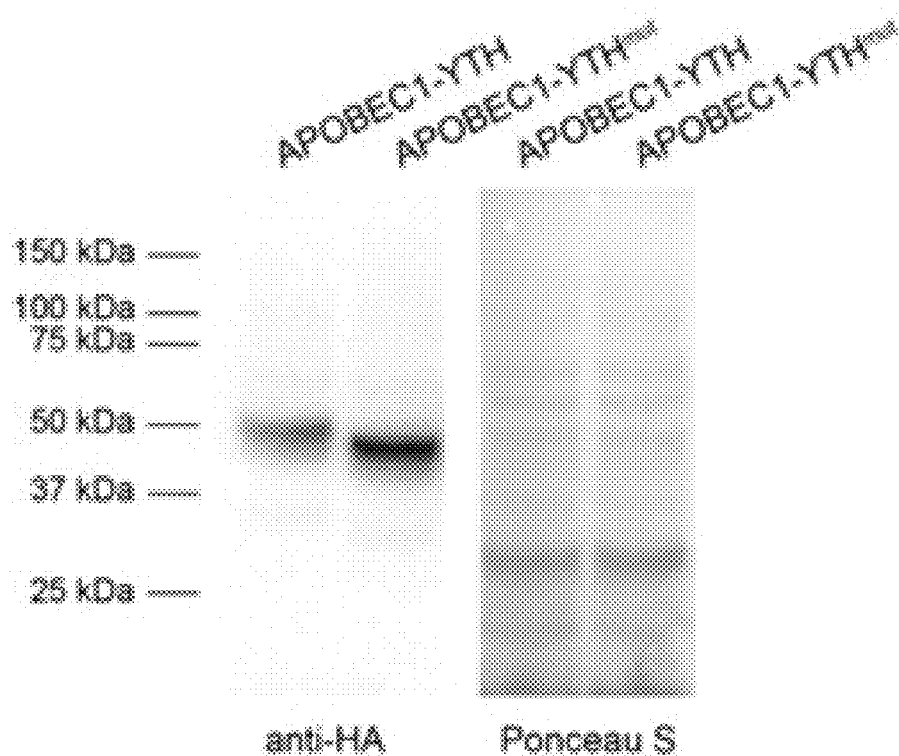
FIG. 2 shows western blot results for anti-HA indicating the levels of APOBEC1-YTH or APOBEC1-YTH$^{mut}$ in in vitro DART-Seq assays. APOBEC1-YTH or APOBEC1-YTH$^{mut}$ proteins were synthesized in vitro and an aliquot equivalent to the amount used for DART-Seq assays was removed and subjected to western blot analysis. General protein levels are also shown using ponceau S staining of the membrane. Images are representative of n=2 independent experiments.
Figure 3:
FIG. 3 shows APOBEC1-YTH$^{mut}$ exhibiting substantially reduced binding to $m^6A$ in RNA pulldown assays. Anti-HA western blot results are shown after mixing HA-tagged APOBEC1-YTH or APOBEC1-YTH$^{mut}$ with A- or $m^6A$-containing biotinylated RNA and subsequently purifying RNA-bound protein with streptavidin pulldown. 2% of input is shown as a reference. Blots are representative of n=2 independent experiments.

To confirm that the observed editing was caused by targeting of APOBEC1 to the $m^6A$ residue, the in vitro deamination assays was repeated using a mutant version of the APOBEC1-YTH fusion protein (APOBEC1-YTH$^{mut}$) in which the $m^6A$ binding region of the YTH domain was deleted (FIG. 2). APOBEC1-YTH$^{mut}$ was impaired in its ability to bind $m^6A$ (FIG. 3) and failed to convert adjacent cytidines to uridines in $m^6A$-containing RNA indicating that the deaminase activity of APOBEC1-YTH is directed by the $m^6A$-binding activity of the YTH domain.

2. DART-Seq Enables Transcriptome-Wide Detection of m6A

To determine whether APOBEC1-YTH could be used to detect endogenous $m^6A$ sites in cells, DART-Seq (deamination adjacent to RNA modification targets) was developed, in which APOBEC1-YTH was introduced into cells and then total RNA was subjected to next-generation sequencing followed by C to U mutation detection (FIG. 1). Comparison of three biological replicates indicated high reproducibility in C to U mutations in APOBEC1-YTH-expressing HEK293T cells, suggesting that APOBEC1-YTH targets specific RNAs for editing with high consistency across samples.

To determine whether DART-Seq can identify $m^6A$ residues, C to U editing sites from cells expressing APOBEC1-YTH were compared to cells expressing APOBEC1 alone. DART-Seq editing events from APOBEC1-YTH-expressing cells occurred primarily in the 3'UTR and coding sequence (CDS) and were enriched in the vicinity of the stop codon which mirrors the distribution of $m^6A$. In contrast, editing events from cells expressing APOBEC1 alone were located primarily in 3'UTRs and intergenic regions and failed to show an enrichment near the stop codon. Furthermore, there was little overlap in C to U editing between the two datasets, as 96% of edited sites from APOBEC1-YTH-expressing cells were not detected in cells expressing APOBEC1 alone (56,603 out of 59,246 sites)

Figure 4:
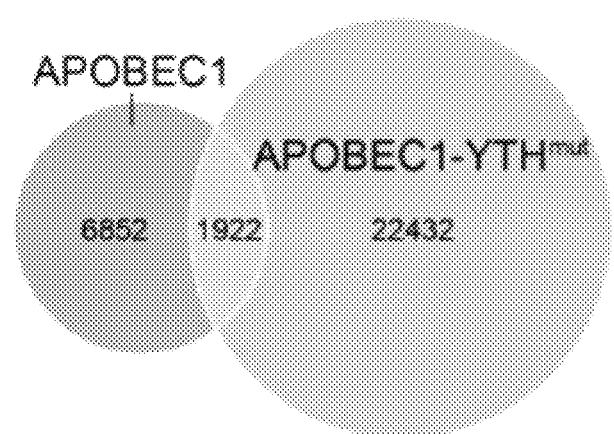
FIG. 4 shows a Venn diagram illustrating overlapping C to U editing sites in DART-Seq libraries were prepared from cells expressing APOBEC1-YTH$^{mut}$ or APOBEC1 alone.

To further ensure that C to U editing was caused by recruitment of APOBEC1-YTH to $m^6A$, RNA-seq on HEK293T cells expressing APOBEC1-YTH$^{mut}$ was performed and the same C to U editing analysis carried out. C to U editing events in cells expressing APOBEC1-YTH$^{mut}$ showed a distinct distribution compared to those in cells expressing APOBEC1-YTH, characterized by an enrichment throughout the 3'UTR as opposed to in the vicinity of the stop codon (FIG. 4) Together, these results suggest that the specificity of APOBEC1-YTH editing throughout the transcriptome depends on its ability to bind $m^6A$.

To obtain a set of high-confidence editing sites, the list of APOBEC1-YTH sites was filtered to include only those with at least a 1.5-fold enrichment over APOBEC1-YTH$^{mut}$ samples. All naturally occurring C to U mutations in HEK293T cells were also excluded, as well as C to U editing sites detected in cells expressing APOBEC1 alone. This resulted in a list of 100,636 C to U editing sites in 9,793 RNAs that occurred in at least 5% of all reads. Of these, a stringent list of 40,263 editing events in 7,707 RNAs was observed in at least 10% of all reads.

Figure 5:
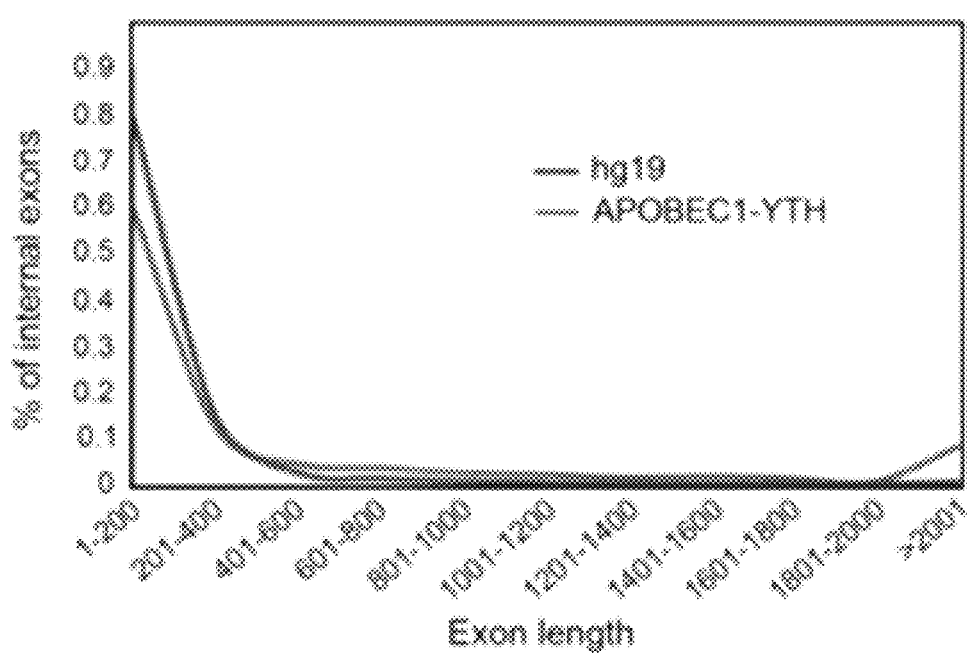
FIG. 5 shows the distribution of exon lengths for internal exons containing C to U editing sites in APOBEC1-YTH-expressing cells. Exon lengths of internal exons from the human genome (hg19 annotation) are shown for comparison. There is a greater proportion of long internal exons among C to U edited exons in APOBEC1-YTH-expressing cells compared to the natural distribution throughout the transcriptome.

Examination of sequences immediately surrounding DART-Seq sites revealed enrichment of a GGACU-containing motif, which matches the preferred consensus sequence for $m^6A$. In contrast, motifs detected in APOBEC1-YTH$^{mut}$ and APOBEC1 samples did not match the $m^6A$ consensus. Furthermore, DART-Seq sites were highly enriched within 3'UTRs and in the vicinity of the stop codon, as well as within long internal exons (FIG. 5), which matches the distribution of $m^6A$. Comparison of methylated RNAs detected by MeRIP-Seq and those identified by DART-Seq showed a high degree of overlap, with 64% of $m^6A$-containing RNAs detected by DART-Seq (3,679 of 5,768 RNAs). Examination of individual RNAs showed that DART-Seq editing events occurred at sites of MeRIP-Seq enrichment. Furthermore, consistent with the in vitro deamination assays, C to U editing events frequently occurred immediately downstream of known $m^6A$ sites in cellular RNAs.

3. Comparison Between DAR1:-Seq and Antibody-Based Approaches

Figure 6A:
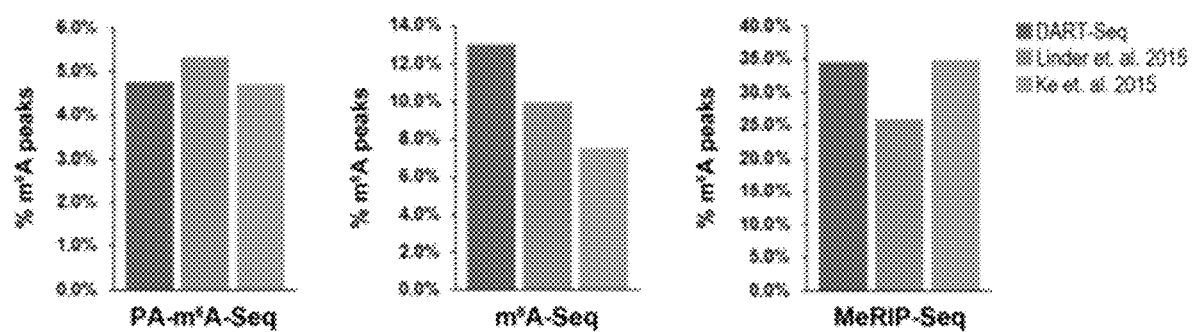
FIG. 6A shows results of immunoprecipitation-based $m^6A$ mapping from three different datasets (PA-$m^6A$-Seq15, $m^6A$-Seq4, and MeRIP-Seq3) where DART-Seq sites were compared to $m^6A$ peak regions. In addition, CIMS/CITS sites from two single-nucleotide resolution miCLIP datasets5,6 were also compared to $m^6A$ peak regions from the three datasets. Shown is the overlap between DART-Seq (left column for each dataset) and the two miCLIP datasets (middle and right columns for each dataset) reported as the percentage of $m^6A$ peak sites that overlap. Across all three datasets (PA-$m^6A$-Seq, $m^6A$-Seq, and MeRIP-Seq), DART-Seq performs similarly to miCLIP in identifying $m^6A$ sites.
Figure 6B:
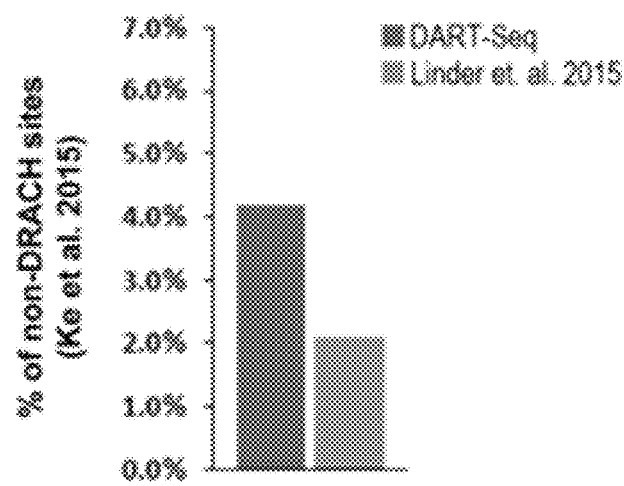
FIG. 6B shows DART-Seq C to U editing events (left column) which overlapped with CIMS/CITS sites at non-DRACH $m^6A$ residues ($m^6A$ sites not located within a DRACH consensus motif taken from the Ke et al. 2015 dataset) shown as a percentage of the total number of non-DRACH $m^6A$ sites. CIMS/CITS sites from Linder et al. 2015 were also compared to these non-DRACH sites, showing a similar degree of overlap as is observed with DART-Seq.
Figure 6C:
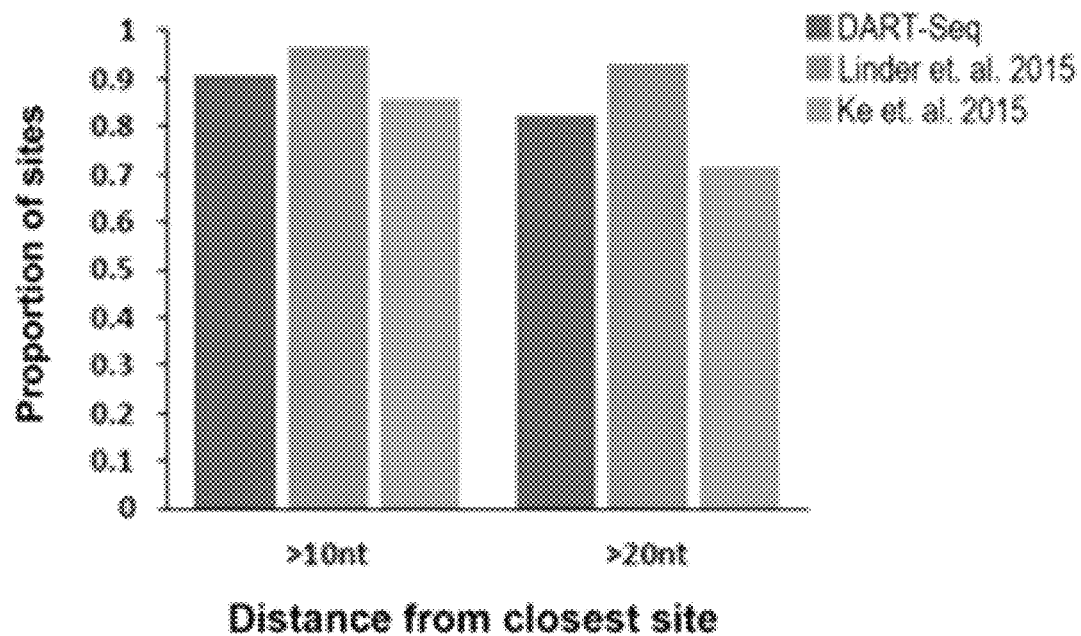
FIG. 6C shows minimal promiscuous C to U editing at non-$m^6A$-adjacent cytidines as revealed by analysis of DART-Seq site clustering. Individual DART-Seq or CIMS/CITS sites were analyzed from DART-Seq data or two miCLIP datasets (Ke et al. 2015 and Linder et al. 2015). For each site within the dataset, the closest C to U editing site (DART-Seq) or CIMS/CITS site (miCLIP) was identified. Shown is the proportion of total sites (DART-Seq in left hand column; miCLIP in middle and right columns) that are at least 10 nt or 20 nt away from the closest site. All three datasets show a similar distribution of sites, with the majority of sites being at least 10 nt apart.

Next, the ability of DART-Seq to identify individual $m^6A$ sites compared to antibody-based approaches was assessed. Comparison of global $m^6A$ profiling datasets obtained by $m^6A$ immunoprecipitation showed that DART-Seq performs similarly in its ability to detect $m^6A$ sites (FIGS. 6a and 6b). It also showed an enrichment of DART-Seq editing adjacent to $m^6A$ sites identified by single-nucleotide resolution $m^6A$ profiling (miCLIP/$m^6A$-Seq). Additionally, the majority (91.4%) of C to U editing sites in APOBEC1-YTH-expressing cells are preceded by an A, compared to only 67.9% of C to U editing sites in cells expressing APOBEC1 alone, suggesting that APOBEC1-YTH deamination is directed specifically toward cytidines adjacent to $m^6A$ and that promiscuous editing of non-adjacent cytidines is rare. Further support for this comes from the finding that over 90% of DART-Seq sites are greater than 10 nucleotides away from the closest editing event, which is similar to the distribution seen in miCLIP (FIG. 6c). Collectively, these data indicate that DART-Seq is capable of detecting $m^6A$ sites in cellular RNAs transcriptome-wide.

4. Validation of the DART-Sea Approach

Figure 7A:
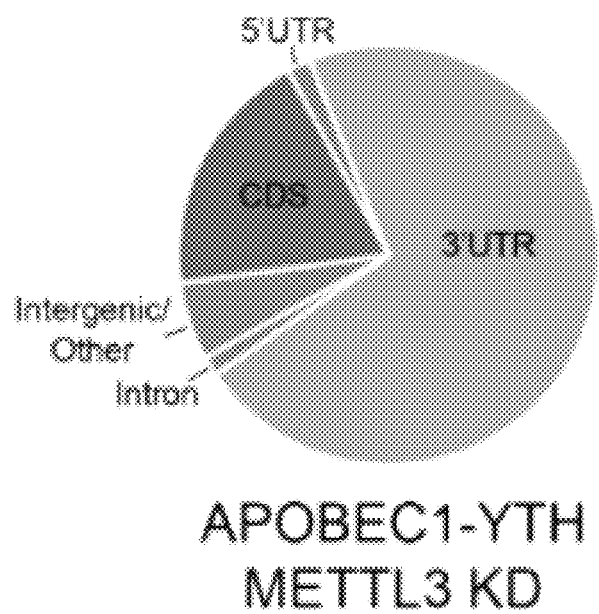
FIG. 7A shows a pie chart illustrating the distribution of C to U editing events identified by DART-Seq in METTL3 KD cells. n=2 independent samples.
Figure 7B:
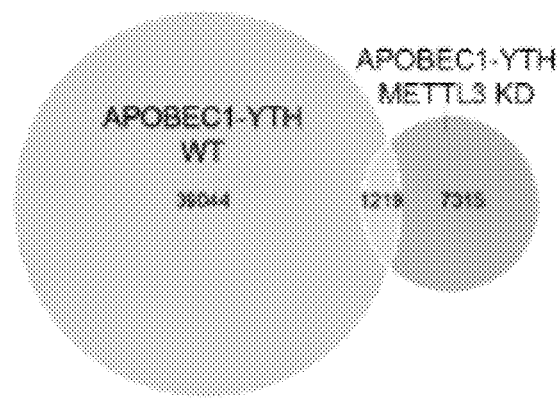
FIG. 7B shows a venn diagram illustrating the overlap between C to U editing sites called by DART-Seq in wild type (WT) and METTL3 KD HEK293T cells.

To validate individual DART-Seq sites, RT-PCR and Sanger sequencing was performed to determine whether C to U editing occurs adjacent to $m^6A$ sites previously quantified by miCLIP[5] or by SCARLET[16], another single-nucleotide resolution $m^6A$ identification method. The presence of editing adjacent to known m⁶A sites in the BSG and ACTB mRNAs in cells expressing APOBEC1-YTH was confirmed, but no robust editing in cells expressing APOBEC1 alone was observed. To further validate that DART-Seq editing depends on the presence of $m^6A$, DART-Seq using HEK293T cells depleted of the $m^6A$ methyltransferase, METTL3 was performed. METTL3-depleted cells exhibited fewer DART-Seq editing events in general and loss of the GGACU $m^6A$ consensus sequence surrounding DART-Seq sites. Furthermore, 97% of the DART-Seq sites detected in wild type cells were lost in METTL3-depleted cells (FIGS. 7a and 7b) These results further confirm that DART-Seq editing depends on $m^6A$.

5. DART-Seq Enables Low-Input Global m6A Profiling

One of the biggest challenges for global $m^6A$ detection has been the large amount of input RNA required for effective immunoprecipitation and sequencing. Recent advances in library preparation have provided important improvements, with some studies reporting $m^6A$ profiling using as little as 150 ng of mRNA or 500 ng of total RNA. However, even with such improvements, the requirement for high nanogram amounts of poly(A) or rRNA-depleted RNA can be limiting for certain cell or tissue types.

Figure 8:
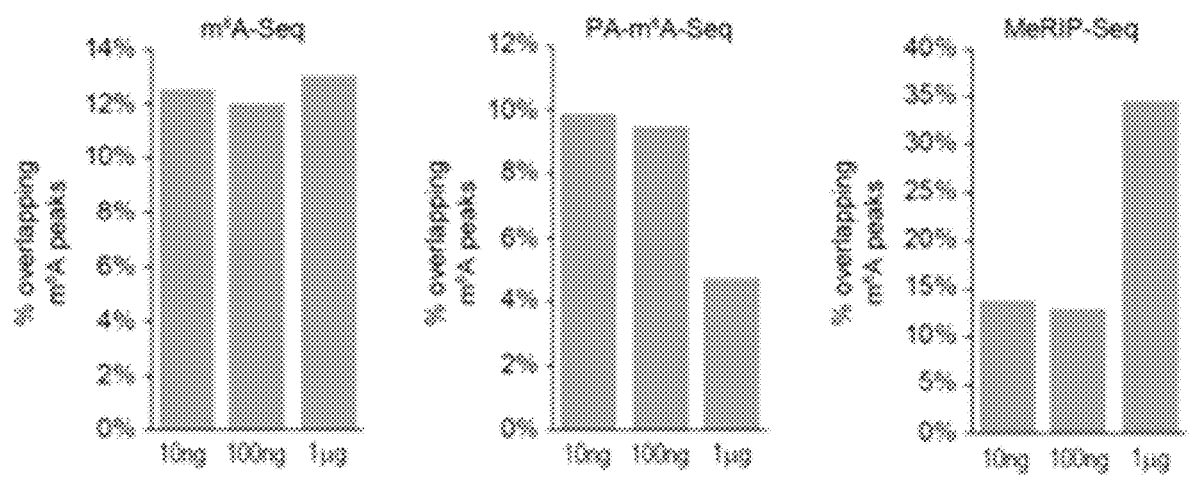
FIG. 8 shows that low-input DART-Seq performs comparably to high-input DART-Seq in its ability to identify $m^6A$ sites. DART-Seq datasets from samples prepared using 10 ng (n=1), 100 ng (n=1), and 1 μg (n=3) of total RNA as input were compared to $m^6A$ peak regions from three independent $m^6A$ immunoprecipitation datasets ($m^6A$-Seq4, PA-$m^6A$-Seq15, and MeRIP-Seq3). The proportion of $m^6A$ peaks from each dataset that overlaps with each of the three DART-Seq datasets is shown.

It was therefore tested whether DART-Seq could be used to detect $m^6A$ in low-input RNA samples. Using as little as 10 nanograms of total RNA as input, over 79% of the DART-Seq edited mRNAs that were identified in the high-input DART-Seq library were detected. Low-input DART-Seq samples perform similarly to antibody-based approaches for $m^6A$ detection, albeit with slightly reduced efficiency compared to high-input DART-Seq samples (FIG. 8). In addition, low-input DART-Seq sites are enriched for $m^6A$ consensus motifs and near the 5' end of the 3'UTR. Thus, DART-Seq is capable of detecting $m^6A$ sites from as little as 10 nanograms of total RNA.

6. m6A Detection Using in vitro DART-Seq

Figure 9A:
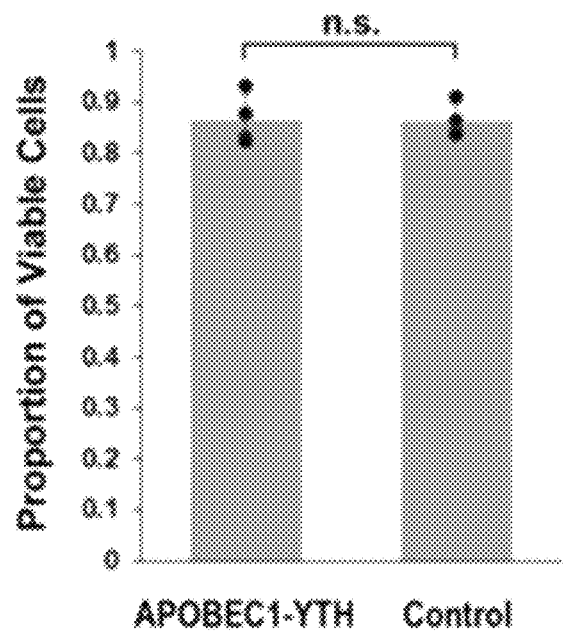
FIG. 9A shows APOBEC1-YTH expression does not affect cell viability. Trypan blue staining of HEK293T cells transfected with APOBEC1-YTH was used to assess cell viability. The proportion of viable cells is shown compared to untransfected HEK293T cells ("Control"). Shown are sample means+/−S.D. n=4 biological replicates; "n.s"=non-significant (P=0.943); 2-tailed t-test.
Figure 9B:
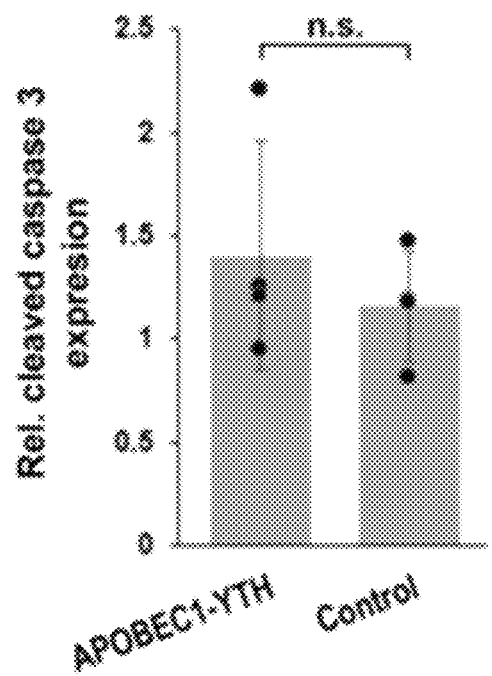
FIG. 9B shows APOBEC1-YTH expression does not affect levels of the apoptosis marker cleaved caspase 3. HEK293T cells were transfected with APOBEC1-YTH and protein was isolated 24 h later. Western blotting was done to assess levels of cleaved caspase 3. Shown are the average levels of cleaved caspase 3 relative to β-actin. Compared to untransfected HEK293T cells ("Control"), APOBEC1-YTH-expressing cells do not exhibit altered levels of cleaved caspase 3. Shown are sample means+/−S.D. n=4 biological replicates; "n.s"=non-significant (P=0.462); 2-tailed t-test.
Figure 9C:
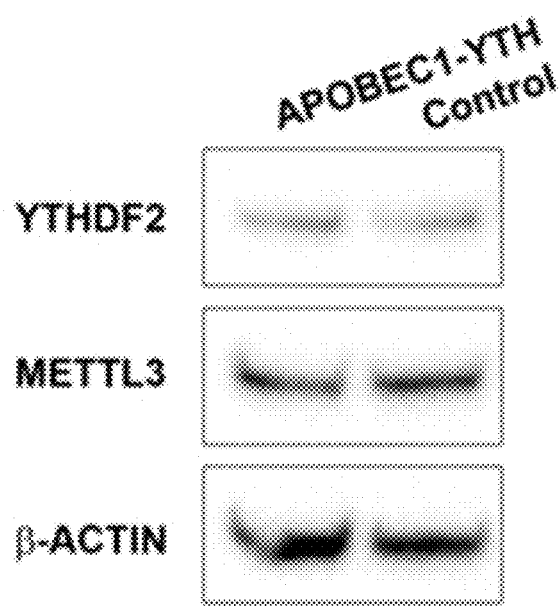
FIG. 9C shows levels of major $m^6A$ regulators are not altered by APOBEC1-YTH expression. Western blotting was used to assess levels of METTL3 and YTHDF2 in APOBEC1-YTH-transfected cells as well as untransfected cells ("Control"). Shown are representative images from n=2 biological replicates.
Figure 10:
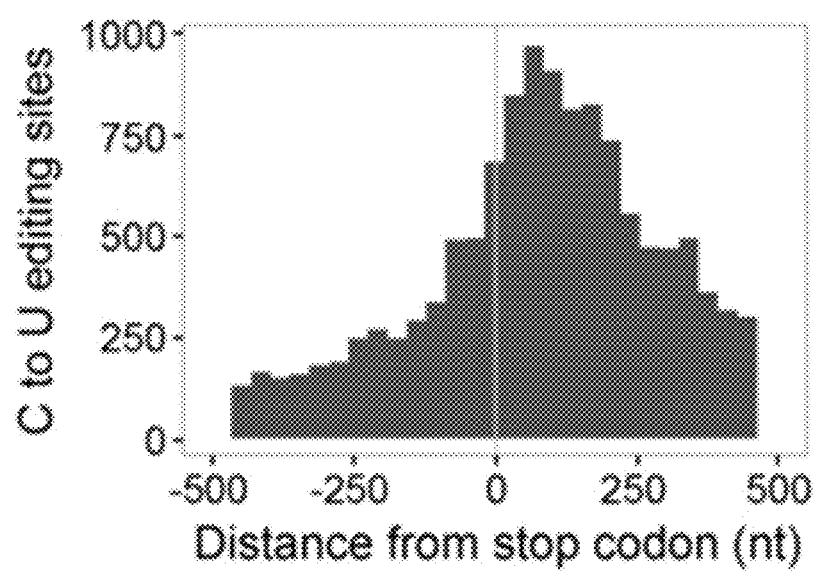
FIG. 10 shows a density plot for a metagene analysis of the absolute distance of C to U editing sites from the stop codon (position 0) for in vitro DART-Seq assays. C to U editing is enriched in the vicinity of the stop codon, which mirrors the distribution of $m^6A$. n=2 independent samples.

APOBEC1-YTH-expressing cells exhibit normal levels of genes in the $m^6A$ regulatory pathway and show no alterations in cell viability, suggesting that prolonged APOBEC1-YTH expression does not alter the $m^6A$ landscape (FIG. 9a-c). Nevertheless, APOBEC1-YTH overexpression may not be possible or desirable in some cases, which would necessitate the use of in vitro deamination to perform DART-Seq. To test the ability of this approach to detect $m^6A$ in cellular RNA, in vitro DART-Seq using HEK293T cell RNA was performed. C to U editing at known $m^6A$ sites was detected, and global analyses revealed a distribution and motif enrichment similar to that of $m^6A$ (FIG. 10). Although the majority (91%) of methylated mRNAs identified with in vitro DART-Seq were also identified using cellular DART-Seq, in vitro DART-Seq identified fewer methylated mRNAs than cellular DART-Seq, suggesting reduced efficiency. Thus, in vitro DART-Seq can reliably mark $m^6A$ sites in cellular RNAs, although this approach will likely benefit from further optimization to increase identification of low-abundance $m^6A$ sites.

7. DART-Seq Distinguishes m6A From m6Am

A limitation of antibody-based $m^6A$ detection strategies is cross-reactivity of $m^6A$ antibodies with $m^6Am$. Hydrogen bonding between the YTH domain and the 2'-OH of $m^6A$ suggests that the YTH domain used in DART-Seq may not recognize $m^6Am$. Furthermore, unlike $m^6A$ residues, $m^6Am$ is not invariably following by a cytidine, which means that detection of $m^6Am$ by APOBEC1-YTH would require deamination of cytidines further away from the modified base. It was, therefore, tested whether DART-Seq could be used to distinguish $m^6A$ from $m^6Am$.

To investigate this, a list of $m^6Am$ sites in HEK293 cells was compared to DART-Seq datasets. Since $m^6A$ sites in 5'UTRs may actually reflect $m^6Am$ residues at misannotated start sites, the DART-Seq sites were extended to include regions 4 nt up- and downstream from the C to U editing site (Linder, B. et al. Single-nucleotide-resolution mapping of m6A and m6Am throughout the transcriptome. *Nat Methods* 12(8): 767-72 (2015)). Only one RNA with overlap between extended DART-Seq sites and $m^6Am$ sites was found. Upon closer examination, the DART-Seq editing site in this transcript is diminished in METTL3-depleted cells and is found internally within the 5'UTR, suggesting that it is not an $m^6Am$ site. This suggests that DART-Seq does not recognize $m^6Am$ and can be used to identify $m^6A$ residues independently of $m^6Am$ residues.

8. Estimation of m6A Abundance.

Determining $m^6A$ abundance within individual RNAs has been a major challenge to RNA methylation research. SCARLET enables quantitative measures of $m^6A$ in individual RNAs, but this approach is not amenable to transcriptome-wide measurements. $m^6A$-LAIC-Seq uses immunoprecipitation of full-length transcripts to estimate methylation levels of individual mRNAs, but it does not account for multiple $m^6A$ sites or the presence of $m^6Am$. Finally, peak over input (POI) can be used in MeRIP-Seq, but these measures provide only a rough estimate of $m^6A$ abundance.

Figure 11:
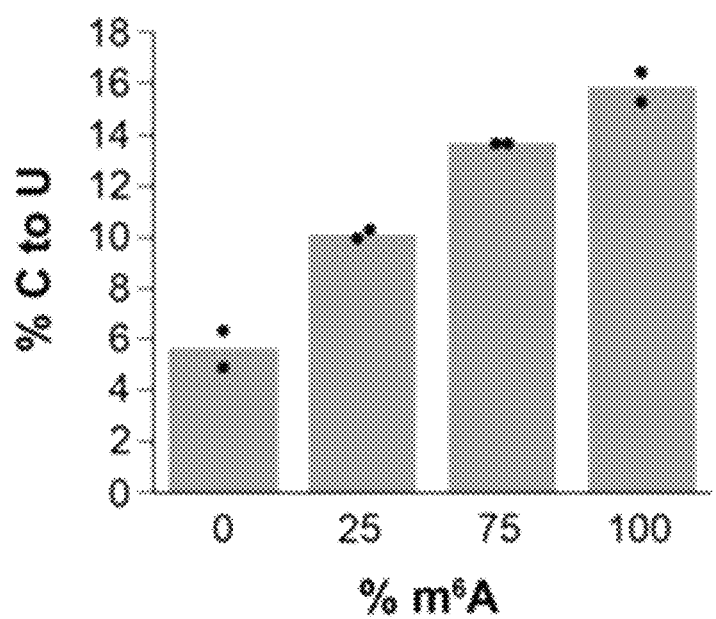
FIG. 11 shows quantification of the proportion of U/C editing at the cytidine adjacent to the $m^6A$ site reveals a direct relationship between the amount of C to U editing and the abundance of $m^6A$ within the RNA.

It was speculated that the degree of methylation may correlate with APOBEC1-YTH binding and C to U editing to enable global estimates of $m^6A$ abundance in individual transcripts. To test this, in vitro deamination assays were performed using RNA with various amounts of $m^6A$. C to U editing was positively correlated with $m^6A$ levels at individual sites within an RNA (FIG. 11). Examination of DART-Seq editing of cellular RNAs also showed a positive relationship between $m^6A$ abundance and editing efficiency. Thus, DART-Seq can be used as an indicator of $m^6A$ abundance in individual RNAs.

9. DART-Seq Identifies m6A Accumulation in Cellular RNAs

Figure 12A:
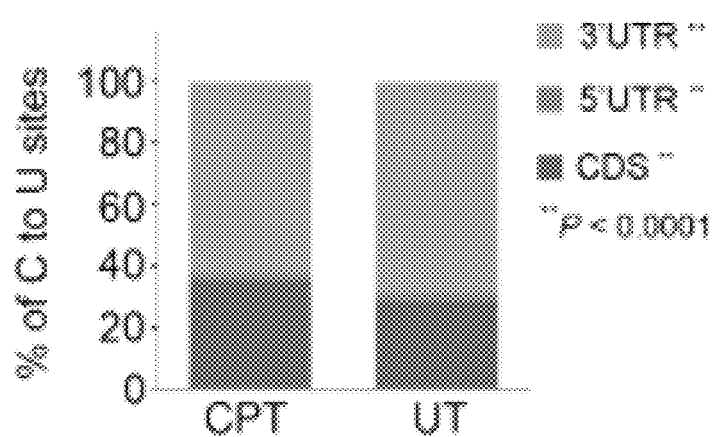
FIG. 12A shows the distribution of C to U mutations discovered by DART-Seq in HEK293T cells treated with camptothecin (CPT; n=5,689) compared to untreated controls (UT; n=40,594), indicating a slight enrichment within the CDS (bottom box of each column).
Figure 12B:
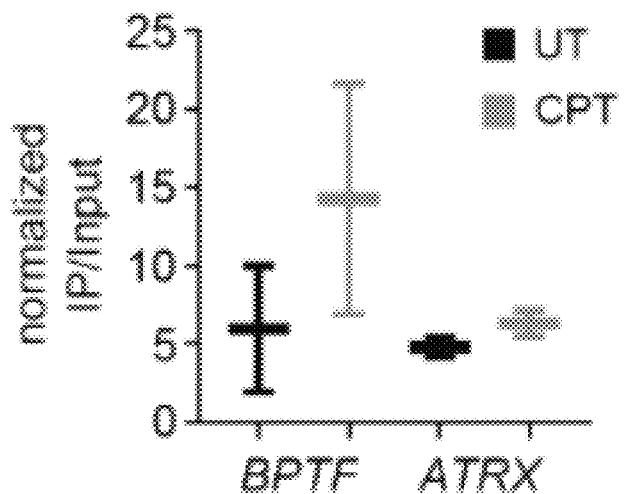
FIG. 12B shows enrichment of $m^6A$ in the BPTF and ATRX mRNAs following CPT treatment confirmed by MeRIP-RT-qPCR. n=2 biological replicates; box plot indicates mean and upper/lower limits.
Figure 12C:
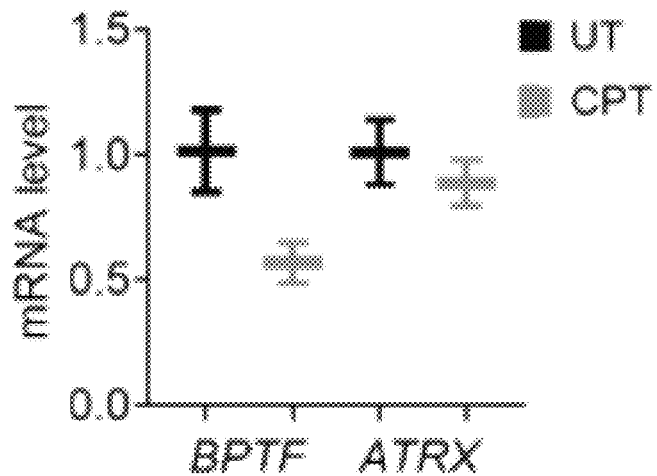
FIG. 12C shows a decrease in abundance of the BPTF and ATRX transcripts following CPT treatment as indicated by RT-qPCR analysis using RNA from untreated and CPT-treated cells. n=2 biological replicates; box plot indicates mean and upper/lower limits.

Next, it was tested whether changes in $m^6A$ can be detected by DART-Seq. Previous studies have shown that treatment of cells with moderate concentrations of the topoisomerase inhibitor camptothecin (CPT) causes slowed transcription and an increase in $m^6A$ abundance in the CDS. HEK293T cells expressing APOBEC1-YTH were treated with CPT for 5 h and DART-Seq was performed to identify $m^6A$ sites. This led to 6,258 C to U sites that showed at least a 2-fold increase in editing compared to untreated cells. Metagene analysis of these sites indicated a slight enrichment in the CDS compared to untreated cells (FIG. 12a), and examination of individual mRNAs confirmed this analysis. The increase in $m^6A$ within the CDS of select mRNAs was validated using $m^6A$ immunoprecipitation followed by RT-qPCR (MeRIP-RTqPCR) (FIG. 12b). Increased $m^6A$ in these RNAs also negatively correlated with their abundance (FIG. 12c), similar to what has been previously observed. Thus, DART-Seq can be used to detect accumulation of $m^6A$ in individual RNAs in response to changing cellular conditions.

10. Long-Read DART-Seq Reveals Isoform-Specific Methylation Patterns

Immunoprecipitation-based $m^6A$ detection strategies have previously reported clustering of $m^6A$ sites. However, it remains unknown whether this reflects clustering of $m^6A$ on the same or distinct RNA molecules. Since DART-Seq induces editing events in single transcripts, it was reasoned that individual sequencing reads could be examined to determine whether $m^6A$ sites are found in the same RNA molecule. To investigate this, long-read DART-Seq was performed using the PacBio platform. Examination of individual mRNAs showed that, although some transcripts exhibit isoform-specific regional editing, others contain DART-Seq sites in the 5'UTR, CDS, and 3'UTR. In addition, 41% of reads spanning at least two editing sites contain two or more C to U editing events. These data suggest that the majority of individual RNA molecules have just one $m^6A$ site, but that many RNAs harbor multiple sites, which is consistent with previous reports from isoform-specific $m^6A$ immunoprecipitation ($m^6A$-LAIC-seq). Further studies will be needed to understand whether distinct $m^6A$ residues on the same transcript work in a coordinated or competing manner. Additionally, although our data suggest that multiple C to U editing events caused by the same $m^6A$ site are rare (FIG. 6c), studies of clustered $m^6A$ sites in individual transcripts may benefit from additional validation using miCLIP or SCARLET.

Example 2. Detecting $m^6A$ in Single Cells and Brain Tissue

A. Materials and Methods

Vector Construction. The pET-His6-MBP-TEV-LIC plasmid (Addgene 29656) was linearized by digestion with SspI and gel purified. The APOBEC1-YTH and APOBEC1-YTHmut sequences were PCR amplified with the addition of a 5' sequence (TACTTCCAATCCAATGCA)(SEQ ID NO: 54) and a 3' sequence (TTATCCACTTCCAATGTTATTA) (SEQ ID NO: 55). 300 ng of the linearized vector was then treated with 0.6 μL of T4 Polymerase (NEB) in a buffer containing 1×NEB Buffer 2.1 and 2.5 mM dGTP. The solution was incubated at 22° C. for 20 minutes, and 75° C. for 15 minutes. 0.2 pmol of the insert was then treated with 0.4 μL of T4 Polymerase (NEB) in a buffer containing 1×NEB Buffer 2.1 and 2.5 mM dCTP. The solution was incubated at 22° C. for 20 minutes, and 75° C. for 15 minutes. The insert was then annealed to the linearized vector by incubating 3 μL of the vector reaction with 2 μL of the insert reaction for 5 minutes at room temperature. Then 1 μL of 25 mM EDTA was added and 3 μL was used to transform DH5α cells. Successful cloning was validated by restriction digestion and Sanger sequencing of the insert sequence. The plasmids were then purified from DH5a cells and transformed into Rosetta 2 (DE3) pLYS cells. The resulting plasmids express a 6×His-MBP-APOBEC1-YTH-HA fusion protein under control of the lac operator promoter so that it is inducible with lactose or IPTG.

Bacterial Induction and lysis. Rosetta 2 pLYS cells containing plasmids coding for 6×His-MBP-APOBEC1-YTH-HA or 6×His-MBP-APOBEC1-YTHmut-HA were cultured overnight in 10 mL of LB broth. The next morning, 5 mL of overnight culture was added to 1 L of ZY induction medium (1% tryptone, 0.5% yeast extract, 25 mM $Na_2HPO_4$, 25 mM $KH_2PO_4$, 50 mM $NH_4Cl$, 5 mM $Na_2SO_4$, 0.5% glycerol, 0.05% glucose, 0.2% α-lactose, 2 mM $MgSO_4$) containing 100 μg/mL kanamycin and cultured for approximately 10 hours at 37° C. with shaking in baffled flasks. Cultures were then grown at 20° C. with shaking for 16 hours. Expression was induced as the culture consumes the glucose and begins to import the lactose. After 16 hours, the cells were pelleted by centrifugation at 5,000 g for 15 minutes at 4° C. The pellets were then flash frozen in liquid nitrogen and thawed at 4° C. Once thawed the cells were lysed using the Qproteome Bacterial Protein Prep Kit (Qiagen). Briefly, the pellet from 1 L of culture was resuspended in 40 mL of lysis buffer (40 mL Native Lysis Buffer, 40 mg lysozyme, 1 U benzonase) by pipetting while on ice. After resuspension, the lysate was incubated on ice for 30 minutes, with gentle swirling every 10 minutes. Then the lysate was cleared of insoluble material by centrifugation at 10,000 g for 60 minutes at 4° C. and the supernatant was moved to a fresh tube and stored on ice.

Figure 13:
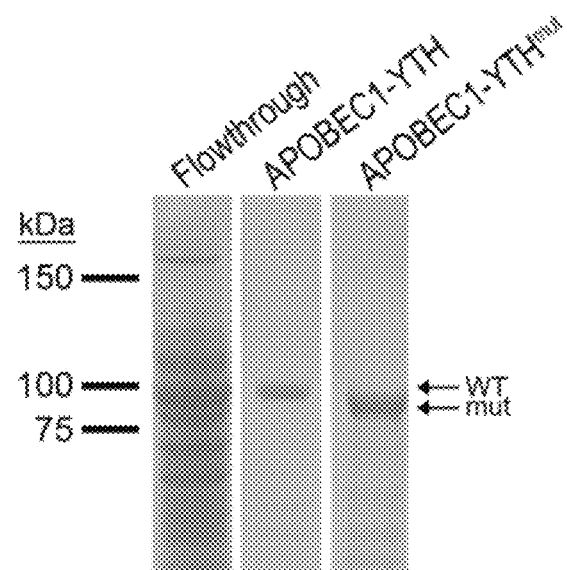
FIG. 13 shows protein levels of APOBEC1-YTH and APOBEC1-YTHmut. Coomassie staining shows the results of small-scale purification of the APOBEC1-YTH and APOBEC1-YTH$^{mut}$ proteins using bacterial expression and a 6×His/nickel-based purification system.

Protein purification. 750 μL of resuspended Ni-NTA resin (Gold Bio) was pipetted into a 10 mL polypropylene chromatography column (Bio-Rad) and the liquid drained by gravity flow. Once drained, 6 mL of equilibration buffer (50 mM $Na_2HPO_4$, 100 mM NaCl, 10 mM Imidazole) was added and allowed to drain over the resin by gravity flow. Once drained, the lysate was added to the column and allow to pass over the resin by gravity flow. After the lysate completely passed through the resin, 10 mL of wash buffer 1 (PBS with 10 mM imidazole, 5 mM (3-mercaptoethanol (BME)) was added and allow to drain by gravity flow. The resin was then rinsed with two 6 mL washes of wash buffer 2 (PBS with 25 mM imidazole, 5 mM BME), two 6 mL washes of wash buffer 3 (PBS with 50 mL imidazole, 5 mM BME), and two 6 mL washes of wash buffer 4 (PBS with 60 mM imidazole, 5 mM BME). The protein was then eluted from the resin with 1 mL of elution buffer 1 (10 mM Tris-HCl (pH 7.4), 100 mM NaCl, 250 mM imidazole, 5 mM BME), followed by 1 mL of elution buffer 2 (10 mM Tris-HCl (pH 7.4), 100 mM NaCl, 300 mM imidazole, 5 mM BME), and 1 mL of elution buffer 3 (10 mM Tris-HCl (pH 7.4), 100 mM NaCl, 500 mM imidazole, 5 mM BME). Elution 1 and 2 were determined to contain a vast majority of the protein, so elution 1 and 2 were pooled and dialyzed in a 0.5-3 mL Slide-a-Lyzer dialysis cassette with a 3.5 KD MWCO (Thermo-Fisher). The 2 mL eluate was added to the cassette, which was placed in 1 L of storage buffer (10 mM Tris-HCl (pH 7.4), 100 mM NaCl, 1 mM DTT) at 4° C. for 2 hours. After 2 hours, the cassette was placed in 1 L of fresh storage buffer and dialyzed for 16 hours. After dialysis, the sample was removed from the cassette and diluted by adding an equal volume of glycerol. Aliquots were stored at −20° C. Protein levels of APOBEC1-YTH and APOBEC1-YTH$^{mut}$ are shown using Coomassie staining (FIG. 13).

In vitro DART with purified protein In vitro DART-seq was performed on total RNA isolated from cultured HEK293T cells, primary mouse hippocampal neurons, whole brain lysates, and synaptoneurosome preparations taken from the mouse striatum. DART assays were carried out by combining 250 ng purified APOBEC1-YTH or APOBEC1-YTHmut protein with 30-50 ng total RNA in a 50 ul reaction with 5 ul 10×DART Buffer (500 mM KCl, 100 mM Tris-HCl, pH 7.4, 1 uM $ZnCl_2$) and 1 ul RNaseOUT. Samples were gently mixed with a pipette and incubated at 37° C. for 4 h. RNA was then isolated with the RNeasy Micro Kit (Qiagen). For Sanger sequencing, cDNA was generated using SuperScript III (Thermo Fisher) or iScript (Bio-Rad) according to manufacturer's instructions. For next-generation sequencing, libraries were prepared as indicated.

Transient transfection and cell sorting. To obtain single-cell preparations of APOBEC1-YTH or APOBEC1-YTHmut expressing cells, HEK293T cells were transiently transfected with pCMV-APOBEC1-YTH-IRES-EGFP or pCMV-APOBEC1-YTHmut-IRES-EGFP using Lipofectamine 2000 according to the manufacturer's instructions (Thermo Fisher). After 24 hours, cells were removed from the plate with TrypLE (Thermo Fisher) and resuspended in DMEM/1% FBS at a dilution of 200,000 cells/mL. Cells were then treated with 10 U DNaseI (NEB) for 15 min at 25°

C. and washed with 2 mL DMEM/1% FBS with 1 U Dnasel. 5 uL of lysis buffer (NEBNext Single cell/Low Input Library Prep kit) was added to each well of a 96-well plate. Cells were then sorted using a A02 FACSAriaII, with 1 cell being sorted in each of 8 wells of a 96 well PCR plate. This was done for APOBEC1-YTH and APOBEC1-YTHmut expressing cells. Immediately after sorting, plates were flash frozen on dry ice and stored at −80° C. until further processing. Sequencing library preparation was performed using the NEBNext Single Cell/Low Input Library Prep Kit according to the manufacturer's instructions (NEB).

Single-cell DART-seq (scDART-seq). Sequencing library preparation using the NEB Single-cell/Low Input Library Prep Kit for Illumina (library preparation) and NEBNext Index Primer Sets (Set 1 and Set 4 were used) was performed according to manufacturer's protocol. The pipetting steps for reverse transcription and cDNA amplification were performed in a biosafety cabinet. Briefly, 1 μL of RT primer mix and 3 μL of nuclease-free water was added to each well with lysis buffer and incubated at 70° C. for 5 minutes. Then, 11 μL of reverse transcription mix (5 μL RT buffer, 1 μL template switching oligo, 2 μL RT enzyme mix, and 3 μL nuclease-free water) was added to each well and incubated at 42° C. for 90 minutes, then 70° C. for 10 minutes. cDNA was amplified by adding 50 μL cDNA PCR master mix, 2 μL cDNA PCR Primer, and 28 μL of nuclease-free water to each well and incubated in a thermocycler with following conditions (98° C. for 45 seconds, then 18 cycles of: 98° C. for 10 seconds, 62° C. for 15 seconds, 72° C. for 3 minutes, then 72° C. for 5 minutes). The cDNA was cleaned using SPRI Select beads (0.6× of sample volume) and a magnetic tube holder. The beads were washed twice with 80% ethanol. The cDNA was then eluted with 504, 0.1×TE before being re-bound to the beads using the provided Bead Reconstitution Buffer and washed twice again with 80% ethanol. The cDNA was eluted into 30 μL of 0.1×TE buffer. cDNA quality and quantity was determined using a High Sensitivity DNA Bioanalyzer Assay. Successful cDNA preps were fragmented by adding 26 μL of purified cDNA, 7 μL FS Reaction Buffer, and 2 μL FS Enzyme Mix and incubating in a thermocycler at 37° C. for 25 minutes and 65° C. for 30 minutes. Adaptor ligation was performed by adding 30 μL Ligation Master Mix, 1 μL Ligation Enhancer, and 2.5 μL of NEBNext Adaptor for Illumina (1:25 diluted) and incubating at 20° C. for 15 minutes. Then 3 μL of USER Enzyme was added and incubated at 37° C. for 15 minutes. The DNA was cleaned using SPRI Select beads (0.8×sample volume) and washed 2× with 80% ethanol and eluted with 15 μL of 0.1×TE. Libraries were amplified and indexes for multiplexing added by adding 15 μL DNA fragments, 25 μL Q5 Master Mix, 5 μL Universal Primer, and 5 μL i7 Primer and incubating in a thermocycler with the following conditions (98° C. for 30 seconds, then 8 cycles of: 98° C. for 10 seconds, 65° C. for 75 seconds, then 65° C. for 5 minutes. The indexed libraries were cleaned using SPRI Select beads (0.9× sample volume) and washed 2× with 80% ethanol and eluted with 15 μL of 0.1×TE. Library quality and quantity was determined using a High Sensitivity DNA Bioanalyzer Assay. Libraries were pooled and sequenced at a concentration of 10 nM on a Novaseq6000. Quality filtering, alignment, and C to U analysis was performed as described (Meyer, *Nature Methods* 2019). Metagene analysis and consensus sequence analysis was performed as described (Meyer, *Nature Methods* 2019) and revealed an enrichment of C to U editing in the vicinity of the stop codon and near GAC or AAC sequences as has been observed for $m^6A$.

Stable cell lines. Stable HEK293T cell lines were generated by lentiviral infection and antibiotic resistance selection. APOBEC1-YTH and APOBEC1-YTHmut were cloned into the TLCV2 lentiviral vector (Addgene 87360) replacing the Cas9 sequence using Gibson Assembly. The resulting lentiviral vectors contained the TRE-Tight promoter (containing a Tet-response element just upstream from a minimal CMV promoter) driving expression of APOBEC1-YTH-T2A-EGFP or APOBEC1-YTHmut-T2A-EGFP.

Lentiviral production. 4 μg of lentiviral vector DNA was combined with 2 μg psPAX packaging vector and 1 μg pMD2.G coat protein plasmid in 1 mL of OPTI-MEM. 21 μL of PEI was added and the mixture was incubated at room temperature for 25 minutes. It was then added dropwise to a 10 cm plate of HEK293T cells at 80% confluency cultured in full DMEM with 10% FBS. After 24 hours the medium was replaced with 10 mL of fresh DMEM with 10% FBS. 72 hours post transfection, the media was collected and centrifuged at 600 g for 10 minutes before the supernatant was passed through a 0.45 μm cellulose filter to remove large debris. Approximately 9 mL of medium was added to ultracentrifuge tubes (Beckman Coulter Fef: 331374). Then 1.5 mL of chilled, sterile 20% glucose was carefully added below the medium to create two separate phases. Purified virus was pelleted by centrifugation at 19,7000 rpm for 2 hours at 4° C. in a Beckman SW40 swinging bucket rotor. After centrifugation, the supernatant was removed and the tube was allowed to air dry for 10 minutes. When dry, 100 μL of PBS was added and the virus was resuspended at 4° C. overnight, with rocking. The next day, 10 μL aliquots were made and stored at −80° C. until use.

Viral titering. 3,000 HEK293T cells were plated in each well of a 96-well plate and cultured for 24 hours in DMEM with 10% FBS. Then purified virus was added at increasing concentrations (1:5, 1:25, 1:125, 1:625, 1:3125). 24 hours after adding the virus, the medium was replaced with fresh DMEM with 10% FBS containing 1 μg/mL doxycycline to induce expression. 6 hours after doxycycline treatment, GFP signal intensity was observed by fluorescence microscopy using a Leica DMi8 inverted microscope.

Infection and selection of stable cells. HEK293T cells were plated onto 6 well plates and cultured in DMEM with 10% FBS. Viral stock (1:500 for APOBEC1-YTHmut, 1:100 for APOBEC1-YTH) was then added. After 24 hours, medium was changed, and another 24 hours after that, medium was replaced with selective medium (DMEM/10% FBS with 5 ug/mL puromycin). Fresh medium was added every 48 hours. After 7 days of puromycin selection, cells were diluted and plated with an average density of 1 cell per well across several 96 well plates. Individual wells were screened to identify wells with just a single cell. Colonies were then expanded from these clonal isolates. Expression of APOBEC1-YTH or APOBEC1-YTHmut was induced by treating cells with 1 μg/mL doxycycline and confirmed by EGFP expression and anti-HA western blot. C to U deamination at known $m^6A$ sites in the ACTB and EEF2 mRNAs was tested with RT-PCR and Sanger sequencing and could be detected as early as 4 hours after dox addition. Complete editing was observed after 16-24 hours of dox treatment.

B. Results

1. Alternative deaminase enzymes improve in6A detection.

Figure 14:
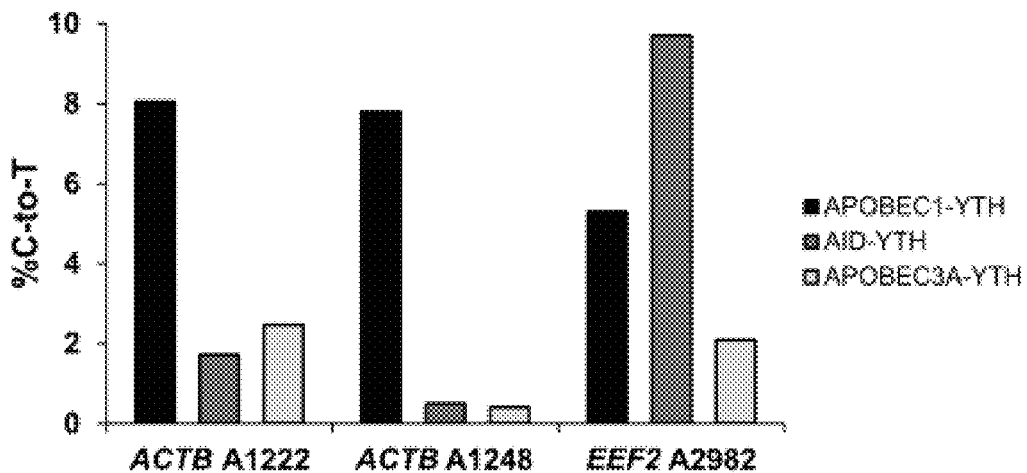
FIG. 14 shows the percentage (shown as % C to T conversion in cDNA sequences) for each fusion protein variants. The AID-YTH variant causes higher editing rates in the EEF2 mRNA compared to APOBEC1 and APOBEC3A.

To test the effect of deaminase variants on m6A detection the cytidine deaminases APOBEC1, AID, and APOBEC3A were all fused to the YTH domain of YTHDF2 and expressed in HEK293T cells for 24 h. Total RNA was isolated and subjected to RT-PCR and Sanger sequencing targeting methylated regions of the ACTB and EEF2 mRNAs. FIG. 14 shows the % C to T conversion (in cDNA sequences) for each fusion protein. The AID-YTH variant causes higher editing rates in the EEF2 mRNA compared to APOBEC1 and APOBEC3A.

Figure 15:
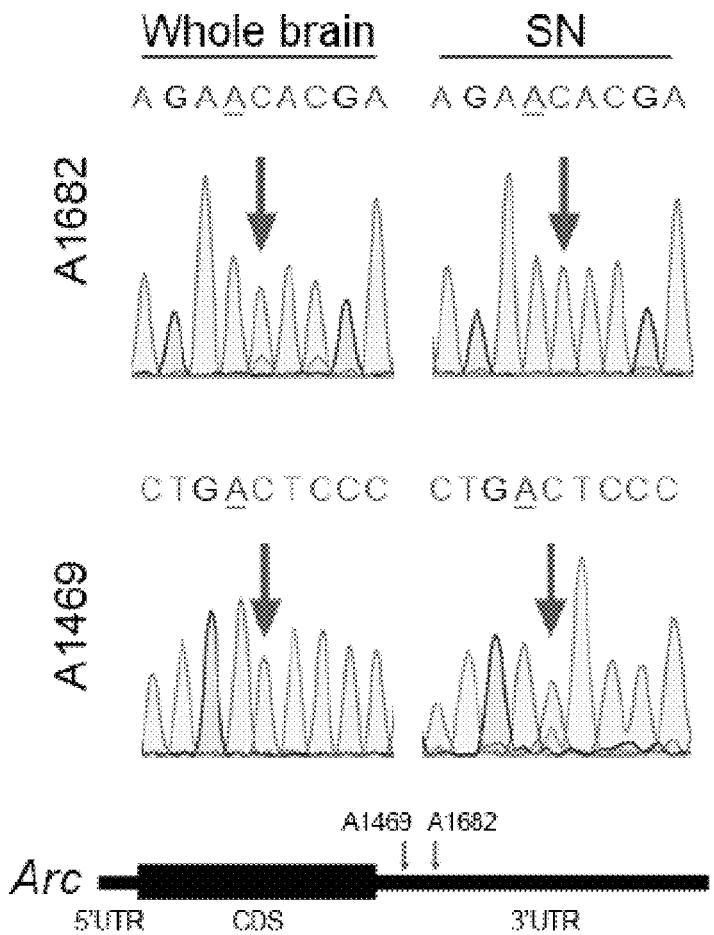
FIG. 15 shows the detection of alternative methylation of synaptic mRNAs from mouse brain tissue. Shown are Sanger sequencing traces at two $m^6A$ sites in the 3'UTR of Arc, an mRNA enriched near synapses. Arrows indicate the cytidine adjacent to the $m^6A$ site. DART-seq induced C to U mutations (C to T in cDNA) show that site A1682 is selectively methylated in whole brain samples, whereas site A1469 is selectively methylated in the SN fractions, suggesting that DART-seq can detect localization-specific methylation.

2. DART-seq Detects Alternative Methylation of Synaptic mRNAs From Mouse Brain Tissue In vitro DART-Seq Was Performed on RNA Isolated From Whole Brain or Synaptic fractions (SN). FIG. 15 shows Sanger sequencing traces at two $m^6A$ sites in the 3'UTR of Arc, an mRNA enriched near synapses. Arrows indicate the cytidine adjacent to the $m^6A$ site. DART-seq induced C to U mutations (C to T in cDNA) show that site A1682 is selectively methylated in whole brain samples, whereas site A1469 is selectively methylated in the SN fractions, suggesting that DART-seq can detect localization-specific methylation.

3. In vitro DART-seq Detects m6A Sites That are Identified by Cellular DART-Seq

In vitro DART-seq was performed using HEK293T cell total RNA and compared to DART-seq data obtained from HEK293T cells expressing APOBEC1-YTH for 24 h. RT-PCR and Sanger sequencing were performed to show C to U mutations (shown as C to T in the cDNA sequence) adjacent to two $m^6A$ sites in the ACTB mRNA and one $m^6A$ site in the EEF2 mRNA. Table 1 shows the mutations rates (% T) for cells expressing APOBEC1-YTH (labeled as Transfected) and for total cellular RNA subjected to in vitro DART-seq (labeled as In vitro). The results indicate that In vitro DART-seq mutation rates are comparable to cellular DART-seq mutation rates.

TABLE 1

Transfected and in vitro DART-seq mutation rates

|  | ACTBA1222 | ACTBA1248 | EEF2A2982 |
|---|---|---|---|
| Transfected (% T) | 16.4 | 39.8 | 13.2 |
| In vitro (% T) | 16.1 | 35.3 | 12.3 |

4. Single Cell DART-seq (scDART-seq) Detects m6A in Single Cells

HEK293T cells were transfected with APOBEC1-YTH or APOBEC1-YTHmut plasmids co-expressing EGFP. FACS sorting was used to isolate single cells, and RNA-seq libraries were generated and libraries sequenced with Illumina short read sequencing. Table 2 (see below) shows editing (as % C to T reads) at cytidine residues adjacent to $m^6A$ sites in the ACTB and SPEN mRNAs. Both mRNAs show high C-to-T mutation rates in cDNA adjacent to the methylated A. The total number of reads at each site is also shown (Total #reads). The APOBEC1-YTH expressing cells have higher levels of deamination compared to the APOBEC1-YTHmut expressing cells.

TABLE 2

Editing at $m^6A$ adjacent sites in the ACTB and SPEN mRNAs

|  | ACTB mRNA | | SPEN mRNA | |
|---|---|---|---|---|
|  | % C to T reads | Total # reads | % C to T reads | Total # reads |
| APOBEC1-YTH Cell 1 | 29% | 207 | 0% | 47 |
| APOBEC1-YTH Cell 2 | 0% | 177 | 27% | 98 |
| APOBEC1-YTH Cell 3 | 19% | 367 | 73% | 96 |
| APOBEC1-YTH Cell 4 | 68% | 380 | 0% | 1 |
| APOBEC1-YTHmut Cell 1 | 0% | 288 | 0% | 30 |
| APOBEC1-YTHmut Cell 2 | 0% | 196 | 0% | 98 |
| APOBEC1-YTHmut Cell 3 | 0% | 110 | 0% | 0 |
| APOBEC1-YTHmut Cell 4 | 0% | 244 | 0% | 5 |

Example 3. Transgenic Mice

To generate transgenic mice expressing APOBEC1-YTH and APOBEC1-YTHmut, the APOBEC1-YTH or APOBEC1-YTHmut sequences were first cloned into the pAi9 Rosa26 targeting vector at B stBI and MluI sites. This vector contains a lox-stop-lox cassette preceding the APOBEC1-YTH coding sequence. DNA was purified and used for embryonic stem (ES) cell injections. Following PCR confirmation of transgene-containing ES cell clones, positive clones were injected into morulae to generate chimeric mice. Positive chimeric mice were identified via genotyping and coat color and were mated to wild type mice to confirm germline transmission. Mice found to have germline transgene transmission will then be mated with phiC31 deleter mice (JAX labs) to remove the neomycin resistance cassette, which is flanked by attB/attP sites. The resulting neo-deleted lines will then be expanded and backcrossed for 3-5 generations. These mice will have ubiquitous expression of lox-stop-lox APOBEC1-YTH or YTHmut transgenes. After breeding with Cre driver lines of choice or following viral-mediated delivery of Cre recombinase, the APOBEC1-YTH or APOBEC1-YTHmut fusion protein will be expressed in a tissue of interest.

Sequences (amino acid sequence of YTHDF2-YTH)

SEQ ID NO: 1

PHPVLEKLRSINNYNPKDFDWNLKHGRVFIIKSYSEDDIHRSIKYNIWCSTEHGNKRLDA

AYRSMNGKGPVYLLFSVNGSGHFCGVAEMKSAVDYNTCAGVWSQDKWKGRFDVRWI

FVKDVPNSQLRHIRLENNENKPVTNSRDTQEVPLEKAKQVLKIIASYKHTTSIFDDFSHY

EKRQEEEESVKKERQGRGK (amino acid sequence of YTHDF2-YTH_W432A_W486A)

SEQ ID NO: 2

PHPVLEKLRSINNYNPKDFDWNLKHGRVFIIKSYSEDDIHRSIKYNIACSTEHGNKRLDA

-continued

```
AYRSMNGKGPVYLLFSVNGSGHFCGVAEMKSAVDYNTCAGVASQDKWKGRFDVRWI

FVKDVPNSQLRHIRLENNENKPVTNSRDTQEVPLEKAKQVLKIIASYKHTTSIFDDFSHY

EKRQEEEESVKKERQGRGK (amino acid sequence of YTHDF2-YTHmut)
                                                     SEQ ID NO: 3
GRVFIIKSYSEDDIHRSIKYNIWCSTEHGNKRLDAAYRSMNGKGPVYLLFSVNGSGHFCG

VAEMKSAVDYNTCAGVWSQDKWKGRFDVRWIFVKDVPNSQLRHIRLENNENKPVTNS

RDTQEVPLEKAKQVLKIIASYKHTTSIFDDFSHYEKRQEEEESVKKERQGRGK (amino acid sequence of YTHDF2-YTHmut2)
                                                     SEQ ID NO: 4
GRVFIIKSYSEDDIHRSIKYNIACSTEHGNKRLDAAYRSMNGKGPVYLLFSVNGSGHFCG

VAEMKSAVDYNTCAGVASQDKWKGRFDVRWIFVKDVPNSQLRHIRLENNENKPVTNS

RDTQEVPLEKAKQVLKIIASYKHTTSIFDDFSHYEKRQEEEESVKKERQGRGK (amino acid sequence of YTHDF2-YTH D422N)
                                                     SEQ ID NO: 5
PHPVLEKLRSINNYNPKDFDWNLKHGRVFIIKSYSENDIHRSIKYNIWCSTEHGNKRLDA

AYRSMNGKGPVYLLFSVNGSGHFCGVAEMKSAVDYNTCAGVWSQDKWKGRFDVRWI

FVKDVPNSQLRHIRLENNENKPVTNSRDTQEVPLEKAKQVLKIIASYKHTTSIFDDFSHY

EKRQEEEESVKKERQGRGK (amino acid sequence of YTHDF1)
                                                     SEQ ID NO: 6
HPVLEKLKAAHSYNPKEFEWNLKSGRVFIIKSYSEDDIHRSIKYSIWCSTEHGNKRLDSA

FRCMSSKGPVYLLFSVNGSGHFCGVAEMKSPVDYGTSAGVWSQDKWKGKFDVQWIFV

KDVPNNQLRHIRLENNDNKPVTNSRDTQEVPLEKAKQVLKIISSYKHTTSIFDDFAHYEK

RQEEEEVVRKERQSRNKQ (amino acid sequence of YTHDF1 mut)
                                                     SEQ ID NO: 7
GRVFIIKSYSEDDIHRSIKYSIWCSTEHGNKRLDSAFRCMSSKGPVYLLFSVNGSGHFCG

VAEMKSPVDYGTSAGVWSQDKWKGKFDVQWIFVKDVPNNQLRHIRLENNDNKPVTNS

RDTQEVPLEKAKQVLKIISSYKHTTSIFDDFAHYEKRQEEEEVVRKERQSRNKQ (amino acid sequence of YTHDF1 D401N)
                                                     SEQ ID NO: 8
HPVLEKLKAAHSYNPKEFEWNLKSGRVFIIKSYSEDNIHRSIKYSIWCSTEHGNKRLDSA

FRCMSSKGPVYLLFSVNGSGHFCGVAEMKSPVDYGTSAGVWSQDKWKGKFDVQWIFV

KDVPNNQLRHIRLENNDNKPVTNSRDTQEVPLEKAKQVLKIISSYKHTTSIFDDFAHYEK

RQEEEEVVRKERQSRNKQ (amino acid sequence of YTHDF3)
                                                     SEQ ID NO: 9
VHPVLEKLKAINNYNPKDFDWNLKNGRVFIIKSYSEDDIHRSIKYSIWCSTEHGNKRLDA

AYRSLNGKGPLYLLFSVNGSGHFCGVAEMKSVVDYNAYAGVWSQDKWKGKFEVKWI

FVKDVPNNQLRHIRLENNDNKPVTNSRDTQEVPLEKAKQVLKIIATFKHTTSIFDDFAHY

EKRQEEEEAMRRERNRNKQ (amino acid sequence of YTHDC1)
                                                     SEQ ID NO: 10
SKLKYVLQDARFFLIKSNNHENVSLAKAKGVWSTLPVNEKKLNLAFRSARSVILIFSVRE

SGKFQGFARLSSESHHGGSPIHWVLPAGMSAKMLGGVFKIDWICRRELPFTKSAHLTNP

WNEHKPVKIGRDGQEIELECGTQLCLLFPPDESIDLYQVIHKMRHK
```

```
(amino acid sequence of YTHDC2)
                                             SEQ ID NO: 11
PVRYFIMKSSNLRNLEISQQKGIWSTTPSNERKLNRAFWESSIVYLVFSVQGSGHFQGFS

RMSSEIGREKSQDWGSAGLGGVFKVEWIRKESLPFQFAHHLLNPWNDNKKVQISRDGQ

ELEPLVGEQLLQLWERLPLGEKNTTD (amino acid sequence of rAPOBEC1)
                                             SEQ ID NO: 12
MSSETGPVAVDPTLRRRIEPHEFEVFFDPRELRKETCLLYEINWGGRHSIWRHTSQNTNK

HVEVNFIEKFTTERYFCPNTRCSITWFLSWSPCGECSRAITEFLSRYPHVTLFIYIARLY

HHADPRNRQGLRDLISSGVTIQIMTEQESGYCWRNFVNYSPSNEAHWPRYPHLWVRLY

VLELYCIILGLPPCLNILRRKQPQLTFFTIALQSCHYQRLPPHILWATGLK (amino acid sequence of hAICDA)
                                             SEQ ID NO: 13
MDSLLMNRRKFLYQFKNVRWAKGRRETYLCYVVKRRDSATSFSLDFGYLRNKNGCHV

ELLFLRYISDWDLDPGRCYRVTWFTSWSPCYDCARHVADFLRGNPNLSLRIFTARLYFC

EDRKAEPEGLRRLHRAGVQIAIMTFKDYFYCWNTFVENHERTFKAWEGLHENSVRLSR

QLRRILLPLYEVDDLRDAFRTLGL (amino acid sequence of hAPOBEC3A)
                                             SEQ ID NO: 14
MEASPASGPRHLMDPHIFTSNFNNGIGRUKTYLCYEVERLDNGTSVKMDQHRGFLHNQ

AKNLLCGFYGRHAELRFLDLVPSLQLDPAQIYRVTWFISWSPCFSWGCAGEVRAFLQEN

THVRLRIFAARIYDYDPLYKEALQMLRDAGAQVSEVITYDEFKHCWDTFVDHQGCPFQP

WDGLDEHSQALSGRLRAILQNQGN (amino acid sequence of catalytic domain of ADAR2)
                                             SEQ ID NO: 15
QLHLPQVLADAVSRLVLGKFGDLTDNFSSPHARRKVLAGVVMTTGTDVKDAKVISVST

GTKCINGEYMSDRGLALNDCHAEIISRRSLLRFLYTQLELYLNNKDDQKRSIFQKSERGG

FRLKENVQFHLYISTSPCGDARIFSPHEPILEEPADRHPNRKARGQLRTKIESGQGTIPVRS

NASIQTWDGVLQGERLLTMSCSDKIARWNVVGIQGSLLSIFVEPIYFSSIILGSLYHGDHL

SRAMYQRISNIEDLPPLYTLNKPLLSGISNAEARQPGKAPNFSVNWTVGDSAIEVINATT

GKDELGRASRLCKHALYCRWMRVHGKVPSHLLRSKITKPNVYHESKLAAKEYQAAKA

RLFTAFIKAGLGAWVEKPTEQDQFSLT

SEQ ID NO: 16
(SGSETPGTSESATPE)

SEQ ID NO: 17
(SGSETPGTSESATPES)

SEQ ID NO: 18
((GGGGS)_3)

SEQ ID NO: 19
((GGGGS)_10)

SEQ ID NO: 20
((GGGGS)_20)

SEQ ID NO: 21
(A(EAAAK)_3A)

SEQ ID NO: 22
(A(EAAAK)_10A)

SEQ ID NO: 23
(A(EAAAK)_20A)

SEQ ID NO: 24
(PKKKRKV)
```

-continued (LPPLERLTL) SEQ ID NO: 25

(MDPVVVLGLCLSCLLLLSLWKQSYGGG) SEQ ID NO: 26

(EQKLISEEDL) SEQ ID NO: 27

(GKPIPNPLLGLDST) SEQ ID NO: 28

(IPNPLLGLD) SEQ ID NO: 29

(DYKDDDDK) SEQ ID NO: 30

(DYKDHDGDYKDHDIDYKDDDDK) SEQ ID NO: 31

(ISLIAALAVDHVIGMETVMPWNLPADLAWFKRNTLNKPVI SEQ ID NO: 32
MGRHTWESIGRPLPGRKNIILSSQPSTDDRVTWVKSVDEAIAACGDVPEIMVIGGGRVYE
QFLPKAQKLYLTHIDAEVEGDTHFPDYEPDDWESVFSEFHDADAQNSHSYCFEILERR)

(YPYDVPDYA) SEQ ID NO: 33

(GGAGTTGATTGAGGTAAAGCG) SEQ ID NO: 34

(GUUCUUCUGUGGACUGUG) SEQ ID NO: 35

(AGACTCCCGGGACCTCAGAG) SEQ ID NO: 36

(ACTCCCGGGACCTCAGAGTCCGCCACACCAGAAGGCCGGGTTTTCATCATTAAG) SEQ ID NO: 37

(CGGGTTTAAACTCAGGCGTAGTC) SEQ ID NO: 38

(GTGGGGGCGATCTTTATTGTGGCGG) SEQ ID NO: 39

(TGTGCAATCAAAGTCCTCGGCCAC) SEQ ID NO: 40

(GCCAATGCTGTCTGGTTGCGCC) SEQ ID NO: 41

(GGAGGCTTCTGCGGTTCTGGAG) SEQ ID NO: 42

(CAGCAAGCAGGAGTATGACGAGTC) SEQ ID NO: 43

(CATGCCAATCTCATCTTG) SEQ ID NO: 44

(CATGTACGTTGCTATCCAGGC) SEQ ID NO: 45

(CTCCTTAATGTCACGCACGAT) SEQ ID NO: 46

(CGAAGATCCCCACGTGTAAAGACTAC) SEQ ID NO: 47

(CATCCTGCTCACCTCTTTGAGG) SEQ ID NO: 48

(GTGTTAGATGATGTCTCCATTCGGAG) SEQ ID NO: 49

-continued (CACTTTCCTCCTGTATGAGCGG) SEQ ID NO: 50

(GCCAAGAGGCAACACACCAAC) SEQ ID NO: 51

(CGGTTTCTCTCGGTCTGTTTTCC) SEQ ID NO: 52

(CAGAAGGCGACAACACAGCAACACC) SEQ ID NO: 53

(TACTTCCAATCCAATGCA) SEQ ID NO: 54

(TTATCCACTTCCAATGTTATTA) SEQ ID NO: 55

(TACTAGGACGCACCTTA) SEQ ID NO: 56

(TACTAGGATGCACCTTA) SEQ ID NO: 57

*E. coli* codon optimized APOBEC1-YTH for protein purification:

SEQ ID NO: 58
ATGAGCAGCGAAACCGGTCCGGTGGCGGTTGACCCGACCCTGCGTCGTCGTATTGA
GCCGCACGAGTTCGAAGTGTTCTTTGATCCGCGTGAGCTGCGTAAGGAAACCTGCCT
GCTGTACGAAATTAACTGGGGTGGCCGTCACAGCATCTGGCGTCACACCAGCCAGA
ACACCAACAAGCACGTTGAGGTGAACTTCATCGAAAAATTTACCACCGAGCGTTACT
TCTGCCCGAACACCCGTTGCAGCATTACCTGGTTTCTGAGCTGGAGCCCGTGCGGTG
AATGCAGCCGTGCGATCACCGAGTTCCTGAGCCGTTATCCGCACGTTACCCTGTTTA
TCTACATTGCGCGTCTGTATCACCACGCGGACCCGCGTAACCGTCAAGGTCTGCGTG
ATCTGATCAGCAGCGGCGTGACCATCCAGATTATGACCGAGCAAGAAAGCGGTTAC
TGCTGGCGTAACTTCGTTAACTATAGCCCGAGCAACGAAGCGCATTGGCCGCGTTAC
CCGCACCTGTGGGTGCGTCTGTACGTTCTGGAGCTGTATTGCATCATTCTGGGCCTGC
CGCCGTGCCTGAACATTCTGCGTCGTAAGCAGCCGCAACTGACCTTCTTTACCATCG
CGCTGCAGAGCTGCCACTACCAACGTCTGCCGCCGCACATTCTGTGGGCGACCGGTC
TGAAGAGCGGCAGCGAAACCCCGGGTACCAGCGAAAGCGCGACCCCGGAGCCGCA
CCCGGTGCTGGAGAAACTGCGTAGCATCAACAACTATAACCCGAAGGACTTCGATT
GGAACCTGAAACACGGTCGTGTTTTTATCATTAAGAGCTACAGCGAAGACGATATCC
ACCGTAGCATTAAATATAACATCTGGTGCAGCACCGAGCACGGCAACAAGCGTCTG
GACGCGGCGTACCGTAGCATGAACGGTAAAGGCCCGGTGTATCTGCTGTTCAGCGTT
AACGGTAGCGGCCACTTTTGCGGTGTGGCGGAAATGAAAAGCGCGGTTGATTACAA
CACCTGCGCGGGTGTGTGGAGCCAGGACAAGTGGAAAGGCCGTTTCGATGTTCGTT
GGATTTTTGTGAAGGACGTTCCGAACAGCCAACTGCGTCACATCCGTCTGGAGAACA
ACGAAAACAAACCGGTGACCAACAGCCGTGATACCCAGGAAGTGCCGCTGGAAAA
GGCGAAACAAGTTCTGAAGATCATTGCGAGCTACAAACACACCACCAGCATCTTCG
ACGATTTTAGCCACTATGAGAAGCGTCAGGAAGAGGAAGAGAGCGTGAAGAAGGA
GCGTCAAGGTCGTGGCAAACTGGAGTACCCGTATGACGTTCCGGATTATGCGTAAAT
TGGAAGTGGATAA

E. coli codon optimized APOBEC1-YTHmut for protein purification:

SEQ ID NO: 59

ATGAGCAGCGAAACCGGTCCGGTGGCGGTTGACCCGACCCTGCGTCGTCGTATTGA

GCCGCACGAGTTCGAAGTGTTCTTTGATCCGCGTGAGCTGCGTAAGGAAACCTGCCT

GCTGTACGAAATTAACTGGGGTGGCCGTCACAGCATCTGGCGTCACACCAGCCAGA

ACACCAACAAGCACGTTGAGGTGAACTTCATCGAAAAATTTACCACCGAGCGTTACT

TCTGCCCGAACACCCGTTGCAGCATTACCTGGTTTCTGAGCTGGAGCCCGTGCGGTG

AATGCAGCCGTGCGATCACCGAGTTCCTGAGCCGTTATCCGCACGTTACCCTGTTTA

TCTACATTGCGCGTCTGTATCACCACGCGGACCCGCGTAACCGTCAAGGTCTGCGTG

ATCTGATCAGCAGCGGCGTGACCATCCAGATTATGACCGAGCAAGAAAGCGGTTAC

TGCTGGCGTAACTTCGTTAACTATAGCCCGAGCAACGAAGCGCATTGGCCGCGTTAC

CCGCACCTGTGGGTGCGTCTGTACGTTCTGGAGCTGTATTGCATCATTCTGGGCCTGC

CGCCGTGCCTGAACATTCTGCGTCGTAAGCAGCCGCAACTGACCTTCTTTACCATCG

CGCTGCAGAGCTGCCACTACCAACGTCTGCCGCCGCACATTCTGTGGGCGACCGGTC

TGAAGAGCGGCAGCGAAACCCCGGGTACCAGCGAAAGCGCGACCCCGGAGGGTCG

TGTTTTTATCATTAAGAGCTACAGCGAAGACGATATCCACCGTAGCATTAAATATAA

CATCTGGTGCAGCACCGAGCACGGCAACAAGCGTCTGGACGCGGCGTACCGTAGCA

TGAACGGTAAAGGCCCGGTGTATCTGCTGTTCAGCGTTAACGGTAGCGGCCACTTTT

GCGGTGTGGCGGAAATGAAAAGCGCGGTTGATTACAACACCTGCGCGGGTGTGTGG

AGCCAGGACAAGTGGAAAGGCCGTTTCGATGTTCGTTGGATTTTTGTGAAGGACGTT

CCGAACAGCCAACTGCGTCACATCCGTCTGGAGAACAACGAAAACAAACCGGTGAC

CAACAGCCGTGATACCCAGGAAGTGCCGCTGGAAAAGGCGAAACAAGTTCTGAAGA

TCATTGCGAGCTACAAACACCACCAGCATCTTCGACGATTTTAGCCACTATGAGA

AGCGTCAGGAAGAGGAAGAGAGCGTGAAGAAGGAGCGTCAAGGTCGTGGCAAACT

GGAGTACCCGTATGACGTTCCGGATTATGCGTAAATTGGAAGTGGATAA

SEQ ID NO: 60

(METDTLLLWVLLLWVPGSTGD)

deaminase domain of rAPOBEC1

SEQ ID NO: 61

RRRIEPHEFEVFFDPRELRKETCLLYEINWGGRHSIWRHTSQNTNKHVEVNFIEKFTTER

YFCPNTRCSITWFLSWSPCGECSRAITEFLSRYPHVTLFIYIARLYHHADPRNRQGLRDLI

SSGVTIQIMTEQESGYCWRNFVNYSPSNEAHWPRYPHLWVRLYVLELYCIILGLPPCLNI

LRRKQPQLTFFTIALQSCHYQRLPPHILWATGLK deaminase domain of hAICDA

SEQ ID NO: 62

LMNRRKFLYQFKNVRWAKGRRETYLCYVVKRRDSATSFSLDFGYLRNKNGCHVELLF

LRYISDWDLDPGRCYRVTWFTSWSPCYDCARHVADFLRGNPNLSLRIFTARLYFCEDRK

AEPEGLRRLHRAGVQIAIMTFKDYFYCWNTFVENHERTFKAWEGLHENSVRLSRQLRRI

LLPL deaminase domain of hAPOBEC3A

SEQ ID NO: 63

TSNFNNGIGRHKTYLCYEVERLDNGTSVKMDQHRGFLHNQAKNLLCGFYGRHAELRFL

DLVPSLQLDPAQIYRVTWFISWSPCFSWGCAGEVRAFLQENTHVRLRIFAARIYDYDPLY

KEALQMLRDAGAQVSIMTYDEFKHCWDTFVDHQGCPFQPWDGLDEHSQALSGRLR

-continued catalytic domain of ADAR2

SEQ ID NO: 64

MDSLLMNRREFLYQFKNVRWAKGRRETYLCYVVKRRDSATSFSLDFGYLRNKNGCHV

ELLFLRYISDWDLDPGRCYRVTWFISWSPCYDCARHVADFLRGNPNLSLRIFTARLYFCE

AGRREPEGLRRLHRAGVQIAIMTFKDYFYCWNTFVENHGRTFKAWEGLHENSVRLSRQ

LRRILL

---

What is claimed is:

1. A fusion protein comprising an $N^6$-methyladenosine ($m^6A$) binding domain of a YT521-B homology (YTH) domain-containing protein fused to a catalytic domain of a cytidine deaminase or a catalytic domain of an adenosine deaminase.

2. The fusion protein of claim 1, wherein the $m^6A$ binding domain is fused to the catalytic domain via a peptide linker.

3. The fusion protein of claim 1, wherein the $m^6A$ binding domain comprises a polypeptide having at least 95% identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

4. The fusion protein of claim 1, wherein the catalytic domain comprises a polypeptide having at least 95% identity to SEQ ID NO 12 or a catalytic fragment thereof, SEQ ID NO: 13 or a catalytic fragment thereof; SEQ ID NO: 14 or a catalytic fragment thereof; or SEQ ID NO: 15.

5. The fusion protein of claim 1, wherein the fusion protein further comprises a localization element.

6. The fusion protein of claim 5, wherein the localization element is fused to the N-terminus or the C-terminus of the fusion protein.

7. A recombinant nucleic acid encoding the fusion protein of claim 1.

8. A DNA construct comprising a promoter operably linked to the recombinant nucleic acid of claim 7.

9. The DNA construct of claim 8, wherein the promoter is an inducible promoter.

10. A vector comprising the recombinant nucleic acid claim 7.

11. A host cell comprising the recombinant nucleic acid of claim 7.

12. A host cell comprising the DNA construct of claim 9.

13. The host cell of claim 11, wherein the cell is a mammalian cell.

14. A non-human transgenic animal comprising the host cell of claim 13.

15. A method for detecting $m^6A$ residues in the transcriptome of one or more cells comprising:
   a) isolating RNA from the transcriptome of one or more cells that expresses the fusion protein of claim 1;
   b) amplifying one or more target sequences in the isolated RNA; and
   c) sequencing the one or more amplified target sequences to identify cytidine to uridine deamination at sites adjacent to $m^6A$ residues, thus detecting the $m^6A$ residues in the RNA of the one of more cells.

16. The method of claim 15, wherein a recombinant nucleic acid encoding the fusion protein is introduced into the one or more cells prior to isolating RNA from the cell.

17. The method of claim 15, wherein the fusion protein is stably or transiently expressed in the cell.

18. The method of claim 15, wherein the one or more target sequences are amplified by reverse transcriptase polymerase chain reaction (RT-PCR).

19. The method of claim 15, wherein the RNA comprises one or more RNAs selected from the group consisting of: messenger RNA (mRNA), transfer RNA (tRNA), small nuclear RNA (snRNA), a regulatory RNA, a transfer-messenger RNA (tmRNA), ribosomal RNA (rRNA), microRNA (miRNA), long noncoding RNA (lncRNA), and circular RNA (circRNA).

20. A method for detecting $m^6A$ residues in the RNA of the transcriptome of one or more cells comprising:
   a) fixing a cell or tissue that expresses the fusion protein of claim 1; and
   b) detecting cytidine to uridine deamination in the RNA, wherein cytidine to uridine deamination is detected via mutation-sensitive in situ hybridization.

21. A method for detecting $m^6A$ residues in a biological sample comprising:
   a) isolating RNA from the transcriptome of a biological sample;
   b) contacting the RNA with the fusion protein of claim 1;
   c) amplifying one or more target sequences in the RNA; and
   d) identifying cytidine to uridine deamination at sites adjacent to $m^6A$ residues in the one or more amplified target sequences, thus detecting the $m^6A$ residues in the one or more amplified target sequences.

22. The method of claim 21, wherein the RNA comprises one or more RNAs selected from the group consisting of: messenger RNA (mRNA), transfer RNA (tRNA), small nuclear RNA (snRNA), a regulatory RNA, a transfer-messenger RNA (tmRNA), ribosomal RNA (rRNA), microRNA (miRNA), long noncoding RNA (lncRNA), and circular RNA (circRNA).

23. The method of claim 21, wherein the biological sample is a biopsy.

24. The method of claim 21, wherein the one or more target sequences are amplified by reverse transcriptase polymerase chain reaction (RT-PCR).

25. The method of claim 21, wherein cytidine to uridine deamination is identified by sequencing the one or more amplified target sequences.

26. A method for diagnosing a disease in a subject comprising:
   a) isolating RNA from the transcriptome of a biological sample;
   b) contacting the RNA with the fusion protein of claim 1;
   c) amplifying one or more target sequences in the RNA; and
   d) identifying cytidine to uridine deamination at sites adjacent to $m^6A$ residues in the one or more amplified target sequences to identify a pattern of $m^6A$ residues, a difference in the pattern of $m^6A$ residues as compared to a reference pattern of $m^6A$ residues from a reference population(s), indicating the subject has or is at risk for developing the disease.

27. The method of claim 26, wherein the disease is selected from the group consisting of: cancer, an autoimmune disorder, a neurodegenerative disorder, and a viral infection.

28. The method of claim 26, wherein the biological sample is a biopsy.

29. The method of claim 26, wherein the one or more target sequences are amplified by reverse transcriptase polymerase chain reaction (RT-PCR).

30. The method of claim 26, wherein cytidine to uridine deamination is identified by sequencing the one or more amplified target sequences.

31. A method for determining the efficacy of a selected treatment for a disease in a subject comprising:
   a) isolating RNA from the transcriptome of a biological sample from the subject before the selected treatment;
   b) contacting the RNA with the fusion protein of claim 1,
   c) amplifying one or more target sequences in the RNA;
   d) identifying cytidine to uridine deamination at sites adjacent to $m^6A$ residues to identify a pattern of $m^6A$ residues in the one or more amplified target sequences;
   e) treating the subject with the selected treatment,
   f) isolating RNA from a biological sample from the subject at one or more times after administration of the selected treatment;
   g) amplifying one or more target sequences in the RNA of step f);
   h) identifying cytidine to uridine deamination at sites adjacent to $m^6A$ residues to identify a pattern of $m^6A$ residues in the one or more amplified target sequences of step g); and
   i) comparing the pattern of $m^6A$ residues identified in step (d) and (h) to determine whether the pattern of $m^6A$ residues is the same or whether the $m^6A$ residues detected in step (d) or (h) is more similar to a reference pattern, a pattern of $m^6A$ residues in step (h) more similar to the reference pattern indicating the selected treatment is effective for treating the disease in the subject.

32. The method of claim 31, wherein the disease is selected from the group consisting of cancer, an autoimmune disorder, a neurodegenerative disorder, and a viral infection.

33. The method of claim 31, wherein the biological sample is a biopsy.

34. The method of claim 31, wherein the one or more target sequences are amplified by reverse transcriptase polymerase chain reaction (RT-PCR).

35. The method of claim 31, wherein cytidine to uridine deamination is identified by sequencing the one or more amplified target sequences.

36. A kit comprising:
   a) the fusion protein of claim 1; and
   b) one or more primers for amplification of one or more target RNA sequences.

\* \* \* \* \*